(12) United States Patent
Kerr et al.

(10) Patent No.: US 12,404,294 B2
(45) Date of Patent: *Sep. 2, 2025

(54) GLYCOLIPOPEPTIDE BIOSURFACTANTS

(71) Applicant: Croda International Plc, Goole (GB)

(72) Inventors: Russell Greig Kerr, Charlottetown (CA); Bradley Arnold Haltli, New Haven (CA); Douglas Hubert Marchbank, Stratford (CA); Fabrice Berrué, Halifax (CA)

(73) Assignee: CRODA INTERNATIONAL PLC, Goole (GB)

( * ) Notice: Subject to any disclaimer, the term of this patent is extended or adjusted under 35 U.S.C. 154(b) by 317 days.

This patent is subject to a terminal disclaimer.

(21) Appl. No.: 18/099,723

(22) Filed: Jan. 20, 2023

(65) Prior Publication Data

US 2023/0227489 A1 Jul. 20, 2023

Related U.S. Application Data

(60) Continuation of application No. 16/817,193, filed on Mar. 12, 2020, now Pat. No. 11,608,352, which is a division of application No. 16/090,888, filed as application No. PCT/EP2017/058296 on Apr. 6, 2017, now abandoned.

(30) Foreign Application Priority Data

Apr. 6, 2016 (GB) ...................... 1605875

(51) Int. Cl.
| | | |
|---|---|---|
| C07H 15/04 | (2006.01) | |
| C02F 3/34 | (2023.01) | |
| C07H 1/08 | (2006.01) | |
| C11D 1/00 | (2006.01) | |
| C11D 1/66 | (2006.01) | |
| C11D 3/38 | (2006.01) | |
| C12N 1/20 | (2006.01) | |
| C12N 15/52 | (2006.01) | |
| C12P 19/44 | (2006.01) | |
| C11D 1/10 | (2006.01) | |
| C12R 1/01 | (2006.01) | |

(52) U.S. Cl.
CPC .............. *C07H 15/04* (2013.01); *C02F 3/34* (2013.01); *C07H 1/08* (2013.01); *C11D 1/008* (2013.01); *C11D 1/662* (2013.01); *C11D 3/381* (2013.01); *C12N 1/205* (2021.05); *C12N 15/52* (2013.01); *C12P 19/44* (2013.01); *C11D 1/10* (2013.01); *C12R 2001/01* (2021.05)

(58) Field of Classification Search
CPC .......... C07H 15/04; C11D 1/008; C11D 1/662
USPC ....................................................... 435/71.1
See application file for complete search history.

(56) References Cited

U.S. PATENT DOCUMENTS

| | | |
|---|---|---|
| 2008/0274959 A1 | 11/2008 | Haltli et al. |
| 2013/0085067 A1 | 4/2013 | Schofield et al. |
| 2013/0331466 A1 | 12/2013 | Gross et al. |

OTHER PUBLICATIONS

STN Structure search Jan. 6, 2024 pp. 1-49.*
Witkowsk et al., "Conversion of a ß-Ketoacyl Synthase to a Malonyl Decarboxylase by Replacement of the Active-Site Cysteine with Glutamine", Biochemistry, 1999, 38, 11643-11650.
Wittman et al., "Role of DptE and DptF in the Lipidation Reaction of Daptomycin", the FEBS Journal, 275, (2008), pp. 5343-5354.
Wu et al., "Programmable One-pot Glycosylation", Top. Curr. Chem. 2011, 301, pp. 223-252.
Ziemert et al., "The Natural Product Domain Seeker NaPDoS: A Phylogeny Based Bioinformatic Tool to Classify Secondary Metabolite Gene Diversity", PLoS ONE, Mar. 2012, vol. 7, Issue 3, 9 pages.
Entire patent prosecution history of U.S. Appl. No. 16/090,888, filed Oct. 3, 2018, entitled, "Glycolipopeptide Biosurfactants."
Entire patent prosecution history of U.S. Appl. No. 16/817,193, filed Mar. 12, 2020, entitled, "Glycolipopeptide Biosurfactants."
Abdel-Mawgoud et al., "Rhamnolipids: Detection, Analysis, Biosynthesis, Genetic Regulation, and Bioengineering of Production", Biosurfactants, Microbiology 20, pp. 13-55.
Altschul et al., "Gapped BLAST and PSI-BLAST: A New Generation of Protein Database Search Programs", Nucleic Acids Res., 1997, vol. 25, No. 17, pp. 3389-3402.
Aziz et al., "The RAST Server: Rapid Annotations using Subsystems Technology", BMC Genomics 9, 2008, pp. 1-15.
Bachman et al., "Methods for In Silico Prediction of Microbial Polyketide and Nonribosomal Peptide Biosynthetic Pathways from DNA Sequence Data", Methods in Enzymology, 2009, vol. 458, pp. 181-217.
Baltz, R., "MbtH Homology Codes to Identify Gifted Microbes for Genome Mining", J. Ind. Microbiol. Biotechnol., 2014, vol. 41, pp. 357-369.
Breton et al., "Structures and Mechanisms of Glycosyltransferases" Glycobiology, 2006, vol. 16, No. 2, pp. 29R-37R.

(Continued)

*Primary Examiner* — Tekchand Saidha
*Assistant Examiner* — Mohammad Y Meah
(74) *Attorney, Agent, or Firm* — Buchanan Ingersoll & Rooney PC

(57) ABSTRACT

Surfactants based on a newly discovered class of compounds include a hydrophobic lipid oligomer covalently linked to a peptide or peptide-like chain and a carbohydrate moiety, and a serine-leucinol dipeptide linked to the lipid oligomer. Such surfactants can be used to create an oil-in-water or water-in-oil emulsion by mixing together a polar component; a non-polar component; and the surfactant. Biosurfactants of the newly discovered class can be made by isolating and culturing a microorganism which produces the biosurfactant, and then isolating the biosurfactant from the culture. A microorganism can be engineered to produce biosurfactant of this newly discovered class by expressing a set of heterologous genes involved in the biosynthesis of the biosurfactant in the microorganism.

10 Claims, 23 Drawing Sheets

Specification includes a Sequence Listing.

(56) References Cited

OTHER PUBLICATIONS

Brettin et al., "RASTtk: A Modular and Extensible Implementation of the RAST algorithm for Building Custom Annotation Pipelines and Annotating Batches of Genomes", Scientific Reports, 5:8365, pp. 1-6.

Cai et al., "Efficient synthesis of a 6-deoxytalose tetrasaccharide related to the antigenic O-polysaccharide produced by Aggregatibacter actinomycetemcomitans serotype c.", Carbohydr. Res. 2010, 345, 1230-1234.

Chaisson et al., "Taxon Ordering in Phylogenetics Trees by Means of Evolutionary Algorithms", BMC Bioformatics, 2012, 13:238, pp. 1-17.

Chin et al., "Nonhybrid, Finished Microbial Genome Assemblies From Long-Read SMRT Sequencing Date", Nature Methods, Jun. 2013, vol. 10, No. 6, pp. 563-569.

Clayden et al., Organic Chemistry, front cover of book, 1st edition, 2000, 1 page.

Coin et al., "Solid-phase peptide synthesis: from standard procedures to the synthesis of difficult sequences" Nat. Protoc. 2007, 2, 3247-3256.

Devos et al., "Practical Limits of Function Prediction" Proteins: Structure, Function, and Genetics, 2000, 41:98-107.

Deziel et al., "rhlA is Required for the Production of a Novel Biosurfactant Promoting Swarming Motility in Pseudomonas Aeruginos: 3-(3Hydroxyalkanoyloxy) Alkanoic Acids (HAAs), the Precursors of Rhamnolipids", Microbiology (2003), 149, pp. 2005-2013.

Du et al., "PKS and NRPS Release Mechanisms", Nat. Prod. Rep., 2010, vol. 27, pp. 255-278.

Dubeau et al., "Burkholderia Thailandensis Harbors Two Identical rhl Gene Clusters Responsible for the Biosynthesis of Rhamnolipids", BMC Microbiology, 2009, 9:263, pp. 1-12.

Franzetti et al., "Environmental Fate, Toxicity, Characteristics and Potential Applications of Novel Bioemulsifiers Produced by Variovorax Paradoxus 7bCT5", Bioresource Technology 108, (2012), pp. 245-251.

Gampe et al., "Modular Synthesis of Diphospholipid Oligosaccharide Fragments of the Bacterial Cell Wall and their use to Study the Mechanism of Moenomycin and other Antibiotics", Tetrahedron, Dec. 23, 2011 67(51), pp. 9771-9778.

Graupner et al., "Imaging Mass Spectrometry and Genome Mining Reveal Highly Antifungal Virulence Factor of Mushroom Soft Rot Pathogen", Angew. Chem. Int. Ed., 2012, vol. 51, pp. 13173-13177.

Grünewald et al., "Chemoenzymatic and Template-Directed Synthesis of Bioactive Macrocyclic Peptides", Microbiology and Molecular Biology Reviews, Mar. 2006, pp. 121-146.

Han et al., "Genome of the Root-Associated Plant Growth-Promoting Bacterium Variovorax Paradoxus Strain EPS", Genome Announcements, Sep./Oct. 2013, vol. 1, Issue 5, 2 pages.

Hansen et al., "The Loading Module of Mycosubtilin: An Adenylation Domain with Fatty Acid Selectivity", J. Am. Chem. Soc., 2007, 129, pp. 6366-6367.

Herbst et al., "Structural Basis of the Interaction of MbtH-like Proteins, Putative Regulators of Nonribosomal Peptide Biosynthesis, with Adenylating Enzymes", Journal of Biological Chemistry, Jan. 18, 2013, vol. 228, No. 3, pp. 1991-2003.

International Search Report and Written Opinion for International Application No. PCT/EP2017/058296, dated Oct. 25, 2017, 17 pages.

Irwin et al., "Molecular Cloning" A Laboratory Manual, Third Edition, 2001, 3 pages.

Kisselev, L., "Polypeptide Release Factors in Prokaryotes and Eukaryotes: Same Function, Different Structure", Structure, vol. 10, Jan. 2002, 2 pages.

Konz et al., "How do Peptide Synthetases Generate Structural Diversity" Chemistry and Biology, Feb. 1999, 6, pp. R39-R48.

Kopp et al., "Harnessing the Chemical Activation Inherent to Carrier Protein-bound Thioesters for the Characterization of Lipopeptide Fatty Acid Tailoring Enzymes", J. Am. Chem. Soc., 2008, 130, pp. 2656-2666.

Kraas et al., Functional Dissection of the Surfactin Synthetase Initiation Module Reveals Insights into the Mechanism of Lipoinitiation, Chemistry and Biology 17, Aug. 27, 2010, pp. 872-880.

Maddocks et al., "Structure and Function of the LysR-type Transcriptional Regulator (LTTR) Family Proteins", Microbiology (2008), 154, pp. 3609-3623.

Marchler-Bauer et al., "CD-Search: Protein Domain Annotations on the Fly", Nucleic Acids Research, vol. 32, Web Server Issue, pp. W327-W331.

May et al., "The dhb Operon of Bacillus Subtilis Encodes the Biosynthetic Template for the Catecholic Siderophore 2,3Dihydroxybenzoate-Glycine-Threonine Trimeric Ester Bacillibactin", The Journal of Biological Chemistry, 2001, vol. 278, No. 10, Issue of Mar. 9, pp. 7209-7217.

Miao et al., "Rhamnolipids as Platform Molecules for Production of Potential Anti-zoospore Agrochemicals", Journal of Agricultural and Food Chemistry, 2015, vol. 63, pp. 3367-3376.

Mootz et al., "The Tyrocidine Biosynthesis Operon of Bacillus Brevis: Complete Nucleotide Sequence and Biochemical Characterization of Functional Internal Adenylation Domains", Journal of Bacteriology, Nov. 1997, vol. 179, No. 21, pp. 6843-6850.

Myers et al., "A Whole-Genome Assembly of *Drosophila*", Science, Mar. 24, 2000, vol. 287, pp. 2196-2204.

Needleman et al., "A General Method Applicable to the Search of Similarities in the Amino Acid Sequence of Two Proteins", J. Mol. Biol. 1970, vol. 48, pp. 443-453.

Nguyen et al., "Characterization and Emulsification Properties of Rhamnolipid and Sophorolipid Biosurfactant and their Applications", Int. J. Mol. Sci., 2011, 12, pp. 1232-1244.

Overbeek et al., "The SEED and the Rapid Annotation of Microbial Genomes using Subsystems Technology (RAST)", Nucleic Acids Research, 2014, vol. 42, pp. D206-D214.

Pandey et al., "Efficient Total Synthesis of (−)-(3S,6R)-3,6-Dihydorxy-10-methylundecanoic Acid", Eur. J. Org. Chem, 2007, pp. 369-373.

Rahim et al., "Involvement of the rml Locus in Core Oligosaccharide and O Polysaccharide Assembly in Pseudomonas Aeruginosa", Microbiology (2000), 146, pp. 2803-2814.

Reis et al., "Gene Regulation of Rhamnolipid Production in Pseudomonas Aeruginosa—A Review", Bioresource Technology, 102, (2011), pp. 6377-6384.

Rice et al., "Emboss: The European Molecular Biology Open Software Suite", TIG, 2000, vol. 16. No. 6, pp. 276-277.

Santos et al., "Biosurfactants: Multifunctional Biomolecules of the 21st Century", International Journal of Molecular Sciences, (2016), 17, 32 pages.

Schneekloth et al., "Neurotrophic Peptide Aldehydes: Solid Phase Synthesis of Fellutamide B and a Simplified Analog", Bioorg. Med. Chem. Lett., Jul. 15, 2006, 16(14), pp. 3855-3858.

Scott, P.J.H., "Linker Strategies in Solid-Phase Synthesis", John Wiley & Sons Ltd: Chichester, U.K., 2009; pp. 50-51.

Stachellhaus et al., "The Specialty-Conferring Code of Adenylation Domains in Nonribosomal Peptide Synthetases", Chemistry 7 Biology, Aug. 1999, 6, pp. 493-505.

Takahashi et al., "The anomeric effect revisited. A possible role of the CH/n hydrogen bond", Carbohydr. Res. 2007, 342, pp. 1202-1209.

Toribio et al., "Rhamnolipids: Production in Bacteria other than Pseudomonas Aeruginosa", Eur. J. Lipid Sci. Technol., 2010, 112, pp. 1082-1087.

Valeur et al., "Amide bond formation: beyond the myth of coupling reagents", Chem. Soc. Rev. 2009, 38, pp. 606-631.

Whisstock et al., "Prediction of protein function from protein sequence and structure", Quarterly Reviews of Biophysics 36, 3 (2003), pp. 307-340.

\* cited by examiner

SEQ ID NO 1
LENGTH: 12721
TYPE: DNA
ORGANISM: Variovorax paradoxus

SEQUENCE: 1 gtcgtgtctccttcttttcgtggggtgttccaacgggccgactgggaggtcggctgaaaaccgctcgccagtgtgcg
tgccgcaaggtttgccttcaataaaataatcaagctaagtaatatgaatggcatgcatatcgactcggtcgacctca
atctgctgcgcctgttcgatgcggtctaccgcgagcgcagcgtgagccgcgccgcgggagtcgctgggcctcacgcag
cctgcggcaagccatgggctgggacggctgcggctgcttttgaaagacgcgctcttcacgcgtgccccggcggcgt
ggcgccacgccgcgcgccgaccggctcgcggtggcggtcaggcggcgtcggcacgatcgaagcggcgctgcacg
agcccgatcgcttcgagcccaggtgtcgcgcaagagctttcgtattcacatgagcgacatcggcgaggggcgcttc
ctgcccgcgctgatggcgcggctcggcgagctggcgcccggcgtgcggctggagaccctgccgctcttgcctgcgga
ggttgcgcccgcactcgacagcggccgcatcgatttcgccttcggctttctctcgaccgtgcgcgacacgcagcgca
cgcatcttctgaaagaccgctacatcgtgctgctgcgcaagggccatcccttgtgaagcgccggcgcaaggggcag
gcgctgctcgaggcgctgcaggagctcgactacgtggcggtgcgcacgcacgccgacacgctgcgcatcttgcagtt
gctcaacctcgaagaccgcctgcgcctcacgaccgagcacttcatggtgctaccggccatcgtgcgcgccaccgatc
tcgcggtggtgatgccgcgcaacatcgcgcgagggtttgcggaggagggcggctacgcgatcgtcgagccgccgttt
ccgctgcgcgatttcagcgtgtcgctgcactggagcaagcgcttcgagggcgacccggccaaccgttggttgcggca
ggtgatcacggcgctgttctccgagcgcggctgaagttcgaccaccaaagtacgcgccgcgcggtgcaagcgcgcgc
gactgcgcgagtaacacgccgagagattcccctacagctttctcgcccagttgctgcatcgcaacattcttttgggg
tgcatgacgcgcgaaatacgatgaaagccttcgattccgaaagccgcgattcaggtcgcaacttcgggatgaaatct
ttcgcgctcaaagacgttcgtgaaatgttttcttccctaaaaccgtcactgaaagtgttgaaaccacttgtacagtg
gactggcaatgtgaacggattgttaccgcggagcaccggcatttctccttgagcggccgatgcacgacgcgtccatt
tcacgcgcacatgcatcgttgccaatttcactcaagacctggagaagtgcatgagtaccgtcgatcagctgggccgc
accgccccccttacctcggggcagatggcgatgtggctcggcgcaaagttcgcgtcgcccgacaccaatttcaatct
cgccgaagccatcgacatcgcaggcgagatcgacccgcgatcttcctggcggccatgcgacaggtggccgatgaag
tcgaggccacgcgcctgagcttcatcgataccccgcaagggccacgacaggtcgtcgcgcccgttttcaccggcgag
atccctacctcgacctcagcggcgagagcgatccgcaggccgaggccgagcgctggatgcatgcggactacaccccg
cagcatcgacctcgcgcacgggcagctgtggctgtccgcgctgatccgcctcgcgcccgatcgccacatctggtacc
accgcagccatcacatcgcgctcgacggcttcagcggcggcctcatcgcacgccgcttcgccgacatctacaccgcg
atggtcgacaacaacgcagcggtgcccgaagactcgcgccttgcaccgatctcgcagctggccgacgaagaacatgc
ctatcgcgagtccggccgcttccgcgcgaccgccagtactggaccgagcgcttcgccgatgcaccgatccgttga
gcctcgcctcgcaccgctcggtcaacgtcggtggcctcttgcgccagacggtgcacctgccggcggccagcgtgcaa
gcctgcagaccatcgcgcaagagctcggcaccacgctgccgcaaatcctcatcgccaccaccgcggcctacctgta
ccgcgcaacgggcatcgaggacatggcaatcggcatcccgtcacgcgcgcaacaacgaccgcatgccgcgcgtgc
ccgcgatggtggccaacgcgctgccgctgcgcctggcgatgcgcgcgggacctgccgattccggaactgatccgcgaa
gtcggccggcagatgcggcagatcctgcggcaccagtcgtatcgctacgagcatttcgcgcagcgacctcaacatgct
ggtgaacaaccggcagctcttcaccacgtggtcaacgtcgagcccttcgactacgacttccgctttgcgggccatg
ccgcgaagccgcgcaacctctcgaacggcacggcgaggacctcggcatcttcctgtacgagcggcaacgggcag
gacctgcagatcgacttcgacgccaacccgcggtgcacaccgcagaggaactggccgatcaccagcgccggctgct
tgccttcatcgacgccgtgatccgcctgccgttgcaggccgtcggccagatcgacctgctcggtgccgaagagcggc
agcaattgctggtcgagtggaacgacacggcccacgccgtgcccgacacccatctcaccgcgttgatcgaagcgcag
ctcgcagccgatccgcaagccatcgcattgcgcttcgacggcgaggcgatgaacaacgaagaactgaaccgccgcg
caaccgtctcgcccacctgctgcgcgcacgcggcgctggcccggagcgcaccgtggcgctcgcgatccgcgttcga
tggacctgatgattgccttgctcgccacgttgaagaccggcgcggcctacctgccggtcgatccggatttccggcg
gaccgcatcgccttcatgctcggcgatgcgcagcccgtgtgcctcgtcacgaccgaagccctcgcggagtcgctgcc

Fig. 4

```
ggcagccgccccacattgctgctcgatgtagcgcaaacgattgcggatctggagagttgcaacgacaccaaccggg
gcatcgcgatcgacccttcgcatccggcctatgtgatctacacctcgggctcgaccggcatgcccaagggtgcggtc
gtgtcgcaccgcgccatcgtcaaccgcctgcgctggatgcaggaccgctacggccttcaggccgacgaccgcgtgct
gcagaagacgccttccagcttcgacgtgtcggtgtgggagttcttctggccgctgatcgacggtgccacgctggtgc
ttgcgaaaccggggcggccacaaggatgcggcctacctcgcggggctgatcgcggaggagggcatcaccacgatccac
ttcgtgccgtcgatgctcgaggtcttcctgctcgagcccacggcgggcgcatgcaccacgctgcgccgcgtgatctg
cagcggcgaagccttgtcgccgcgctgcaatcgcagttccagcagcacctctcgtgcgagctgcacaacctctacg
gtccgaccgaggccgcggtcgacgtcacctcgtgggagtgcgaacgcacggacgacgcagaagcctcgagcgttccc
atcggccgcccgatctggaacacccagatgcacgtgctcgacagcggcctgcagcccgtgccggccggcgtgactgg
cgagctgtacatcgcggggcgtcggcctcgcacgcggctacctcaagcgcccgttgctgagcgccgagcgtttcatcg
ccaaccctacggcacaccggcagccgcatgtaccgcaccggcgacctcgcgcgctggcgcaaggacggcagcctt
gacttcctcggccgcgccgaccagcaggtgaagatccggggcctgcgcatcgagccgggagagatcgaatccgtgct
gctgcagcatccgcaagtcgcgcaggccgcgtggtggcgcgcgaagacgtaccgggcgaaaagcgtctcgtggcct
acgtcgttgcgacggacgctgccgatccgcaagcggccgaactgcgcacgcgcctcgcgcaatcgctgcccgagtac
atggtgccttcggccttcgtcagcctcccgtcgctgccgctcggacccagcggcaagctcgaccgcaaggcgctgcc
gccccccgaagtgcaggccgccacgccgtacgccgcgccgcgcacgccgaccgaaaagatcctggccggcctctggg
ccgagacgctgcatttgccgcgcgtcggtgtcaacgacaacttcttcgaactcggcggccactcgctgatgatcgtg
cagctcatgtcgatgatccggcagcaattcatgatcgacctgccggtcgacacgctgttccaggtctccaccatcgc
gggccttgccgagctgctcgaccaggaatcggtcgcccgtccgagcctgactccgatgccgcgcccgcgcgcattc
cgctgtccttcgcgcagcgccgcctgtggctgatgaaccagctcgaaggcgcgaacccggcctacaacatgccgctc
gcgctgcgccgtgtcgggtgtgctcgatcgcaccgcattgcatgcggcgctcggcgacctggtgcagcgccacgagag
cctgcgcacggtctacccgaacgaagacgggctgccgtaccagcacatcctcgacggcgcggatgcgcgtccggcgg
tgatcgaggccgacagcagcgaagaagaaatcgcggcgcagcttcacgccgctgcgggccatgccttcgatctcggc
agcgcggcgccttgcgcgtctacctgttcaagctcgccggcgacgaacacgtgctgctgctgctcacgcaccacat
tgccggcgatgccgcctcgctgctgccgctagcgcgcgacatcagcgtggcctatgccgcgcgctgcgaaggcaagg
cgccggctgggagccgctgccgctgcaatacgccgactacgcgctgtggcagcaggagctgctcggcagcgaagac
gatgccgagagcatggccggccgccagcgtgagttctggcgttcctcgctgagcgacctgcccgagcaactggcgct
gccgtcgaccacgcacggccgctcgtgccgacctaccgcggcgatgtggtcccgctgcagattccgtcgcatgtgc
atgaacgcatcctgcaactggcgcgcgacgggcaggccagcgtcttcatggtgctgcaggccgcactcgcgggcctc
ctgagccgcctcggcgcgggcgacgacatcgtcatcggcagccgggtcgcgggggcgcagcgaccatgcgctggacga
actcatcggctgcttcgtcaacacgctggtgctgcgcactgacacctcgggccagccgagcctgcgcgagctggtct
cgcgcgtgcgcgccaccaacctcgcggcctatgcgaaccaggagttccgtacgaccgcctcgtggagctgctgcgt
ccgggccgctcgcgcgccaacctgccgctgttccaggtcatgctgggcttccagggcacgagccgcctgtcgttcag
cctgccgggcctgtcgatcgcgccgcagccggtggccatcgacaccgcgaagttcgacctgtcgttcatcctcggcg
agcaacgcggtgccgatggcctgccgggcggcatctccggcggcatccagtacagcaccgacctgttcgagcgcagc
acggtcgaggccatgggcgcgcggctggtgcgtttgctggaagaggcctgcgaggcgcccgacgatgcggtgagtgg
cctcgccatcctgagcgcggaagaaaccgaccgcctgctgtccgactggagcggccgcacgcgcgaccttgcgccgc
tctcgttcgccgacatggtggcctcgcatgccgcgggagcgcccgcttgcagatgcagtggtgctcgacgacgcgacc
gtcagctacgccgaactcgatgcacgcgccaaccggctctcgcacctgctgcgtgcgcaaggcatcggggttggcgc
catcgtcgcgacagtgctgccgcgttcgctcgacctcatcgtggcgcacttggccatcgtcaaggccggcgcggcct
acctgcccatcgaccccaaccacatggccgcgcgcagcgccttcgtgttcgaggaggccgcgccgcgcggtgctg
acgacgatgcgctgttgcccgagctggtcggcgttcccgctgcatcgcgctcgacagcgacagcatggttgccgc
gctggccatccagtcggatacgccgctggtgcatgcggccaatccacaggatgccgcctacctcatctacacctccg
gctccaccggcatgcccaagggcgtggtggtgccgcatgcgggcctgggcagcctcggcaccgcgatggcggagcgg
ctcgtcatcggccacggctcgcgcgtgctgcagttctcctccagcggcttcgacgcgtcggtgatggaccagctgat
ggcctttggcgccggtgccgcgctggtggtgccgggccggagcaactgctcggcacggagctggccgatctgctcg
agaagcaggccgtgagccacgcgctgattccgcccgccgcgctcgcgaccctgccgcacggcgagttcccgcacctg
cagacgctggtggtcggcggcgatgcctgcacgccgcgctggcggcgaagtggtcgcaaggccgccgcatgatcaa
cgcctacggcccgaccgagatcaccatctgcgcgagcatgagcgcgccgatgacggccgaggagttgccctccatcg
```

Fig. 4 (Cont. 1)

```
gccagccgatctggaacacgcggatgtatgtgctcgacagcgccctgcaaccggtgccgccgggtgtcgcgggcgag
ctctacatcgccggcagcggcgtggcgcgcggctatctcaaccggccggcattgagtgcggaacgcttcatcgccga
ccgcatggcgcgcccggcagccgcatgtaccgcagcggcgacctcgcacgctggcgcgccgacggcacgctcgact
tcctcggccgcgccgaccagcaggtgaagatccgggggcttccgcatcgagccggggcgagatcgaatccgtgctgctc
aagcacccgttgatcacgcaggccgccgtgatcgcccgcgaggacgtgcccggcgagaagcgcctggtcgcctactt
cgtcgccggttccgagccgcagcccaccgagctgcgcgcccacatggcgcaggccttgcccgactacatggtgcctt
cggccttcgtgcgcctgccgtcgctgccgctcacgcaaagcggcaagctcgacaagaaggcgctgccggtgcccgac
cagcagcccgccgcgctgtacgtggagcccgcacgccgaccgagaaactgctcgcgggcctctggtccgagacgct
gcacctggagcgtgtcggcatccacgacaacttcttcgagatcggcgggcattcgctcatggcgatccagctgggca
tgcgcatccgccagcaggtgcgcgcggacttcccgcacgccgaggtctacaaccgcccgacgattgccgacctggcc
gcctggctcgacaacgaaggcggcacggtcgaggcgctggacctgtcgcgcgagctcgacctgccgcgcacatccg
cccgcaggccactgcaccgaagctcgcaccgcgccggcgtgttcctcaccggcgcgagcggcttcgtcggcagtcacc
tgctggccgcgctgttgcgcgacaccgcggcctgcgtggtctgccacgtgcgcgcgcccgacgagcaggccggcgag
cagcgcctcaagcgcacgctggcccagcgccagctcggtgcgatctgggacaacgcgcgcatcaaggtcgtgaccgg
cgacctcggcaagccgcgcctgggcctcgatgacgctgccgtgcaactggtgcgcgacggctgcgacgccatctacc
actgcgccgcgcaggtcgacttcctgcatccctacgcgagcctcaagccgcgaacgtcgacagcgtggtcacgctg
ctcgaatggacggcgcaggggcgcgcgaagagcatgcactacgtctccacgctggctgtgatcgaccagaacaacaa
ggaagacaccatcaccgagcaatcggcgctggcctcatggagcgggctggtcgacggctacagccagagcaagtggg
tcggcgatgcgctggcccgcgaggcgcaggcgcgcggcatgccggtggcgatctaccggctgggggcagtcaccggc
gaccacacgcacgcgatctgcaatgccgacgacctgatctggcgcgtggcgcatctctatgccgacctggaagcgat
tcccgatatggacctgccgctcaacctcacaccggtggacgacgtggcgcgcgccatcctcggccttgcggcgcagg
aggcctcgtggggccaggtgttccacctgatgagccaggcggcgctgcgggtgcgcgacattccgcacgtcttcgag
cgcatgggcatgcggctggagccggtcgggctggagcccggctgcagcgcgcgcatgcacggctggccgtcgcgca
tgaccgcgacctggccgcggtgctcgccatcctcgaccgctacgacaccacggccacgccgcgcaggtgagcggcg
cggccacgcatgcgcagctcgaggccatcggcgcgccgatccgcccggtggaccgcgacctgctgcagcgctacttc
gtcgacctgggcatcgacaccaaggcgcgccgcgccctggaaaccaccacttcataggagcacacggaatggcacgc
tatctcatcgcagcaaccgccttgccgggacacgtcctgccgatgctggccatcgcgcagcatctggtgaaccaggg
gcacgaggtgcgggtgcacaccgcgagccagttcagggcgcaggccgaggcgaccggtgcgggcttcacgcccttcg
agcgcacgatcgacttcgactaccgcgacctggacaagcgctttcccgagcgccagcgcatcgcctcggcgcatgcg
cagctgtgcttcggcctgaagcacttctttgccgatgcgatggccgcgcagcatgcgggcctgcaatcgatcctcga
agacttcgaggccgatgccatcgtggtcgacacgatgttctgcggcactttcccgctgctgctaggcaaggagcgcg
aagaccgcccggccatcgtcggcatcggcatctcggcgctgccgctctcgagctgcgacaccgccttcttcggcacc
gcgctgccgccgtcgtccacgccggaagggcgggtgcgcaacaaggcgatgaacgccaacctcaaacaggcgatgtt
cggcgaggtgcaacgctacttcgacacgctgctcgcgcgttcgggcctggccgcgctgcccgatttcttcgtcgatg
cgatggtgaagctgcccgatcttttacctgcagctcaccgcgccttcgttcgaataccgcgcagcgacctgcccgcg
tcggtgcatttcgtcggccgctgctctcgccgcgagccgcgacttcacgcgcccgagtggtggcacgagctgga
cgacggccgctcggtcgtgctggtcacgcagggcacgctggccaaccagaatccgtcgcagctgatcggcccgacgc
tgcaggcgctggccggcgacaagaacatcctcgtcatcgccaccaccggcgggccggtgccgccgccctgacggtg
aacctgcccgccaacgcccgcgtggtgccgttcctgccctacgacggctgctgcccaagctgcacgcgatggtcac
caacggcggctacggctcggtcaaccatgcattgagcctcggtgtgccgctggtggtggccggcacctccgaagaga
agcccgagatcgccgcgcgcgtggcctggtcgggcgcgggcatcaacctcgccaccggccagccgaccgcgcgccag
gtcggcgacgcggtgcgcaaggtactgggcaactcgacctatcgccagcgtgcggcggtgctgcgtgaggacttcgc
ttgccatcgagcgctgaccggcatcgccggcgccctcgaggcacttctgcaaaccttcgcatccgcggaaatggctt
gaacctgaaccccatacgacaaaggaaatcccagatgagcaacccgttcgacgacaagaacgccagcttccaggtgc
tggtgaacgacgagggccagcactcgctgtggcccgccttcatcgccgtgccgccgctggcaggtggcgctggcg
ccgaccgaccgcgacgcctgcagcgcctacatcgcggcgaactggcaggacatgcgccgcgttcgctggtggtggc
cacggcggccggctgacgcgaggatgtccttcccgttcggtgccgtcgtcgtcacctatttcccgaccggcgagca
agtggcgaacctccattcgctggcgggcctcgtgtccgcacctctgcgtggtcgacaacacgccgcaggtgggcgatt
ggcatgcggcgctcgtcgatgcgggcgtttcggtgctgcacaacggcaaccgcggcggcatcgcgggcgccttcaac
```

Fig. 4 (Cont. 2)

```
cgcggcatcatcgacctcgaagcgcggggcgccgaactcttcttcctgctcgaccaggattcgaagctgccaccc gg
ctacttcgatgccatgtgcgaggctgcgatggtggcccgggagcggaagggcgagggcaatggtgaggaagacgcgg
ccttcctgatcggcccgctcgtccacgacacgaacctggacgcgctgatcccgcaattcggcctccagggcaaacgc
gtctaccagttcgacctgcggcagcccttcaccgagccgctgatgcgctgcgccttcatgatttcctcgggctccct
gatttcgcgcggcgcctgggcccggatcggccggttcgacgagcgctatgtgatcgaccacgtggacaccgactact
gcatgcgtgccctgggtcgcggcgtgccgctctacctgaatccgcacgtcgtgctgcggcaccagattggcgacatc
cgtgcccggtcgctgttcggctggaagatccacttcatcaactacccggccgcgcggcgctactacatcgcgcgcaa
tgccatcgatctctcgcggggcgcatgtgcgcgcctttcccgcgatcctgttcatcaacgtttacacgctcaagcaga
tcctgccgatgctgatgttcgagcgcgaccgcttcaagaagaccatcgcgctgatgctcggctgcttcgatggcctg
ttcgggcggctcgggggcctcggcgaggtgcatccgcggatgggcaaatacctgggccgcagcgattgaccgccacc
cttccagcgccgcgcgtacgccgcgccgcgctcgccttcatcttcgtcacggtgctgatcgacttcatggcgttcgg
cctgatcctgcccggcctgccgcacctggtggagcggctggccggcggcagcacggtaacggcggcgtactggatcg
ctgtgttcggcaccgcgttcgcggcgatccagttcgtgagctcgccgatccagggcgcgctgtccgaccgcttcggg
cggcggccggtgatcctgctgtcgtgcttcggcctcggcgtggatttcgtgttcatggccctggccgacagcctgcc
gtggctgttcgtcggccgggtggtctccggcgtgttctcggccagcttcaccatcgccaatgcctacatcgccgatg
tgacgctgccggaggagcgcgcccgcagctacggcatcgtgggggccgcgttcggcatgggcctggtgttcgggccg
gtgctcggcgggcaactgagccacatcgatccgcgcctgccgttctggttcgcggccggcttgacgctgctcagctt
ctgctacggatggttcgtgttgcccgaatcgctgccgcccgagcggcgtgcccgcaagttcgactggtcgcatgcca
atccggttgggacgctggtgctgctcaagcgctatccgcaggtgttcggactggcggcggtgatcttcctcgtgaac
ctggctcagtacgtctatccagcgtgttcgtgctgttcgccgactaccggtatcactggaaggaagacgccgtggg
ctgggtgctcggcgcggtgggcgtgctcagcgtgctggtcaatgcgctgttgatcgggccgggcgtgaagcgcttcg
gcgagcgccgcgccctgttgctcggcatggggcttcggcgtgctcggcttcgtcatcatcgggtttgccgacgctgga
tggatcctcctggccggggtgccgttcggcattctgctggcgttcgccggacggcggcgcaggcgctggtcacgct
gcaggtcggcaccgccgagcagggccgcatccaggggggcgctcaccagcctggtgtcggtcggcggcatcgtcgggc
cggcgatgttcgccggcagcttcggttacttcatcggcgcggacgcgccggtgcacttgccgggcgcgccgttttc
ctcgctgcggcgttcctctgcatcggcacgctgatcgcgtggcgctacgcacagccgaagcccgcgacggcagcggt
gcccgagccgacctga
```

Fig. 4 (Cont. 3)

```
SEQ ID NO 2
LENGTH: 3959
TYPE: DNA
ORGANISM: Variovorax paradoxus

SEQUENCE: 2
    1 CCGCTGCGCC TCGCAACGGG TTTGCTCCTT CGGTGCATCG CGATCCCTGC GGGTGCGATG
   61 GCTCTCCAGA CGGCGTTTGA TGTGATGCAG TACTGACCCC CTGTTCGGGC CGACCTGAGC
  121 GTTTATGGGA GTTTGCGCCT TCGGTAGGGC CACCGGGGTG GCCCGCTCTC CTGCAGTGGG
  181 GCGATTGTAG GTGGGCACTG CCAATGCGCC AACCCCGGGA GTTTCGGCCC TTGGGCCGAT
  241 GGGATAATCA TCCGTTCATT CGCCGGAGGG CGATCGTTCG ACAACAACAG GGGACCCCAT
  301 GATCCTGGTA ACCGGCGGCG CAGGCTTCAT TGGCGCCAAT TTCGTACTCG ACTGGCTCGC
  361 ACAGAGCGAT GAACCGGTCG TGAACCTAGA CAAGCTGACC TACGCGGGCA ACCTCGAGAC
  421 GCTCGCATCG CTCAAGGACA ACCCGAAGCA CATCTTCGTG CAGGGCGACA TCGGCGACAG
  481 CGCGCTGCTC GACCGCCTGC TGGCCGAGCA CAAGCCGCGT GCCGTGGTCA ACTTCGCGGC
  541 CGAATCGCAC GTCGACCGCT CGATCCACGG CCCCGAAGAC TTCGTGCAGA CCAACGTGCT
  601 GGGCACCTTC CGCCTGCTCG AATCCGTGCG CGGTTTCTGG AATGCCCTGC CGGCCGACCA
  661 GAAGGCCGCC TTCCGCTTCC TGCATGTGTC GACCGACGAG GTCTACGGCT CGCTCTCCAA
  721 GACCGACCCG GCCTTCACCG AAGAGAACAA GTACGAGCCC AACAGCCCGT ACTCGGCCAG
  781 CAAGGCCGCC AGCGACCACC TCGTGCGCGC CTGGCACCAC ACCTACGGCC TGCCGGTGGT
  841 CACCACCAAC TGCTCGAACA ACTACGGGCC GTTCCACTTC CCCGAGAAGC TCATTCCCCT
  901 GATGATCGTC AACGCGCTGG CGGGCAAGCC GCTGCCCGTG TACGGCGACG GCATGCAGGT
  961 GCGCGACTGG CTCTACGTGA AGGACCACTG CAGCGCCATC CGCCGCGTGC TCGAAGCCGG
 1021 CAAGCTCGGC GAGACCTACA ACGTGGGCGG CTGGAACGAG AAGCCCAACA TCGAGATCGT
 1081 CAACACCGTC TGCGCGCTGC TCGACGAGCT GAGCCCCAAG GCCGGCGGCA AGCCGTACAA
 1141 GGAACAGATC ACCTATGTGA CCGACCGCCC CGGCCACGAC CGCCGCTACG CGATCGACGC
 1201 ACGCAAGCTC GAGCGCGAAC TCGGCTGGAA ACTGCCGAG ACCTTCGACA GCGGCATCCG
 1261 CAAGACGGTC GAGTGGTACC TCGCGAACGG CGAGTGGGTG CGCAACGTGC AAAGCGGCGC
 1321 GTACCGCGAG TGGGTCGAGA AGCAATACGA CGCCGCACCG GCGAAGGCCA CCGCATGAAG
 1381 CTGCTGCTGC TGGGCAAGGG CGGACAGGTC GGCTGGGAGC TGCAACGCAG CCTCGCGCCC
 1441 CTGGGCGAAC TGGTGGCGCT CGATTTCGAC AGCACCGACT TCAACGCCGA CTTCAGTCGC
 1501 CCCGAGCAGC TGGCCGAGAC AGTGCTGAAG GTGCGCCCCG ACGTCATCGT CAATGCCGCA
 1561 GCGCACACCG CGGTCGACAA GGCCGAGAGC GAGCCCGAGT CGCGCGCAA GCTCAACGCC
 1621 ACCTCGCCCG CGTGGTGGC CGAAGCCGCG CAGCAGATCG GCGCGCTGAT GGTTCACTAC
 1681 TCGACCGACT ACGTCTTCGA CGGCAGCGGC AGCAAGCCGT GGAAAGAAGA CGATGCGACC
 1741 GGCCCGCTCA GCGTCTACGG CAGCACCAAG CTCGAAGGCG AGCAACTGGT GGCAAAGCAC
 1801 TGTGCGAAGC ACCTGATCTT CGCACCAGC TGGGTCTATG CCGCGCGCGG CGGCAACTTC
 1861 GCCAAGACCA TGCTGCGCAT CGCCAAGGAG CGCGACAAGC TGACCGTCAT CGACGACCAG
 1921 TTCGGCGCGC CCACCGGCGC GGAACTGCTG GCCGACATCA CCGCGCACGC GATTCGCGCG
 1981 ACCTGCAGG ACCCGTCCAA GGCCGGCTC TATCACGCGG TGCCGGTGG CGTGACCACG
 2041 TGGCACGGCT ATGCGCGCTT CGTGATCGAG CAGGCCAAGG CGGCGGGCGT GGAACTGAAG
 2101 GCCGGCCCCG AAGCGGTCGA GCCCGTGCCC ACCACGGCAT TCCCGACGCC GGCCAGGCGG
 2161 CCGCACAACT CGCGCCTGGA CACCACCAAG CTGCAATCGA CCTTCGGCCT CGTGCTGCCC
 2221 GAGTGGCAGT CCGGCGTCGC CCGCATGTTG CGCGAAACCT TCTGATATTC GCAGAGCAAG
 2281 AGAGACACGA ACACCCCATG ACCAAGACGA CGCAACGCAA AGGCATCATC CTCGCCGGTG
 2341 GCTCGGGCAC CCGCCTGCAC CCCGCGACGC TTGCCATGAG CAAACAACTG CTGCCGGTGT
 2401 ACGACAAGCC GATGATCTAT TACCCGCTGA GCACGCTGAT GCTGGGCGGC ATGCGCGACA
 2461 TCCTGATCAT CAGCACGCCG CAGGACACGC CGCGTTTCCA GCAACTGCTG GGGGATGGCA
```

Fig. 5

2521 GCCAATGGGG CATCAACCTG CAGTACGCGG TGCAGCCGAG CCCGGATGGT CTGGCGCAGG
2581 CGTTCATCAT CGGTGACAAG TTCGTGGGCA ACGACCCGAG TGCGCTGGTG CTGGGGGACA
2641 ACATCTTCTA TGGCCACGAC TTCGCCCATC TGCTGGCCGA TGCCGACGCC AAGACCTCGG
2701 GTGCGACGGT GTTCGCCTAC CACGTGCACG ACCCCGAGCG CTACGGCGTG GTGGCCTTCG
2761 ATGCCAAGGG CAGGGCGAGC AGCATCGAAG AAAAGCCGCT CAAGCCCAAG AGCAGCTATG
2821 CGGTCACGGG CCTCTACTTC TACGACAACC AGGTCGTCGA CATCGCCAAG GCCGTGAAGC
2881 CGAGCGCGCG CGGCGAACTC GAGATCACCG CGGTCAACCA GGCGTATCTC GACCTCGACC
2941 AGCTGAACGT GCAGATCATG CAGCGCGGCT ATGCGTGGCT CGATACCGGT ACGCACGACA
3001 GCCTGCTGGA AGCCGGGCAG TTCATTGCCA CGCTCGAGCA CCGCCAGGGG CTGAAGATCG
3061 CATGCCCCGA AGAGATCGCA TGGCGCAATG GCTTCATCTC AACCGAGCAA CTCGAAAAGC
3121 TCGCGGCGCC GCTGGAAAAG AGCGGCTACG CAAGTACCT CAAGCACCTG CTGAACGACG
3181 AGGTGCGCTC GTGAAGGCCA CGCCCACCTC GATTCCTGAC GTGCTCGTGA TCGAGCCGAA
3241 GGTGTTTGGC GATGCACGGG GCTTCTTCTT CGAAAGCTTC AACCAGAAGG CCTTCGACGA
3301 AGCGATCGGC AAGCATGTCG ACTTCGTGCA GGACAACCAT TCGCGATCGG CCAAGGGTGT
3361 GCTGCGGGGG CTGCATTACC AGGTCCAGCA GCCGCAAGGC AAGCTCGTGC GGGTGGTGCG
3421 TGGTGCGGTG TTCGACGTGG CCGTCGACAT CCGCAAGTCG TCGCCGACTT TGGCAAATG
3481 GGTGGGTGTC GAGTTGAACG AAGACAACCA CAAGCAGCTC TGGGTGCCGG CAGGATTCGC
3541 GCACGGTTTC CTGGTGTTGA GCGAGACCGC GGAATTCCTC TACAAGACCA CCGACTACTA
3601 CGCGCCCGCC CACGAGCGCG CGATTGTCTG GAACGACCCC GCTGTCGGTA TTCGATGGCC
3661 GGATGTGGGA GGGGCACCGG TCCTGTCGAA GAAGGACGAA GACGGGTGTC TTCTGCAAGC
3721 GGCAGAGGTT TTCTAGTGTC CTTTCGTCAG ATAGCGGGGC GGCTTCGCGT ATCGGGATCC
3781 CGCGTTGAGC CCGCAAGAGT GCCCTGAGAG GGGGGGCGAA AAACTCACAA CGCCACTGCC
3841 TCGAGCAAAC GTGCGTCTCG CAGCTTTCTG AAGTTGTTGC ACCTTCTTTT TTTTCTCTT
3901 ACATCTTTGA AATGATTTTG AAAATCCGCG GCGATCGCAT GCATGCTGCT GGAATCACC

Fig. 5 (Cont.)

SEQ ID NO 3
LENGTH: 915
TYPE: DNA
ORGANISM: Variovorax paradoxus

SEQUENCE: 3
    1 ATGAATGGCA TGCATATCGA CTCGGTCGAC CTCAATCTGC TGCGCCTGTT CGATGCGGTC
   61 TACCGCGAGC GCAGCGTGAG CCGCGCCGCG GAGTCGCTGG CCTCACGCA GCCTGCGGCA
  121 AGCCATGGGC TGGGACGGCT GCGGCTGCTT TTGAAAGACG CGCTCTTCAC GCGTGCCCCC
  181 GGCGGCGTGG CGCCCACGCC GCGCGCCGAC CGGCTCGCGG TGGCGGTGCA GGCGGCGCTC
  241 GGCACGATCG AAGCGGCGCT GCACGAGCCC GATCGCTTCG AGCCCCAGGT GTCGCGCAAG
  301 AGCTTCGTA TTCACATGAG CGACATCGGC GAGGGCGCT TCCTGCCCGC GCTGATGGCG
  361 CGGCTCGGCG AGCTGGCGCC CGGCGTGCGG CTGGAGACCC TGCCGCTCTT GCCTGCGGAG
  421 GTTGCGCCCG CACTCGACAG CGGCCGCATC GATTTCGCCT CGGCTTTCT CTCGACCGTG
  481 CGCGACACGC AGCGCACGCA TCTTCTGAAA GACCGCTACA TCGTGCTGCT GCGCAAGGGC
  541 CATCCCTTTG TGAAGCGCCG GCGCAAGGGG CAGGCGCTGC TCGAGGCGCT GCAGGAGCTC
  601 GACTACGTGG CGGTGCGCAC GCACGCCGAC ACGCTGCGCA TCTTGCAGTT GCTCAACCTC
  661 GAAGACCGCC TGCGCCTCAC GACCGAGCAC TTCATGGTGC TACCGGCCAT CGTGCGCGCC
  721 ACCGATCTCG CGGTGGTGAT GCCGCGCAAC ATCGCGCGAG GGTTTGCGGA GGAGGGCGGC
  781 TACGCGATCG TCGAGCCGCC GTTCCGCTG CGCGATTTCA GCGTGTCGCT GCACTGGAGC
  841 AAGCGCTTCG AGGGCGACCC GGCCAACCGT TGGTTGCGGC AGGTGATCAC GGCGCTGTTC
  901 TCCGAGCGCG GCTGA

Fig. 6

SEQ ID NO 5
LENGTH: 7476
TYPE: DNA
ORGANISM: Variovorax paradoxus

SEQUENCE: 5
```
   1 ATGAGTACCG TCGATCAGCT GGGCCGCACC GCCCCCCTTA CCTCGGGGCA GATGGCGATG
  61 TGGCTCGGCG CAAAGTTCGC GTCGCCGAC ACCAATTTCA ATCTCGCCGA AGCCATCGAC
 121 ATCGCAGGCG AGATCGACCC CGCGATCTTC CTGGCGGCCA TGCCACAGGT GGCCGATGAA
 181 GTCGAGGCCA CGCGCCTGAG CTTCATCGAT ACCCCGCAAG GGCCACGACA GGTCGTCGCG
 241 CCCGTTTTCA CCGGCGAGAT CCCCTACCTC GACCTCAGCG GCGAGAGCGA TCCGCAGGCC
 301 GAGGCCGAGC GCTGGATGCA TGCGGACTAC ACCCGCAGCA TCGACCTCGC GCACGGGCAG
 361 CTGTGGCTGT CCGCGCTGAT CCGCCTCGCG CCCGATCGCC ACATCTGGTA CCACCGCAGC
 421 CATCACATCG CGCTCGACGG CTTCAGCGGC GGCCTCATCG CACGCCGCTT CGCCGACATC
 481 TACACCGCGA TGGTCGACAA CAACGCAGCG GTGCCCGAAG ACTCGCGCCT TGCACCGATC
 541 TCGCAGCTGG CCGACGAAGA ACATGCCTAT CGCGAGTCCG GCCGCTTCCC GCGCGACCGC
 601 CAGTACTGGA CCGAGCGCTT CGCCGATGCA CCCGATCCGT TGAGCCTCGC CTCGCACCGC
 661 TCGGTCAACG TCGGTGGCCT CTTGCGCCAG ACGGTGCACC TGCCGGCGGC CAGCGTGCAA
 721 GCCCTGCAGA CCATCGCGCA AGAGCTCGGC ACCACGCTGC CGCAAATCCT CATCGCCACC
 781 ACCGCGGCCT ACCTGTACCG CGCAACGGGC ATCGAGGACA TGGCAATCGG CATCCCCGTC
 841 ACCGCGCGCC ACAACGACCG CATGCGCCGC GTGCCCGCGA TGGTGGCCAA CGCGCTGCCG
 901 CTGCGCCTGG CGATGCGCGC GGACCTGCCG ATTCCGGAAC TGATCCGCGA AGTCGGCCGG
 961 CAGATGCGGC AGATCCTGCG GCACCAGTCG TATCGCTACG AGCATTTGCG CAGCGACCTC
1021 AACATGCTGG TGAACAACCG GCAGCTCTTC ACCACCGTGG TCAACGTCGA GCCCTTCGAC
1081 TACGACTTCC GCTTTGCGGG CCATGCCGCG AAGCCGCGCA ACCTCTCGAA CGGCACGGCC
1141 GAGGACCTCG GCATCTTCCT GTACGAGCGC GGCAACGGGC AGGACCTGCA GATCGACTTC
1201 GACGCCAACC CCGCGGTGCA CACCGCAGAG GAACTGGCCG ATCACCAGCG CCGGCTGCTT
1261 GCCTTCATCG ACGCCGTGAT CCGCCTGCCG TTGCAGGCCG TCGGCCAGAT CGACCTGCTC
1321 GGTGCCGAAG AGCGGCAGCA ATTGCTGGTC GAGTGGAACG ACACGGCCCA CGCCGTGCCC
1381 GACACCCATC TCACCGCGTT GATCGAAGCG CAGCTCGCAG CCGATCCGCA AGCCATCGCA
1441 TTGCGCTTCG ACGGCGAGGC GATGAACAAC GAAGAACTGA ACCGCCGCGC CAACCGTCTC
1501 GCCCACCTGC TGCGCGCACG CGGCGCTGGC CCGGAGCGCA CCGTGGCGCT CGCGATCCCG
1561 CGTTCGATGG ACCTGATGAT TGCCTTGCTC GCCACGTTGA AGACCGGCGC GGCCTACCTG
1621 CCGGTCGATC CGGATTTCCC GGCGGACCGC ATCGCCTTCA TGCTCGGCGA TGCGCAGCCC
1681 GTGTGCCTCG TCACGACCGA AGCCCTCGCG GAGTCGCTGC CGGCAGCCGC CCCCACATTG
1741 CTGCTCGATG TAGCGCAAAC GATTGCGGAT CTGGAGAGTT GCAACGACAC CAACCCGGGC
1801 ATCGCGATCG ACCCTTCGCA TCCGGCCTAT GTGATCTACA CCTCGGGCTC GACCGGCATG
1861 CCCAAGGGTG CGGTCGTGTC GCACCGCGCC ATCGTCAACC GCCTGCGCTG GATGCAGGAC
1921 CGCTACGGCC TTCAGGCCGA CGACCGCGTG CTGCAGAAGA CGCCTTCCAG CTTCGACGTG
1981 TCGGTGTGGG AGTTCTTCTG GCCGCTGATC GACGGTGCCA CGCTCGTGCT TGCGAAACCG
2041 GGCGGCCACA AGGATGCGGC CTACCGCGGG GGCTGATCG CGGAGGAGGG CATCACCACG
2101 ATCCACTTCG TGCCGTCGAT GCTCGAGGTC TTCCTGCTCG AGCCCACGGC GGGCGCATGC
2161 ACCACGCTGC GCCGCGTGAT CTGCAGCGGC GAAGCCTTGT CGCCCGCGCT GCAATCGCAG
2221 TTCCAGCAGC ACCTCTCGTG CGAGCTGCAC AACCTCTACG GTCCGACCGA GGCCGCGGTC
2281 GACGTCACCT CGTGGGAGTG CGAACGCACG GACGACGCAG AAGCCTCGAG CGTTCCCATC
2341 GGCCGCCCGA TCTGGAACAC CCAGATGCAC GTGCTCGACA GCGGCCTGCA GCCCGTGCCG
2401 GCCGGCGTGA CTGGCGAGCT GTACATCGCG GGCGTCGGCC TCGCACGCGG CTACCTCAAG
2461 CGCCCGTTGC TGAGCGCCGA GCGTTTCATC GCCAACCCCT ACGGCACACC CGGCAGCCGC
2521 ATGTACCGCA CCGGCGACCT CGCGCGCTGG CGCAAGGACG GCAGCCTTGA CTTCCTCGGC
2581 CGCGCCGACC AGCAGGTGAA GATCCGGGGC CTGCGCATCG AGCGGGAGA GATCGAATCC
2641 GTGCTGCTGC AGCATCCGCA AGTCGCGCAG GCCGCCGTGG TGGCGCGCGA AGACGTACCG
2701 GGCGAAAAGC GTCTCGTGGC CTACGTCGTT GCGACGGACG CTGCCGATCC GCAAGCGGCC
2761 GAACTGCGCA CGCGCCTCGC GCAATCGCTG CCCGAGTACA TGGTGCCTTC GGCCTTCGTC
```

Fig. 7

```
2821  AGCCTCCCGT CGCTGCCGCT CGGACCCAGC GGCAAGCTCG ACCGCAAGGC GCTGCCGCCC
2881  CCCGAAGTGC AGGCCGCCAC GCCGTACGCC GCGCCGCGCA CGCCGACCGA AAAGATCCTG
2941  GCCGGCCTCT GGGCCGAGAC GCTGCATTTG CCGCGCGTCG GTGTCAACGA CAACTTCTTC
3001  GAACTCGGCG CCACTCGCT GATGATCGTG CAGCTCATGT CGATGATCCG GCAGCAATTC
3061  ATGATCGACC TGCCGGTCGA CACGCTGTTC CAGGTCTCCA CCATCGCGGG CCTTGCCGAG
3121  CTGCTCGACC AGGAATCGGT CGCCCGTCCG AGCCTGACTC CGATGCCGCG CCCCGCGCGC
3181  ATTCCGCTGT CCTTCGCGCA GCGCCGCCTG TGGCTGATGA ACCAGCTCGA AGGCGCGAAC
3241  CCGGCCTACA ACATGCCGCT CGCGCTGCGC CTGTCGGGTG TGCTCGATCG CACCGCATTG
3301  CATGCGGCGC TCGGCGACCT GGTGCAGCGC CACGAGAGCC TGCGCACGGT CTACCCGAAC
3361  GAAGACGGGC TGCCGTACCA GCACATCCTC GACGGCGCGG ATGCGCGTCC GGCGGTGATC
3421  GAGGCCGACA CCAGCGAAGA AGAAATCGCG GCGCAGCTTC ACGCCGCTGC GGGCCATGCC
3481  TTCGATCTCG GCAGCGCGGC GCCCTTGCGC GTCTACCTGT TCAAGCTCGC CGGCGACGAA
3541  CACGTGCTGC TGCTGCTCAC GCACCACATT GCCGGCGATG GCGCCTCGCT GCTGCCGCTA
3601  GCGCGCGACA TCAGCGTGGC CTATGCCGCG CGCTGCGAAG GCAAGGCGCC GGGCTGGGAG
3661  CCGCTGCCGC TGCAATACGC CGACTACGCG CTGTGGCAGC AGGAGCTGCT CGGCAGCGAA
3721  GACGATGCCG AGAGCATGGC CGGCCGCCAG CGTGAGTTCT GGCGTTCCTC GCTGAGCGAC
3781  CTGCCCGAGC AACTGGCGCT GCCCGTCGAC CACGCACGGC CGCTCGTGCC GACCTACCGC
3841  GGCGATGTGG TCCCGCTGCA GATTCCGTCG CATGTGCATG AACGCATCCT GCAACTGGCG
3901  CGCGACGGGC AGGCCAGCGT CTTCATGGTG CTGCAGGCCG CACTCGCGGG CCTCCTGAGC
3961  CGCCTCGGCG CGGGCGACGA CATCGTCATC GGCAGCCCGG TCGCGGGGCG CAGCGACCAT
4021  GCGCTGGACG AACTCATCGG CTGCTTCGTC AACACGCTGG TGCTGCGCAC TGACACCTCG
4081  GGCCAGCCGA GCCTGCGCGA GCTGGTCTCG CGCGTGCGCG CCACCAACCT CGCGGCCTAT
4141  GCGAACCAGG AGTTTCCGTA CGACCGCCTC GTGGAGCTGC TGCGTCCGGG CCGCTCGCGC
4201  GCCAACCTGC CGCTGTTCCA GGTCATGCTG GGCTTCCAGG GCACGAGCCG CCTGTCGTTC
4261  AGCCTGCCGG GCCTGTCGAT CGCGCCGCAG CCGGTGGCCA TCGACACCGC GAAGTTCGAC
4321  CTGTCGTTCA TCCTCGGCGA GCAACGCGGT GCCGATGGCC TGCCGGGCGG CATCTCCGGC
4381  GGCATCCAGT ACAGCACCGA CCTGTTCGAG CGCAGCACGG TCGAGGCCAT GGGCGCGCGG
4441  CTGGTGCGTT TGCTGGAAGA GGCCTGCGAG GCGCCCGACG ATGCGGTGAG TGGCCTCGCC
4501  ATCCTGAGCG CGGAAGAAAC CGACCGCCTG CTGTCCGACT GGAGCGGCC CACGCGCGAC
4561  CTTGCGCCGC TCTCGTTCGC CGACATGGTG CCCTCGCATG CCGCGGAGCG CCCGCTTGCA
4621  GATGCAGTGG TGCTCGACGA CGCGACCGTC AGCTACGCCG AACTCGATGC ACGCGCCAAC
4681  CGGCTCTCGC ACCTGCTGCG TGCGCAAGGC ATCGGGGTTG GCGCCATCGT CGCGACAGTG
4741  CTGCCGCGTT CGCTCGACCT CATCGTGGCG CACTTGGCCA TCGTGAAGGC CGGCGCGGCC
4801  TACCTGCCCA TCGACCCCAA CCACATGGCG GCGCGCAGCG CCTTCGTGTT CGAGGAGGCC
4861  GCGCCCGCCG CGGTGCTGAC GCACGATGCG CTGTTGCCCG AGCTGGTCGG CGTTCCCCGC
4921  TGCATCGCGC TCGACAGCGA CAGCATGGTT GCCGCGCTGG CCATCCAGTC GGATACGCCG
4981  CTGGTGCATG CGGCCAATCC ACAGGATGCC GCCTACCTCA TCTACACCTC CGGCTCCACC
5041  GGCATGCCCA AGGGCGTGGT GGTGCCGCAT GCGGGCCTGG GCAGCCTCGG CACCGCGATG
5101  GCGGAGCGGC TCGTCATCGG CCACGGCTCG CGCGTGCTGC AGTTCTCCTC CAGCGGCTTC
5161  GACGCGTCGG TGATGGACCA GCTGATGGCC TTTGGCGCCG GTGCCGCGCT GGTGGTGCCG
5221  GGGCCGGAGC AACTGCTCGG CACGGAGCTG GCCGATCTGC TCGAGAAGCA GGCCGTGAGC
5281  CACGCGCTGA TTCCGCCCGC CGCGCTCGCG ACCCTGCCGC ACGGCGAGTT CCCGCACCTG
5341  CAGACGCTGG TGGTCGGCGG CGATGCCTGC ACCGCCGCG TGGCGGCGAA GTGGTCGCAA
5401  GGCCGCCGCA TGATCAACGC CTACGGCCCG ACCGAGATCA CCATCTGCGC GAGCATGAGC
5461  GCGCCGATGA CGGCCGAGGA GTTGCCCTCC ATCGGCCAGC CGATCTGGAA CACGCGGATG
5521  TATGTGCTCG ACAGCGCCCT GCAACCGGTG CCGCCGGGTG TCGCGGGCGA GCTCTACATC
5581  GCCGGCAGCG GCGTGGCGCG CGGCTATCTC AACCGGCCGG CATTGAGTGC GGAACGCTTC
5641  ATCGCCGACC CGCATGGCGC GCCCGGCAGC CGCATGTACC GCAGCGGCGA CCTCGCACGC
5701  TGGCGCGCCG ACGGCACGCT CGACTTCCTC GGCCGCGCCG ACCAGCAGGT GAAGATCCGG
5761  GGCTTCCGCA TCGAGCCGGG CGAGATCGAA TCCGTGCTGC TCAAGCACCC GTTGATCACG
5821  CAGGCCGCCG TGATCGCCCG CGAGGACGTG CCCGGCGAGA AGCGCCTGGT CGCCTACTTC
5881  GTCGCCGGTT CCGAGCCGCA GCCCACCGAG CTGCGCGCCC ACATGGCGCA GGCCTTGCCC
5941  GACTACATGG TGCCTTCGGC CTTCGTGCGC CTGCCGTCGC TGCCGCTCAC GCAAAGCGGC
6001  AAGCTCGACA AGAAGGCGCT GCCGGTGCCC GACCAGCAGC CCGCCGCGCT GTACGTGGAG
6061  CCCCGCACGC CGACCGAGAA ACTGCTCGCG GGCCTCTGGT CCGAGACGCT GCACCTGGAG
6121  CGTGTCGGCA TCCACGACAA CTTCTTCGAG ATCGGCGGGC ATTCGCTCAT GGCGATCCAG
6181  CTGGGCATGC GCATCCGCCA GCAGGTGCGC GCGGACTTCC CGCACGCCGA GGTCTACAAC
```

Fig. 7 (Cont. 1)

```
6241  CGCCCGACGA TTGCCGACCT GGCCGCCTGG CTCGACAACG AAGGCGGCAC GGTCGAGGCG
6301  CTGGACCTGT CGCGCGAGCT CGACCTGCCC GCGCACATCC GCCCGCAGGC CACTGCACCG
6361  AAGCTCGCAC CGCGCCGCGT GTTCCTCACC GGCGCGAGCG GCTTCGTCGG CAGTCACCTG
6421  CTGGCCGCGC TGTTGCGCGA CACCGCGGCC TGCGTGGTCT GCCACGTGCG CGCGCCCGAC
6481  GAGCAGGCCG GCGAGCAGCG CCTCAAGCGC ACGCTGGCCC AGCGCCAGCT CGGTGCGATC
6541  TGGGACAACG CGCGCATCAA GGTCGTGACC GGCGACCTCG GCAAGCCGCG CCTGGGCCTC
6601  GATGACGCTG CCGTGCAACT GGTGCGCGAC GGCTGCGACG CCATCTACCA CTGCGCCGCG
6661  CAGGTCGACT TCCTGCATCC CTACGCGAGC CTCAAGCCCG CGAACGTCGA CAGCGTGGTC
6721  ACGCTGCTCG AATGGACGGC GCAGGGCGC GCGAAGAGCA TGCACTACGT CTCCACGCTG
6781  GCTGTGATCG ACCAGAACAA CAAGGAAGAC ACCATCACCG AGCAATCGGC GCTGGCCTCA
6841  TGGAGCGGGC TGGTCGACGG CTACAGCCAG AGCAAGTGGG TCGGCGATGC GCTGGCCCGC
6901  GAGGCGCAGG CGCGCGGCAT GCCGGTGGCG ATCTACCGGC TGGGGGCAGT CACCGGCGAC
6961  CACACGCACG CGATCTGCAA TGCCGACGAC CTGATCTGGC GCGTGGGCGCA TCTCTATGCC
7021  GACCTGGAAG CGATTCCCGA TATGGACCTG CCGCTCAACC TCACACCGGT GGACGACGTG
7081  GCGCGCGCCA TCCTCGGCCT TGCGGCGCAG GAGGCCTCGT GGGGCCAGGT GTTCCACCTG
7141  ATGAGCCAGG CGGCGCTGCG GGTGCGCGAC ATTCCGCACG TCTTCGAGCG CATGGGCATG
7201  CGGCTGGAGC CGGTCGGGCT GGAGCCCTGG CTGCAGCGCG CGCATGCACG GCTGGCCGTC
7261  GCGCATGACC GCGACCTGGC CGCGGTGCTC GCCATCCTCG ACCGCTACGA CACCACGGCC
7321  ACGCCGCCGC AGGTGAGCGG CGCGGCCACG CATGCGCAGC TCGAGGCCAT CGGCGCGCCG
7381  ATCCGCCCGG TGGACCGCGA CCTGCTGCAG CGCTACTTCG TCGACCTGGG CATCGACACC
7441  AAGGCGCGCC GCGCCCTGGA AACCACCACT TCATAG
```

Fig. 7 (Cont. 2)

```
SEQ ID NO 7
LENGTH: 1326
TYPE: DNA
ORGANISM: Variovorax paradoxus

SEQUENCE: 7
   1  ATGGCACGCT ATCTCATCGC AGCAACCGCC TTGCCGGGAC ACGTCCTGCC GATGCTGGCC
  61  ATCGCGCAGC ATCTGGTGAA CCAGGGGCAC GAGGTGCGGG TGCACACCGC GAGCCAGTTC
 121  AGGGCGCAGG CCGAGGCGAC CGGTGCGGGC TTCACGCCCT TCGAGCGCAC GATCGACTTC
 181  GACTACCGCG ACCTGGACAA GGCGTTTCCC GAGCGCCAGC GCATCGCCTC GGCGCATGCG
 241  CAGCTGTGCT TCGGCCTGAA GCACTTCTTT GCCGATGCGA TGGCCGCGCA GCATGCGGGC
 301  CTGCAATCGA TCCTCGAAGA CTTCGAGGCC GATGCCATCG TGGTCGACAC GATGTTCTGC
 361  GGCACTTTCC CGCTGCTGCT AGGCAAGGAG CGCGAAGACC GCCCGGCCAT CGTCGGCATC
 421  GGCATCTCGG CGCTGCCGCT CTCGAGCTGC GACACCGCCT CTTCGGCAC CGCGCTGCCG
 481  CCGTCGTCCA CGCCGGAAGG GCGGGTGCGC AACAAGGCGA TGAACGCCAA CCTCAAACAG
 541  GCGATGTTCG GCGAGGTGCA ACGCTACTTC GACACGCTGC TCGCGCGTTC GGGCCTGGCC
 601  GCGCTGCCCG ATTTCTTCGT CGATGCGATG GTGAAGCTGC CCGATCTTTA CCTGCAGCTC
 661  ACCGCGCCTT CGTTCGAATA CCCGCGCAGC GACCTGCCCG CGTCGGTGCA TTTCGTCGGC
 721  CCGCTGCTCT CGCCCGCGAG CCGCGACTTC ACGCCGCCCG AGTGGTGGCA CGAGCTGGAC
 781  GACGGCCGCT CGGTCGTGCT GGTCACGCAG GGCACGCTGG CCAACCAGAA TCCGTCGCAG
 841  CTGATCGGCC CGACGCTGCA GGCGCTGGCC GGCGACAAGA ACATCCTCGT CATCGCCACC
 901  ACCGGCGGCC CGGTGCCGCC CGCCCTGACG GTGAACCTGC CGCCAACGC CCGCGTGGTG
 961  CCGTTCCTGC CCTACGACCG GCTGCTGCCC AAGCTGCACG CGATGGTCAC CAACGGCGGC
1021  TACGGCTCGG TCAACCATGC ATTGAGCCTC GGTGTGCCGG TGGTGGTGGC GGCACCTCC
1081  GAAGAGAAGC CCGAGATCGC CGCGCGTGG GCCTGGTCGG GCGCGGGCAT CAACCTCGCG
1141  ACCGGCCAGC CGACCGCGCG CCAGGTCGGC GACGCGGTGC GCAAGGTACT GGGCAACTCG
1201  ACCTATCGCC AGCGTGCGGC GGTGCTGCGT GAGGACTTCG CTTGCCATCG CGCGCTGACC
1261  GGCATCGCCG GCGCCCTCGA GGCACTTCTG CAAACCTTCG CATCCGCGGA AATGGCTTGA
```

Fig. 8

SEQ ID NO 9
LENGTH: 213
TYPE: DNA
ORGANISM: Variovorax paradoxus

SEQUENCE: 9
      1 ATGAGCAACC CGTTCGACGA CAAGAACGCC AGCTTCCAGG TGCTGGTGAA CGACGAGGGC
     61 CAGCACTCGC TGTGGCCCGC CTTCATCGCC GTGCCCGCCG GCTGGCAGGT GGCGCTGGCG
    121 CCGACCGACC GCGACGCCTG CAGCGCCTAC ATCGCGGCGA ACTGGCAGGA CATGCGCCCG
    181 CGTTCGCTGG TGGTGGCCAC GGCGGCCGGC TGA

Fig. 9

SEQ ID NO 11
LENGTH: 969
TYPE: DNA
ORGANISM: Variovorax paradoxus

SEQUENCE: 11
      1 ATGTCCTTCC CGTTCGGTGC CGTCGTCGTC ACCTATTTCC CGACCGGCGA GCAAGTGGCG
     61 AACCTCCATT CGCTGGCGGC CTCGTGTCCG CACCTCTGCG TGGTCGACAA CACGCCGCAG
    121 GTGGGCGATT GGCATGCGGC GCTCGTCGAT GCGGGCGTTT CGGTGCTGCA CAACGGCAAC
    181 CGCGGCGGCA TCGCGGGCGC CTTCAACCGC GGCATCATCG ACCTCGAAGC GCGGGGCGCC
    241 GAACTCTTCT TCCTGCTCGA CCAGGATTCG AAGCTGCCAC CCGGCTACTT CGATGCCATG
    301 TGCGAGGCTG CGATGGTGGC CCGGGAGCGG AAGGGCGAGG GCAATGGTGA GGAAGACGCG
    361 GCCTTCCTGA TCGGCCCGCT CGTCCACGAC ACGAACCTGG ACGCGCTGAT CCCGCAATTC
    421 GGCCTCCAGG GCAAACGCGT CTACCAGTTC GACCTGCGGC AGCCCTTCAC CGAGCCGCTG
    481 ATGCGCTGCG CCTTCATGAT TCCTCGGGC TCCCTGATTT CGCGCGGCGC CTGGGCCCGG
    541 ATCGGCCGGT TCGACGAGCG CTATGTGATC GACCACGTGG ACACCGACTA CTGCATGCGT
    601 GCCCTGGGTC GCGGCGTGCC GCTCTACCTG AATCCGCACG TCGTGCTGCG GCACCAGATT
    661 GGCGACATCC GTGCCCGGTC GCTGTTCGGC TGGAAGATCC ACTTCATCAA CTACCCGGCC
    721 GCGCGGCGCT ACTACATCGC GCGCAATGCC ATCGATCTCT CGCGGGCGCA TGTGCGCGCC
    781 TTTCCCGCGA TCCTGTTCAT CAACGTTTAC ACGCTCAAGC AGATCCTGCC GATGCTGATG
    841 TTCGAGCGCG ACCGCTTCAA GAAGACCATC GCGCTGATGC TCGGCTGCTT CGATGGCCTG
    901 TTCGGGCGGC TCGGGGGCCT CGGCGAGGTG CATCCGCGGA TGGGCAAATA CCTGGGCCGC
    961 AGCGATTGA

Fig. 10

SEQ ID NO 13
LENGTH: 1260
TYPE: DNA
ORGANISM: Variovorax paradoxus

SEQUENCE: 13
```
   1   TTGACCGCCA CCCTTCCAGC GCCGCGCGTA CGCCGCGCCG CGCTCGCCTT CATCTTCGTC
  61   ACGGTGCTGA TCGACTTCAT GGCGTTCGGC CTGATCCTGC CCGGCCTGCC GCACCTGGTG
 121   GAGCGGCTGG CCGGCGGCAG CACGGTAACG GCGGCGTACT GGATCGCTGT GTTCGGCACC
 181   GCGTTCGCGG CGATCCAGTT CGTGAGCTCG CCGATCCAGG GCGCGCTGTC CGACCGCTTC
 241   GGGCGGCGGC CGGTGATCCT GCTGTCGTGC TTCGGCCTCG GCGTGGATTT CGTGTTCATG
 301   GCCCTGGCCG ACAGCCTGCC GTGGCTGTTC GTCGGCCGGG TGGTCTCCGG CGTGTTCTCG
 361   GCCAGCTTCA CCATCGCCAA TGCCTACATC GCCGATGTGA CGCTGCCGGA GGAGCGCGCC
 421   CGCAGCTACG GCATCGTGGG GGCCGCGTTC GGCATGGGCC TGGTGTTCGG GCCGGTGCTC
 481   GGCGGGCAAC TGAGCCACAT CGATCCGCGC CTGCCGTTCT GGTTCGCGGC CGGCTTGACG
 541   CTGCTCAGCT TCTGCTACGG ATGGTTCGTG TTGCCCGAAT CGCTGCCGCC CGAGCGGCGT
 601   GCCCGCAAGT TCGACTGGTC GCATGCCAAT CCGGTTGGGA CGCTGGTGCT GCTCAAGCGC
 661   TATCCGCAGG TGTTCGGACT GGCGGCGGTG ATCTTCCTCG TGAACCTGGC TCAGTACGTC
 721   TATCCCAGCG TGTTCGTGCT GTTCGCCGAC TACCGGTATC ACTGGAAGGA AGACGCCGTG
 781   GGCTGGGTGC TCGGCGCGGT GGGCGTGCTC AGCGTGCTGG TCAATGCGCT GTTGATCGGG
 841   CCGGGCGTGA AGCGCTTCGG CGAGCGCCGC GCCCTGTTGC TCGGCATGGG CTTCGGCGTG
 901   CTCGGCTTCG TCATCATCGG GTTTGCCGAC GCTGGATGGA TCCTCCTGGC CGGGGTGCCG
 961   TTCGGCATTC TGCTGGCGTT CGCCGGACCG GCGGCGCAGG CGCTGGTCAC GCTGCAGGTC
1021   GGCACCGCCG AGCAGGGCCG CATCCAGGGG CGCTCACCA GCCTGGTGTC GGTGGCGGGC
1081   ATCGTCGGGC CGGCGATGTT CGCCGGCAGC TTCGGTTACT TCATCGGCGC GGACGCGCCG
1141   GTGCACTTGC CGGGCGCGCC GTTTTTCCTC GCTGCGGCGT TCCTCTGCAT CGGCACGCTG
1201   ATCGCGTGGC GCTACGCACA GCCGAAGCCC GCGACGGCAG CGGTGCCCGA GCCGACCTGA
```

Fig. 11

```
SEQ ID NO 15
LENGTH: 1080
TYPE: DNA
ORGANISM: Variovorax paradoxus

SEQUENCE: 15
     1  ATGATCCTGG TAACCGGCGG CGCAGGCTTC ATTGGCGCCA ATTTCGTACT CGACTGGCTC
    61  GCACAGAGCG ATGAACCGGT CGTGAACCTA GACAAGCTGA CCTACGCGGG CAACCTCGAG
   121  ACGCTCGCAT CGCTCAAGGA CAACCCGAAG CACATCTTCG TGCAGGGCGA CATCGGCGAC
   181  AGCGCGCTGC TCGACCGCCT GCTGGCCGAG CACAAGCCGC GTGCCGTGGT CAACTTCGCG
   241  GCCGAATCGC ACGTCGACCG CTCGATCCAC GGCCCCGAAG ACTTCGTGCA GACCAACGTG
   301  CTGGGCACCT TCCGCCTGCT CGAATCCGTG CGCGGTTTCT GGAATGCCCT GCCGGCCGAC
   361  CAGAAGGCCG CCTTCCGCTT CCTGCATGTG TCGACCGACG AGGTCTACGG CTCGCTCTCC
   421  AAGACCGACC CGGCCTTCAC CGAAGAGAAC AAGTACGAGC CCAACAGCCC GTACTCGGCC
   481  AGCAAGGCCG CCAGCGACCA CCTCGTGCGC GCCTGGCACC ACACCTACGG CCTGCCGGTG
   541  GTCACCACCA ACTGCTCGAA CAACTACGGG CCGTTCCACT TCCCCGAGAA GCTCATTCCC
   601  CTGATGATCG TCAACGCGCT GGCGGGCAAG CCGCTGCCCG TGTACGGCGA CGGCATGCAG
   661  GTGCGCGACT GGCTCTACGT GAAGGACCAC TGCAGCGCCA TCCGCCGCGT GCTCGAAGCC
   721  GGCAAGCTCG GCGAGACCTA CAACGTGGGC GGCTGGAACG AGAAGCCCAA CATCGAGATC
   781  GTCAACACCG TCTGCGCGCT GCTCGACGAG CTGAGCCCCA AGGCCGGCGG CAAGCCGTAC
   841  AAGGAACAGA TCACCTATGT GACCGACCGC CCCGGCCACG ACCGCCGCTA CGCGATCGAC
   901  GCACGCAAGC TCGAGCGCGA ACTCGGCTGG AAACCTGCCG AGACCTTCGA CAGCGGCATC
   961  CGCAAGACGG TCGAGTGGTA CCTCGCGAAC GGCGAGTGGG TGCGCAACGT GCAAAGCGGC
  1021  GCGTACCGCG AGTGGGTCGA GAAGCAATAC GACGCCGCAC CGGCGAAGGC CACCGCATGA
```

Fig. 12

```
SEQ ID NO 17
LENGTH: 891
TYPE: DNA
ORGANISM: Variovorax paradoxus

SEQUENCE: 17
     1  ATGAAGCTGC TGCTGCTGGG CAAGGGCGGA CAGGTCGGCT GGGAGCTGCA ACGCAGCCTC
    61  GCGCCCCTGG CGAACTGGT GGCGCTCGAT TCGACAGCA CCGACTTCAA CGCCGACTTC
   121  AGTCGCCCCG AGCAGCTGGC CGAGACAGTG CTGAAGGTGC GCCCCGACGT CATCGTCAAT
   181  GCCGCAGCGC ACACCGCGGT CGACAAGGCC GAGAGCGAGC CCGAGTTCGC GCGCAAGCTC
   241  AACGCCACCT CGCCCGGCGT GGTGGCCGAA GCCGCGCAGC AGATCGGCGC GCTGATGGTT
   301  CACTACTCGA CCGACTACGT CTTCGACGGC AGCGGCAGCA AGCCGTGGAA AGAAGACGAT
   361  GCGACCGGCC CGCTCAGCGT CTACGGCAGC ACCAAGCTCG AAGGCGAGCA ACTGGTGGCA
   421  AAGCACTGTG CGAAGCACCT GATCTTTCGC ACCAGCTGGG TCTATGCCGC GCGCGGCGGC
   481  AACTTCGCCA AGACCATGCT GCGCATCGCC AAGGAGCGCG ACAAGCTGAC CGTCATCGAC
   541  GACCAGTTCG GCGCGCCCAC CGGCGCGGAA CTGCTGGCCC ACATCACCGC GCACGCGATT
   601  CGCGCGACGC TGCAGGACCC GTCCAAGGCC GGGCTCTATC ACGCGGTGGC CGGTGGCGTG
   661  ACCGTGGC ACGGCTATGC GCGCTTCGTG ATCGAGCAGG CCAAGGCGGC GGGCGTGGAA
   721  CTGAAGGCCG GCCCCGAAGC GGTCGAGCGC GTGCCCACCA TGCCATTCCC GACGCCGGCC
   781  AGGCGGCCGC ACAACTCGCG CCTGGACACC ACCAAGCTGC AATCGACCTT CGGCCTCGTG
   841  CTGCCGAGT GGCAGTCCGG CGTCGCCCGC ATGTTGCGCG AAACCTTCTG A
```

Fig. 13

```
SEQ ID NO 19
LENGTH: 897
TYPE: DNA
ORGANISM: Variovorax paradoxus

SEQUENCE: 19
    1  ATGACCAAGA CGACGCAACG CAAAGGCATC ATCCTCGCCG GTGGCTCGGG CACCCGCCTG
   61  CACCCCGCGA CGCTTGCCAT GAGCAAACAA CTGCTGCCGG TGTACGACAA GCCGATGATC
  121  TATTACCCGC TGAGCACGCT GATGCTGGGC GGCATGCGCG ACATCCTGAT CATCAGCACG
  181  CCGCAGGACA CGCCGCGTTT CCAGCAACTG CTGGGGGATG GCAGCCAATG GGGCATCAAC
  241  CTGCAGTACG CGGTGCAGCC GAGCCCGGAT GGTCTGGCGC AGGCGTTCAT CATCGGTGAC
  301  AAGTTCGTGG GCAACGACCC GAGTGCGCTG GTGCTGGGGG ACAACATCTT CTATGGCCAC
  361  GACTTCGCCC ATCTGCTGGC CGATGCCGAC GCCAAGACCT CGGGTGCGAC GGTGTTCGCC
  421  TACCACGTGC ACGACCCCGA CGCCTACGGC GTGGTGGCCT TCGATGCCAA GGGCAGGGCG
  481  AGCAGCATCG AAGAAAAGCC GCTCAAGCCC AAGAGCAGCT ATGCGGTCAC GGGCCTCTAC
  541  TTCTACGACA ACCAGGTCGT CGACATCGCC AAGGCCGTGA AGCCGAGCGC GCGCGGCGAA
  601  CTCGAGATCA CCGCGGTCAA CCAGGCGTAT CTCGACCTCG ACCAGCTGAA CGTGCAGATC
  661  ATGCAGCGCG CTATGCGTG GCTCGATACC GGTACGCACG ACAGCCTGCT GGAAGCCGGG
  721  CAGTTCATTG CCACGCTCGA GCACCGCCAG GGGCTGAAGA TCGCATGCCC CGAAGAGATC
  781  GCATGGCGCA ATGGCTTCAT CTCAACCGAG CAACTCGAAA AGCTCGCGGC GCCGCTGGAA
  841  AAGAGCGGCT ACGGCAAGTA CCTCAAGCAC CTGCTGAACG ACGAGGTGCG CTCGTGA
```

Fig. 14

```
SEQ ID NO 21
LENGTH: 546
TYPE: DNA
ORGANISM: Variovorax paradoxus

SEQUENCE: 21
    1  GTGAAGGCCA CGCCCACCTC GATTCCTGAC GTGCTCGTGA TCGAGCCGAA GGTGTTTGGC
   61  GATGCACGGG GCTTCTTCTT CGAAAGCTTC AACCAGAAGG CCTTCGACGA AGCGATCGGC
  121  AAGCATGTCG ACTTCGTGCA GGACAACCAT TCGCGATCGG CCAAGGGTGT GCTGCGGGG
  181  CTGCATTACC AGGTCCAGCA GCCGCAAGGC AAGCTCGTGC GGGTGGTGCG TGGTGCGGTG
  241  TTCGACGTGG CCGTCGACAT CCGCAAGTCG TCGCCGACTT TTGGCAAATG GGTGGGTGTC
  301  GAGTTGAACG AAGACAACCA CAAGCAGCTC TGGGTGCCGG CAGGATTCGC GCACGGTTTC
  361  CTGGTGTTGA GCGAGACCGC GGAATTCCTC TACAAGACCA CCGACTACTA CGCGCCCGCC
  421  CACGAGCGCG CGATTGTCTG GAACGACCCC GCTGTCGGTA TTCGATGGCC GGATGTGGGA
  481  GGGGCACCGG TCCTGTCGAA GAAGGACGAA GACGGGTGTC TTCTGCAAGC GGCAGAGGTT
  541  TTCTAG
```

Fig. 15

SEQ ID NO 4
LENGTH: 304
TYPE: PEPTIDE
ORGANISM: Variovorax paradoxus

SEQUENCE: 4
MNGMHIDSVDLNLLRLFDAVYPERSVSRAAESLGLTQFAASHGLGRLRLLLKDALFTRAPGGVAPTPRADRLAVAVQ
AALGTIEAALHEPDRFEPQVSRKSFRIHMSDIGEGRFLPALMARLGELAPGVRLETLPLLPAEVAPALDSGRIDFAF
GFLSTVRDTQRTHLLKDRYIVLLRKGHPFVKRRREGQALLEALQELDYVAVRTHADTLRILQLLNLEDRLRLTTEHF
MVLPAIVRATDLAVVMPRNIARGFAEEGGYAIVEPPFPLRDFSVSLHWSKRFEGDPANRWLRQVITALFSERG

Fig. 16

SEQ ID NO 6
LENGTH: 2491
TYPE: PEPTIDE
ORGANISM: Variovorax paradoxus

SEQUENCE: 6
MSTVDQLGRTAPLTSGQMAMWLGAKFASPDTNFNLAEAIDIAGEIDPAIFLAAMRQVADEVEATRLSFIDTPQGPRQ
VVAPVFTGEIPYLDLSGESDPQAEAERWMHADYTRSIDLAHGQLWLSALIRLAPDRHIWYHRSHHIALDGFSGGLIA
RRFADIYTAMVDNNAAVPEDSRLAPISQLADEEHAYRESGRFPRDRQYWTERFADAPDPLSLASHRSVNVGGLLRQT
VHLPAASVQALQTIAQELGTTLPQILIATTAAYLYRATGIEDMAIGIPVTARHNDRMRPVPAMVANALPLRLAMRAD
LPIPELIREVGRQMPQILPHQSYRYEHLRSDLNMLVNNRQLFTTVVNVEPFDYDFRFAGHAAKPRNLSNGTAEDLGI
FLYERGNGQDLQIDFDANPAVHTAEELADHQRRLLAFIDAVIRLPLQAVGQIDLLGAEERQQLLVEWNDTAHAVPDT
HLTALIEAQLAADPQAIALRFDGEAMNNEELNRRANRLAHLLRARGAGPERTVALAIPRSMDLMIALLATLKTGAAY
LPVDPDFPADRIAFMLGDAQPVCLVTTEALAESLPAAAPTLLLDVAQTIADLESCNDTNPGIAIDPSHPAYVIYTSG
STGMPKGAVVSHRAIVNRLRWMQDRYGLQADDRVLQKTPSSFDVSVWEFFWPLIDGATLVLAKPGGHKDAAYLAGLI
AEEGITTIHFVFSMLEVFLLEPTAGACTTLRPVICSGEALSPALQSQFQQHLSCELHNLYGPTEAAVDVTSWECERT
DDAEASSVPIGRPIWNTQMHVLDSGLQPVPAGVIGELYIAGVGLARGYLXRPLLSAERFIANPYGTPGSRMYRIGDL
ARWRKDGSLDFLGRADQQVKIRGLRIEPGEIESVLLQHPQVAQAAVVAREDVPGEKRLVAYVVATDAADPQAAELRI
RLAQSLPEYMVPSAFVSLPSLPLGPSGKLDRKALPPPEVQAATPYAAPRTPTERILAGLWAETLRLPRVGVNDNFFE
LGGHSLMIVQLMSMIRQQFMIDLPVDTLFQVSTIAGLAELLDQESVARPSLTPMPRPARIPLSFAQRRLWLMNQLEG
ANPAYNMPLALRLSGVLDRTALHAALGDLVQRHESLRTVYPNEDGLPYQHILDGADARPAVIEADSSEEEIAAQLHA
AAGHAFDLGSAAPLRVYLFKLAGDEHVLLLLTHHIAGDGASLLPLARDISVAYAARCEGKAPGWEPLPLQYADYALW
QQELLGSEDDAESMAGRQREFWRSSLSDLPEQLALPVDHARPLVPTYRGDVVPLQIPSHVHERILQLARDGQASVFM
VLQAALAGLLSRLGAGDDIVIGSPVAGRSDHALDELIGCFVNTLVLRTDTSGQPSLRELVSRVRATNLAAYANQEFP
YDRLVELLRPGRSRANLPLFQVMLGFQGTSRLSFSLPGLSIAPQPVAIDTAKFDLSFILGEQRGADGLPGGISGGIQ
YSTDLFERSTVEAMGARLVRLLEEACEAPDDAVSGLAILSAEETDRLLSDWSGRTRDLAPLSFADMVASHAAERPLA
DAVVLDDATVSYAELDARANRLSHLLRAQGIGVGAIVATVLPRSLDLIVAHLAIVKAGAAYLPIDPNHMAARSAFVF
EEAAPAAVLTHDALLPELVGVPRCIALDSDSMVAALAIQSDTPLVHAANPQDAAYLIYTSGSTGMPKGVVVPHAGLG
SLGTAMAERLVIGHGSRVLQFSSSGFDASVMDQLMAFGAGAALVVPGFEQLLGTELADLLEKQAVSHALIPPAALAI
LPHGEFPHLQTLVVGGDACTAALAAKWSQGRRMINAYGPTEITICASMSAPMTAEELPSIGQPIWNTRMYVLDSALQ
PVPPGVAGELYIAGSGVARGYLNRPALSAERFIADPHGAPGSRMYRSGDLARWRADGTLDFLGRADQQVKIRGFRIE
PGEIESVLLKHPLITQAAVIAREDVPGEKRLVAYFVAGSFPQPTELRAHMAQALPDYMVPSAFVRLPSLPLTQSGKL
DKKALPVPDQQPAALYVEPRIPTEKLLAGLWSETLHLERVGIHDNFFEIGGHSLMAIQLGMRIRQQVRADFPHAEVY
NRPTIADLAAWLDNEGGIVEALDLSRELDLPAHIRPQATAPKLAPRRVFLTGASGFVGSHLLAALLRDTAACVVCHV
RAPDEQAGEQRLKRTLAQRQLGAIWDNARIKVVTGDLGKPRLGLDDAAVQLVRDGCDAIYHCAAQVDFLHFYASLKP
ANVDSVVTLLEWTAQGRAKSMHYVSTLAVIDQNNKEDTITEQSALASWSGLVDGYSQSKWVGDALAREAQARGMPVA
IYRLGAVTGDHTHAICNADDLIWRVAHLYADLEAIPDMDLPLNLTPVDDVARAILGLAAQEASWGQVFHLMSQAALR
VRDIPHVFERMGMRLEPVGLEPWLQRAHARLAVAHDRDLAAVLAILDRYDTTATPPQVSGAATHAQLEAIGAPIRPV
DRDLLQRYFVDLGIDTKARRALETTTS

Fig. 17

```
SEQ ID NO 8
LENGTH: 439
TYPE: PEPTIDE
ORGANISM: Variovorax paradoxus

SEQUENCE: 8
MARYLIAATALPGHVLPMLAIAQHLVNQGHEVRVHTASQFRAQAEATGAGFTPFERTIDFDYRDLDKRFPERQRIAS
AHAQLCFGLKHFFADAMAAQHAGLQSILEDFEADAIVVDIMFCGTFPLLLGKEREDRPAIVGIGISALPLSSCDTAF
FGTALPPSSTPEGRVPNKAMNANLKQAMFGEVQRYFDTLLARSGLAALPDFFVDAMVKLPDLYLQLTAPSFEYPRSD
LPASVHFVGPLLSPASRDFTPFEWWHELDDGRSVVLVTQGTLANQNPSQLIGPILQALAGDKNILVIATTGGPVPPA
LTVNLPANARVVPFLPYDRLLPKLHAMVTNGGYGSVNHALSLGVPLVVAGISEEKPEIAARVAWSGAGINLATGQPT
ARQVGDAVRKVLGNSTYRQRAAVLREDFACHRALTGIAGALEALLQTFASAEMA
```

Fig. 18

```
SEQ ID NO 10
LENGTH: 70
TYPE: PEPTIDE
ORGANISM: Variovorax paradoxus

SEQUENCE: 10
MSNPFDDKNASFQVLVNDEGQHSLWPAFIAVPAGWQVALAPTDRDACCAYIAANWQDMRPRSLVVATAAG
```

Fig. 19

```
SEQ ID NO 12
LENGTH: 322
TYPE: PEPTIDE
ORGANISM: Variovorax paradoxus

SEQUENCE: 12
MSFPFGAVVVTYFPTGEQVANLHSLAASCPHLCVVDNTPQVGDWHAALVDAGVSVLHNGNRGGIAGAFNRGIIDLEA
RGAELFFLLDQDSKLPPGYFDAMCEAAMVARERKGEGNGEEDAAFLIGPLVHDTNLDALIPQFGLQGKRVYQFDLRQ
PFTEPLMRCAFMISSGSLISRGAWARIGRFDERYVIDHVDTDYCMRALGRGVPLYLNPHVVLRHQIGDIRARSLFGW
KIHFINYPAARRYYIARNAIDLSRAHVRAFPAILFINVYTLKQILPMLMFERDRFKKTIALMLGCFDGLFGRLGGLG
EVHPRMGKYLGRSD
```

Fig. 20

```
SEQ ID NO 14
LENGTH: 419
TYPE: PEPTIDE
ORGANISM: Variovorax paradoxus

SEQUENCE: 14
MTATLPAPRVRRAALAFIFVTVLIDFMAFGLILPGLPHLVERLAGGSTVTAAYWIAVFGTAFAAIQFVSSPIQGALS
DRFGRRPVILLSCFGLGVDFVFMALADSLPWLFVGRVVSGVFSASFTIANAYIADVTLPEERARSYGIVGAAFGMGL
VFGPVLGGQLSRIDPRLPFWFAAGLTLLSFCYGWFVLPESLPPERRARKFDWSHANPVGTLVLLKRYPQVFGLAAVI
FLVNLAQYVYPSVFVLFADYRYHWKEDAVGWVLGAVGVLSVLVNALLIGPGVKRFGERRALLGMGFGVLGFVIIGF
ADAGWILLAGVPFGILLAFAGPAAQALVTLQVGTAEQGRIQGALTSLVSVAGIVGPAMFAGSFGYFIGADAPVHLPG
APFFLAAAFLCIGTLIAWRYAQPKPATAAVPEPT
```

Fig. 21

```
SEQ ID NO 16
LENGTH: 359
TYPE: PEPTIDE
ORGANISM: Variovorax paradoxus

SEQUENCE: 16
MILVTGGAGFIGANFVLDWLAQSDEPVVNLDKLTYAGNLETLASLKDNPKHIFVQGDIGDSALLDRLLAEHKPRAVV
NFAAESHVDRSIHGPEDFVQTKVLGTFRLLESVRGFWNALPADQKAAFRFLHVSTDEVYGSLSKTDPAFTEENKYEP
NSPYSASKAASDHLVRAWHHTYGLPVVTTNCSNNYGPFHFPEKLIPLMIVNALAGKPLPVYGDGMQVRDWLYVKDHC
SAIRRVLEAGKLGETYNVGGWNEKPNIEIVNTVCALLDELSPKAGGKPYKEQITYVTDRPGHDRRYAIDARKLEREL
GWKPAETFDSGIRKTVEWYLANGEWVRNVQSGAYREWVEKQYDAAPAKATA
```

Fig. 22

```
SEQ ID NO 18
LENGTH: 296
TYPE: PEPTIDE
ORGANISM: Variovorax paradoxus

SEQUENCE: 18
MKLLLLGKGGQVGWELQRSLAPLGELVALDFDSTDFNADFSRPEQLAETVLKVRPDVIVNAAAHTAVDKAESEPEFA
RKLNATSPGVVAEAAQQIGALMVHYSTDYVFDGSGSKPWKEDDATGPLSVYGSTKLEGEQLVAKHCAKHLIFRTSWV
YAARGGNFAKTMLRIAKERDKLTVIDDQFGAPTGAELLADITAHAIRATLQDPSKAGLYHAVAGGVTTWHGYARFVI
EQAKAAGVELKAGPEAVEPVPTTAFPTPARRPHNSRLDTIKLQSTFGLVLPEWQSGVARMLRETF
```

Fig. 23

```
SEQ ID NO 20
LENGTH: 298
TYPE: PEPTIDE
ORGANISM: Variovorax paradoxus

SEQUENCE: 20
MTKTTQRKGIILAGGSGTRLHPATLAMSKQLLPVYDKPNIYYPLSTLMLGGMRDILIISTPQDTPRFQQLLGDGSQW
GINLQYAVQPSPDGLAQAFIIGDKFVGNDPSALVLGDNIFYGHDFAHLLADADAKTSGATVFAYHVHDPERYGVVAF
DAKGRASSIEEKPLKPKSSYAVTGLYFYDNQVVDIAKAVKPSARGELEITAVNQAYLDLDQLNVQIMQRGYAWLDIG
THDSLLEAGQFIATLEHRQGLKIACPEEIAWRNGFISTEQLEKLAAFLEKSGYGKYLKHLLNDEVRS
```

Fig. 24

```
SEQ ID NO 22
LENGTH: 181
TYPE: PEPTIDE
ORGANISM: Variovorax paradoxus

SEQUENCE: 22
MKATPTSIPDVLVIEPKVFGDARGFFFESFNQKAFDEAIGKHVDFVQDNHSRSAKGVLRGLHYQVQQPQGKLVRVVR
GAVFDVAVDIRKSSPTFGKWVGVELNEDNHKQLWVPAGFAHGFLVLSEIAEFLYKTIDYYAPAHERAIVWNDPAVGI
RWPDVGGAPVLSKKDEDGCLLQAAEVF
```

Fig. 25

SEQ ID NO 23
LENGTH: 1029
TYPE: DNA
ORGNAISM: Variovorax paradoxus

SEQUENCE: 23
```
   1 ATGGGCAGCA GCCATCATCA TCATCATCAC AGCAGCGGCC TGGTGCCGCG CGGCAGCCAT
  61 ATGTCCTTCC CGTTCGGTGC CGTCGTCGTC ACCTATTTCC CGACCGGCGA GCAAGTGGCG
 121 AACCTCCATT CGCTGGCGGC CTCGTGTCCG CACCTCTGCG TGGTCGACAA CACGCCGCAG
 181 GTGGGCGATT GGCATGCGGC GCTCGTCGAT GCGGGCGTTT CGGTGCTGCA CAACGGCAAC
 241 CGCGGCGGCA TCGCGGGCGC CTTCAACCGC GGCATCATCG ACCTCGAAGC GCGGGGCGCC
 301 GAACTCTTCT TCCTGCTCGA CCAGGATTCG AAGCTGCCAC CCGGCTACTT CGATGCCATG
 361 TGCGAGGCTG CGATGGTGGC CCGGGAGCGG AAGGGCGAGG GCAATGGTGA GGAAGACGCG
 421 GCCTTCCTGA TCGGCCCGCT CGTCCACGAC ACGAACCTGG ACGCGCTGAT CCCGCAATTC
 481 GGCCTCCAGG GCAAACGCGT CTACCAGTTC GACCTGCGGC AGCCCTTCAC CGAGCCGCTG
 541 ATGCGCTGCG CCTTCATGAT TTCCTCGGGC TCCCTGATTT CGCGCGGCGC CTGGGCCCGG
 601 ATCGGCCGGT TCGACGAGCG CTATGTGATC GACCACGTGG ACACCGACTA CTGCATGCGT
 661 GCCCTGGGTC GCGGCGTGCC GCTCTACCTG AATCCGCACG TCGTGCTGCG CACCAGATT
 721 GGCGACATCC GTGCCCGGTC GCTGTTCGGC TGGAAGATCC ACTTCATCAA CTACCCGGCC
 781 GCGCGGCGCT ACTACATCGC GCGCAATGCC ATCGATCTCT CGCGGGCGCA TGTGCGCGCC
 841 TTTCCCGCGA TCCTGTTCAT CAACGTTTAC ACGCTCAAGC AGATCCTGCC GATGCTGATG
 901 TTCGAGCGCG ACCGCTTCAA GAAGACCATC GCGCTGATGC TCGGCTGCTT CGATGGCCTG
 961 TTCGGGCGGC TCGGGGGCCT CGGCGAGGTG CATCCGCGGA TGGGCAAATA CCTGGGCCGC
1021 AGCGATTGA
```

Fig. 26

SEQ ID NO 24
LENGTH: 342
TYPE: PEPTIDE
ORGANISM: Variovorax paradoxus

SEQUENCE: 24
MGSSHHHHHHSSGLVPRGSHMSFPFGAVVVTYFPTGEQVANLHSLAASCPHLCVVDNTPQVGDWHAALVDAGVSVLH
NGNRGGIAGAFNRGIIDLEARGAELFFLLDQDSKLPPGYFDAMCEAAMVARERKGEGNGEEDAAFLIGPLVHDTNLD
ALIPQFGLQGKRVYQFDLRQPFTEPLMRCAFMISSGSLISRGAWARIGRFDERYVIDHVDTDYCMRALGRGVPLYL
NPHVVLRHQIGDIRARSLFGWKIHFINYPAARRYYIARNAIDLSRAHVRAFPAILFINVYTLKQILPMLMFERDRFK
KTIALMLGCFDGLFGRLGGLGEVHPRMGKYLGRSD

Fig. 27

SEQUENCE LISTING

```
Sequence total quantity: 24
SEQ ID NO: 1              moltype = DNA  length = 12721
FEATURE                   Location/Qualifiers
source                    1..12721
                          mol_type = genomic DNA
                          organism = Variovorax paradoxus
SEQUENCE: 1
gtcgtgtctc cttcttttcg tggggtgttc caacgggccg actgggaggt cggctgaaaa  60
ccgctcgcca gtgtgcgtgc cgcaaggttt gccttcaata aaataatcaa gctaagtaat  120
atgaatggca tgcatatcga ctcggtcgac ctcaatctgc tgcgcctgtt cgatgcggtc  180
taccgcgagc gcagcgtgag ccgcgccgcg gagtcgctgg gcctcacgca gcctgcggca  240
agccatgggc tgggacggct gcggctgctt ttgaaagacg cgctcttcac gcgtgccccc  300
ggcggcgtgg cgcccacgcc gcgcgccgac cggctgcgcg tggcggtgca ggcggcgctc  360
ggcacgatcg aagcggcgct gcacgagccc gatcgcttcg agcccaggt gtcgcgcaag  420
agctttcgta ttcacatgag cgacatcggc gaggggcgct tcctgcccgc gctgatggcg  480
cggctcggcg agctggcgcc cggcgtgcgg ctggagaccc tgccgctctt gcctgcggag  540
gttgcgcccg cactcgacag cggccgcatc gatttcgcct tcggctttct ctcgaccgtg  600
cgcgacacgc agcgcacgca tcttctgaaa gaccgctaca tcgtgctgct gcgcaagggc  660
catcccttg tgaagcgccg gcgcaagggg caggcgctgc tcgaggcgct gcaggagctc  720
gactacgtgg cggtgcgcac gcacgccgac acgctgcgca tcttgcagtt gctcaacctc  780
gaagaccgcc tgcgcctcac gaccgagcac ttcatggtgc taccggccat cgtgcgcgcc  840
accgatctcg cggtggtgat gccgcgcaac atcgcgcgag ggtttgcgga ggagggcggc  900
tacgcgatcg tcgagccgcc gtttccgctg cgcgatttca gcgtgtcgct gcactggagc  960
aagcgcttcg agggcgaccc ggccaaccgt tggttgcggc aggtgatcac ggcgctgttc  1020
tccgagcgcg gctgaagttc gaccaccaaa gtacgcgccg cgcggtgcaa gcgcgcgcga  1080
ctgcgcgagt aacacgccga gagattcccc tacagctttc tcgcccagtt gctgcatcgc  1140
aacattcttt tggggtgcat gacgcgcgaa atacgatgaa agccttcgat tccgaaagcc  1200
gcgattcagg tcgcaacttc gggatgaaat ctttcgcgct caaagacgtt cgtgaaatgt  1260
tttcttccct aaaaccgtca ctgaaagtgt tgaaccact tgtacagtgg actggcaatg  1320
tgaacggatt gttaccgcgg agcaccggca tttctccttg agcggccgat gcacgacgcg  1380
tccatttcac gcgcaacatgc atcgttgcca atttcactca agacctggag aagtgcatga  1440
gtaccgtcga tcagctgggc cgcaccgccc cccttacctc ggggcagatg gcgatgtggc  1500
tcggcgcaaa gttcgcgtcg cccgacacca atttcaatct cgccgaagcc atcgacatcg  1560
caggcgagat cgacccgcg atcttcctgg cggccatgcg acaggtggcc gatgaagtcg  1620
aggccacgcg cctgagcttc atcgatcacc cgcaagggcc acgacaggtc gtcgcgcccg  1680
ttttcaccgg cgagatcccc tacctcgacc tcagcggcga gagcgatccg caggccgagg  1740
ccgagcgctg gatgcatgcg gactacaccc gcagcatcga cctcgcgcac gggcagctgt  1800
ggctgtccgc gctgatccgc ctcgcgcccg atcgccacat ctggtaccac cgcagccatc  1860
acatcgcgct cgacggcttc agcggcggcc tcatcgcacg ccgcttcgcc gacatctaca  1920
ccgcgatggt cgacaacaac gcagcggtgc ccgaagactc gcgccttgca ccgatctcgc  1980
agctggccga cgaagaacat gcctatcgcg agtccggccg cttcccgcgc gaccgccagt  2040
actggaccga gcgcttcgcc gatgcacccg atccgttgag cctcgcctcg caccgctcgg  2100
tcaacgtcgg tggcctcttg cgccagacgg tgcacctgcc ggcggccagc gtgcaagccc  2160
tgcagaccat cgcgcaagag ctcggcacca cgctgccgca aatcctcatc gccaccaccg  2220
cggcctacct gtaccgcgca acgggcatcg aggacatggc aatcggcatc cccgtcaccg  2280
cgcgccacaa cgaccgcatg cgccgcgtgc ccgcgatggt ggccaacgcg ctgccgctgc  2340
gcctggcgat gcgcgcggac ctgccgattc cggaactgat ccgcgaagtc ggccggcaga  2400
tgcggcagat cctgcgcgcac cagtcgtatc gctacgagca tttgcgcagc gacctcaaca  2460
tgctggtgaa caaccggcag ctcttcacca ccgtggtcaa cgtcgagccc ttcgactacg  2520
acttccgctt tgcgggccat gccgcgaagc cgcgcaacct ctcgaacggc acggccgagg  2580
acctcggcat cttcctgtac gagcgcggca acgggcagga cctgcagatc gacttcgacg  2640
ccaacccgcc ggtgcatcac gcagaggaac tggccgatca ccagcgccgc gtgcttgcct  2700
tcatcgacgc cgtgatccgc ctgccgttgc aggccgtcgg ccagatcgac ctgctcggtg  2760
ccgaagagcg gcagcaattg ctggtcgagt ggaacgacac ggcccacgcc gtgcccgaca  2820
cccatctcac cgcgttgatc gaagcgcagc tcgcagccga tccgcaagcc atcgcattgc  2880
gcttcgacgc cgaggcgatg aacaacgaag aactgaaccg ccgcgcaaca cgtctgcagc  2940
acctgctgcg cgcacgcggc gctggccgg agccaccgt ggcgctcgcg atccgcgtt  3000
cgatggacct gatgattgcc ttgctcgcca cgttgaagac cggcgcggcc tacctgccgg  3060
tcgatccgga tttcccggcg gaccgcatcg ccttcatgct cggcgatgcg cagcccgtgt  3120
gcctcgtcac gaccgaagcc ctcgcggagt cgctgccggc agccgcccc acattgctgc  3180
tcgatgtagc gcaaacgatt gcggatctgg agagttcaa cgacaccaac ccgggcatcg  3240
```

```
cgatcgaccc ttcgcatccg gcctatgtga tctacacctc gggctcgacc ggcatgccca  3300
agggtgcggt cgtgtcgcac cgcgccatcg tcaaccgcct gcgctggatg caggaccgct  3360
acggccttca ggccgacgac cgcgtgctgc agaagacgcc ttccagcttc gacgtgtcgg  3420
tgtgggagtt cttctggccg ctgatcgacg gtgccacgct ggtgcttgcg aaaccgggcg  3480
gccacaagga tgcggcctac ctcgcgggc tgatcgcgga ggagggcatc accacgatcc  3540
acttcgtgcc gtcgatgctc gaggtcttcc tgctcgagcc cacggcgggc gcatgccacca  3600
cgctgcgccg cgtgatctgc agcggcgaag ccttgtcgcc cgcgctgcaa tcgcagttcc  3660
agcagcacct ctcgtgcgag ctgcacaacc tctacggtcc gaccgaggcc gcggtcgacg  3720
tcacctcgtg ggagtgcgaa cgcacggacg acgcagaagc ctcgagcgtt cccatcggcc  3780
gcccgatctg gaacaccag atgcacgtgc tcgacagcgg cctgcagccc gtgccggccg  3840
gcgtgactgg cgagctgtac atcgcgggcg tcggcctcgc acgcggctac ctcaagcgcc  3900
cgttgctgag cgccgagcgt ttcatcgcca accctacgg cacacccggc agccgcatgt  3960
accgcaccgg cgacctcgcg cgctggcgca aggacgcag ccttgacttc ctcggccgcg  4020
ccgaccagca ggtgaagatc cggggcctgc gcatcgagcc gggagagatc gaatccgtcg  4080
tgctgcagca tccgcaagtc gcgcaggccg ccgtggtggc gcgcgaagac gtaccgggcg  4140
aaaagcgtct cgtggcctac gtcgttgcga cggacgctgc cgatccgcaa gcggccgaac  4200
tgcgcacgcg cctcgcgcaa tcgctgcccg agtacatggt gccttcggcc ttcgtcagcc  4260
tcccgtcgct gccgctcgga cccagcgaca gctcgaccg caaggcgctg ccgccccccg  4320
aagtgcaggc cgccacgccg tacgccgcgc cgcgcacgcc gaccgaaaag atcctcggccg  4380
gcctctgggc cgagacgctg catttgccgc gcgtcggtgt caacgacaac ttcttcgaac  4440
tcggcggcca ctcgctgatg atcgtgcagc tcatgtcgat gatccggcag caattcatga  4500
tcgacctgcc ggtcgacacg ctgttccagg tctccaccat cgcggccctt gccgagctgc  4560
tcgaccagga atcggtcgcc cgtccgagcc tgactccgat gccgcgcccc gcgcgcattc  4620
cgctgtcctt cgcgcagcgc cgcctgtggc tgatgaacca gctcgaaggc gcgaacccgg  4680
cctacaacat gccgctcgcg ctgcgcctgt cgggtgtgct cgatcgcacc gcattgcatg  4740
cggcgctcgg cgacctggtg cagcgccacg agagcctgcc cacggtctca ccgaaccgaag  4800
acgggctgcc gtaccagcac atcctcgacg gcgcggatgc gcgtccggcg gtgatcgagg  4860
ccgacagcag cgaagaagaa atccgggcgc agcttcacgc cgctgcgggc catgccttcg  4920
atctcggcag cgcggcgccc ttgcgcgtct acctgttcaa gctcgccggc gacgaacacg  4980
tgctgctgct gctcacgcac cacattgccg gcgatgcggc ctcgctgccc ccgctagcgc  5040
gcgacatcag cgtggcctat gccgcgcgct gcgaaggcaa ggcgccgggc tgggagccgc  5100
tgccgctgca atacgccgac tacgcgctgt ggcagcagga gctgctcggc agcgaagacg  5160
atgccgagac catggccggc cgccagcgtg agttctggcg ttcctcgctg agcgacctgc  5220
ccgagcaact ggcgctgccc gtcgaccacg cacggccgct cgtgccgaca taccgcggcg  5280
atgtggtccc gctgcagatt ccgtcgcatg tgcatgaacg catcctgcaa ctggcgggcg  5340
acgggcaggc cagcgtcttc atggtgctgc aggccgcact cgcggggcctc ctgagccgcc  5400
tcggcgcggg cgacgacatc gtcatcggca gcccggtcgc ggggcgcagc gaccatgcgc  5460
tggacgaact catcggctgc ttcgtcaaca cgctggtgct gcgcactgac acctcgggcc  5520
agccggagct gcgcgagctg gtctcgcgcg tgcgcgccac caacctcgcg gcctatgccga  5580
accaggagtt tccgtacgac cgcctcgtgg agctgctgcg tccgggccgc tcgcgcgcca  5640
acctgccgct gttccaggtc atgctgggct tccagggcac gagccgcctg tcgttcagcc  5700
tgccgggcct gtcgatcgcg ccgcagccgg tggccatcga caccgcgaag ttcgacctgt  5760
cgttcatcct cggcgagcaa cgcggtgccg atggcctgcc ccggcggatc tccggcggca  5820
tccagtacag caccgacctg ttcgagcgca gcacgtcga ggcatgggc gcgcggctgg  5880
tgcgtttgct ggaagaggcc tgcgaggcgc ccgacgatgc ggtgagtggc ctcgccatcc  5940
tgagcgcgga agaaaccgac cgcctgctgt ccgactggag cggccgcacg cgcgaccttg  6000
cgccgctctc gttcgccgac atggtggcct cgcatgccgc ggagcgcccg cttgcagatg  6060
cagtggtgct cgacgacgcg accgtcagct acgccgaact cgatcacgcg gccaaccggc  6120
tctcgcacct gctgcgtgcg caaggcatcg gggttggcgc catcgtcgcg acagtgctgc  6180
cgcgttcgct cgacctcatc gtggcgcact tggccatcgt gaaggccggc gcggcctacc  6240
tgcccatcga cccaaccac atggccgagc gcagcgcct cgtgttcgag gaggccgcc  6300
ccgccgcggt gctgacgcac gatgcgcgtg tgcccgagct ggtcggcgtt ccccgctgca  6360
tcgcgctcga cagcgacagc atggttgccg cgctggccat ccagtcggat acgccgctgg  6420
tgcatgcggc caatccacag gatgccgcct acctcatcta cacctccggc tccaccggca  6480
tgcccaaggg cgtggtggtg ccgcatgcgg gcctgggcag cctcggcacc gcgatggcgg  6540
agcggctcgt catcggccac ggctcgcgcg tgctgcagtt ctcctccagc ggcttcgacg  6600
cgtcggtgat ggaccagctg atggcctttg gcgccggtgc cgcgctggtg gtgccgggg  6660
cggagcaact gctcggcacg gagctggccg atctgctcga aagcaggcc gtgagccacg  6720
cgctgattcc gcccgcgcg ctcgcgacc tgccgcacgg cgagttcccg cacctgcaga  6780
cgctggtggt cggcggcgat gcctgcaccg ccgcgtcgg ggcgaagtgg tcgcaaggcg  6840
gccgcatgat caacgcctac ggccgaccg agatcaccat ctgcgcgagc atgagcgcgc  6900
cgatgacggc cgaggagttg ccctccatcg gccagccgat ctggaacacg cggatgtatg  6960
tgctcgacag cgccctgcaa ccggtgccgc cgggtgtcgc gggcgagctc tacatccccg  7020
gcagccgcgt ggccgcgggc tatctcaacc ggccggcatt gagtgcggaa cgcttccatcg  7080
ccgaccgcga tggcgcgccc ggcagccgca tgtaccgcag cggcgacctc gcacgctggc  7140
gcgccgacgg cacgctcgac ttcctcggcc gcgccgacca gcaggtgaag atccggggct  7200
tccgcatcga gccgggcgag atcgaatccg tgctgctcaa gcaccgttg atcacgcagg  7260
ccgcgtgat cgcccgcgag gacgtgagccg gcgagaagcc cctggtcgcc tacttcgtcg  7320
ccggttccga gccgcagccc accgcgcac cgcgccacat cggcgagttc ttgcccgact  7380
acatggtgcc ttcggccttc gtgcgcctgc cgtcgcgcc gctcacgcaa agcggcaagc  7440
tcgacaagaa ggcgctgccg gtgcccgacc agcagcccgc cgcgctgtac gtggagcccc  7500
gcacgccgac cgagaaactg ctcgcgggcc tctggtccga cgctgcac ctggagcgtg  7560
tcggcatcca cgacaacttc ttcgagatcg cgggcattc gctcatggcg atccagctgg  7620
gcatgcgcat ccgccagcag gtgcgcgacg acttccccga gccaggctc ttgcccgaga  7680
cgacgattgc cgacctggcc gcctggctcg acaacgaagg cggcacgtc gaggcgctgg  7740
acctgtcgcg cgagctcgac ctgcccgcgc acatccgccc gcaggccact gcaccgaagc  7800
tcgcaccgcg ccgcgtgttc ctcaccggcg cgagcggctt cgtcggcagt cacctgctgg  7860
ccgcgctgtt gcgcgacacc gcggcctgcg tggtctgcca cgtgcgcgcg cccgacgagc  7920
aggccggcga gcagcgcctc aagcgcacgc tggcccagcc ccagctcggt gcgatctggg  7980
```

```
acaacgcgcg catcaaggtc gtgaccggcg acctcggcaa gccgcgcctg ggcctcgatg    8040
acgctgccgt gcaactggtg cgcgacggct gcgacgccat ctaccactgc gccgcgcagg    8100
tcgacttcct gcatccctac gcgagcctca agcccgcgaa cgtcgacagc gtggtcacgc    8160
tgctcgaatg gacggcgcag gggcgcgcga agagcatgca ctacgtctcc acgctggctg    8220
tgatcgacca gaacaacaag gaagacacca tcaccgacgc atcggcgctg gcctcatgga    8280
gcgggctggt cgacggctac agccagagca agtgggtcgg cgatgcgctg gcccgcgagg    8340
cgcaggcgcg cggcatgccg gtggcgatct accggctggg ggcagtcacc ggcgaccaca    8400
cgcacgcgat ctgcaatgcc gacgacctga tctggcgcgt ggcgcatctc tatgccgacc    8460
tggaagcgat tcccgatatg gacctgccgc tcaacctcac accggtggac gacgtggcgc    8520
gcgccatcct cggccttgcg gcgcaggagg cctcgtgggg ccaggtgttc cacctgatga    8580
gccaggcggc gctgcgggtg cgcgacattc cgcacgtctt cgagcgcatg ggcatgcggc    8640
tggagccggt cgggctggag ccctggctgc agcgcgcgca tgcacggctg gccgtcgcgc    8700
atgaccgcga cctggccgcg gtgctcgcca tcctcgaccg ctacgacacc acggccacgc    8760
cgccgcaggt gagcggccgg gccacgcatg cgcagctcga ggccatcgga aggccgaggc    8820
gcccggtgga ccgcgacctg ctgcagcgct acttcgtcga cctgggcatc gacaccaagg    8880
cgcgccgcgc cctggaaacc accacttcat aggagcacac ggaatggcac gctatctcat    8940
cgcagcaacc gccttgccgg gacacgtcct gccgatgctg gccatcgcgc agcatctggt    9000
gaaccagggg cacgaggtgc gggtgcacac cgcgagccga ttcagggcgg aggccgaggc    9060
gaccggtgcg ggcttcacgc ccttcgagcg cacgatcgac ttcgactacc gcgacctgga    9120
caagcgcttt cccgagcgcc agcgcatcgc ctcggcgcat gcgcagctgt gcttcggcct    9180
gaagcacttc tttgccgatg cgatggccgc gcagcatgcg ggcctgcaat cgatcctcga    9240
agacttcgag gccgatccga tcgtggtcga cacgatgctc tgccgcactt tcccgctgct    9300
gctaggcaag gagcgcgaag accgccggc catcgtcggc atcggcatct cggcgctgcc    9360
gctctcgagc tgcgacaccg ccttcttcgg caccgcgctg ccgccgtcgt ccacgccgga    9420
agggcgggtg cgcaacaagg cgatgaacgc caacctcaaa caggcgatgt tcggcgaggt    9480
gcaacgctac ttcgacacgc tgctcgcgcg ttcgggcctg gccgcgctgc gcgatttctt    9540
cgtcgatgcg atggtgaagc tgcccgatct ttacctgcag ctcaccgcgc cttcgttcga    9600
ataccecgcgc agcgacctgc ccgcgtcggg gcatttcgtc ggcccgctgc tctcgcccgc    9660
gagccgcgac ttcacgccgc ccgagtggtg cacgagctg gacgacggcc gctcggtcgt    9720
gctggtcacg cagggcacgc tggccaacca gaatccgtcg cagctgatcg gcccgacgct    9780
gcaggcgctg gccggcgaca agaacatcct cgtcatcgcc accacgcgg gcccggtgcc    9840
gcccgccctg acgtgaacc tgccgcaa cgcccgcgtg gtgccgttcc tgccctacga    9900
ccggctgctg cccaagctgc acgcgatggt caccaacggc ggctacggct cggtcaacca    9960
tgcattgagc ctcggtgtgc cgctggtggt ggccggcacc tccgaagaga agccgagat   10020
cgcccgcgc gtggccttgg cgggcgcggg catcaacctc gccaccggcc agccgaccgc   10080
gcgccaggtc ggcgacgcgg tgcgcaaggt actgggcaac tcgacctatc gccagcgtgc   10140
ggcggtgctg cgtgaggact tcgcttgcca tcgcgcgctg accggcatcg ccggcgccct   10200
cgaggcactt ctgcaaacct tcgcatccgc ggaaatggct tgaacctgaa ccccatacga   10260
caaaggaaat cccagatgag caacccgttc gacgacaaga aggcagctcc caggtgctg   10320
gtgaacgacg agggcagca ctcgctgtgg cccgccttca tcgccgtgcc cgccggctgg   10380
caggtggcgc tggcgccgac cgaccgcgac gcctgcagcg cctacatcgc ggcgaactgg   10440
caggacatgc gcccgcgttc gctggtggtg gccacgcgg ccggctgacg ccgaggatgt   10500
ccttcccgtt cggtgccgtc gtcgtcacct atttcccgac ggcgagcaa gtggcgaacc   10560
tccattcgct ggcggcctcg tgtccgcacc tctgcgtggt cgacaacacg ccgcaggtgg   10620
gcgattggca tgcggcgctc gtcgatgcgg gcgtttcggt gctgcacaac ggcaaccgcg   10680
gcggcatcgc gggcgcctc aaccgcggca tcatcgacct cgaagcgcgg ggcgccgaac   10740
tcttcttcct gctcgaccag gattcgaagc tgccaccgg ctacttcgat gccatgtgcg   10800
aggctgcgat ggtggcccgg gagcggaagg cgagggcaa tggtgaggaa gacgcggcct   10860
tcctgatcgg cccgctcgtc cacgacacga acctggacgc gctgatcccg caattcggcc   10920
tccagggcaa acgcgtctac cagttcgacc tgcggcagcc cttcaccgag ccgctgatgc   10980
gctgccctt catgatttcc tcgggctccc tgatttcgcc cggcgcctgg gcccgaatg   11040
gccggttcga cgagcgctat gtgatcgacc acgtggacac cgactactgc atgcgtgccc   11100
tgggtcgcgg cgtgccgctc tacctgaatc cgcacgtcgt gctgcggcac cagattggcg   11160
acatccgtgc ccggtcgctg ttcggctgga agatccactt catcaactac ccggccgcgc   11220
ggcgctacta catcgcgcgc aatgccatcg atctctcgcg ggcgcatcg gcgcctttc   11280
ccgcgatcct gttcatcaac gtttacacgc tcaagcagat cctgccgatg ctgatgttcg   11340
agcgcgaccg cttcaagaag accatcgcgc tgatgctcgg ctgcttcgat ggcctgttcg   11400
gcggctcgg gggcctcggc gaggtgcatc cgcggatggg caaatacctg ggccgcagcg   11460
attgaccgcc acccttccag cgccgcgcgt acgccgcgcc gcgctcgcct tcatcttcgt   11520
cacggctgctg atcgacttca tggcgttcgg cctgatcctg cccggcctgc cgcacctgt   11580
ggagcggctg gccggcggca gcacggtaac ggcggcgtac tggatcgctg tgttcggcac   11640
cgcgttcgcg gcgatccagt tcgtgagctc gccgatccag ggcgcgctgt ccgaccgctt   11700
cgggcggcgg ccggtgatcc tgctgtcgtg cttcggcctc ggcgtggatt tcgtgttcat   11760
ggccctggcc gacagcctgc cgtcgctgtt cgtcggccgg gcgtgttctc   11820
ggccagcttc accatcgcca atgcctacat cgccgatgtg acgctgccgg aggagcgcgg   11880
ccgcagctac ggcatcgtgg gggccgcgtt cggcatgggc ctggtgttcg ggccggtgct   11940
cggcgggcaa ctgagccaca tcgatccgcg cctgccgttc tggttcgcgg ccggcttgac   12000
gctgctcagc ttctgctacg gatggttcgt gttgcccgaa tcgctgccgc ccgagcggcg   12060
tgcccgcaag ttcgactggt cgcatgccaa tccggttggg acgctgggtg ctgtcaagcg   12120
ctatccgcag gtgttcggac tggcggcggt gatcttcctc gtgaacctgg ctcagtacgg   12180
ctatcccagc gtgttcgtgc tgttcgccga ctaccggtat cactgaagg aagacgccgt   12240
gggctgggtg ctcggcgcgg tgggcgtgct cagcgtgctg gtcaatgcgc tgttgatcgg   12300
gccgggcgtg aagcgcttcg gcgagcgccg cgccctgttg ctcggcatgg gcttcggcgt   12360
gctcatcatcg ggtttgccga gcgatggcg atcctcctgg tcggggtcgt   12420
gttcggcatt ctgctggcgt tcgcggacc ggcggcgcag gcgctggtca cgctgcaggt   12480
cggcaccgcc gagcagggcc gcatccaggg ggcgctcacc agctggtgt cggtggcggg   12540
catcgtcggg ccggcgatgt tcgccggcag cttcggttac ttcatcggcg cggacgcgcc   12600
ggtgcacttg ccggggcgcg cgttttcct cgctgcggcc ttcctctgca tcggcacgct   12660
gatcgcgtgg cgctacgcac agccgaagcc cgcgacggca gcggtgcccg agccgacctg   12720
``` a                                                                                            12721

| SEQ ID NO: 2 | moltype = DNA  length = 3959 |
| FEATURE | Location/Qualifiers |
| source | 1..3959 |
| | mol_type = genomic DNA |
| | organism = Variovorax paradoxus |

SEQUENCE: 2

```
ccgctgcgcc tcgcaacggg tttgctcctt cggtgcatcg cgatccctgc gggtgcgatg    60
gctctccaga cggcgtttga tgtgatgcag tactgacccc ctgttcgggc cgacctgagc   120
gtttatggga gtttgcgcct tcggtagggc caccggggtg gcccgctctc ctgcagtggg   180
gcgattgtag gtgggcactg ccaatgcgcc aaccccggga gtttcggccc ttgggccgat   240
gggataatca tccgttcatt cgccggaggg cgatcgttcg acaacaacag gggacccat    300
gatcctggta accggcggcg caggcttcat tggcgccaat ttcgtactcg actggctcgc   360
acagagcgat gaaccggtcg tgaacctaga caagctgacc tacgcgggca acctcgagac   420
gctcgcatcg ctcaaggaca acccgaagca catcttcgtg cagggcgaca tcggcgacag   480
cgcgctgctc gaccgcctgc tggccgagca caagccgcgt gccgtggtca acttcgcggc   540
cgaatcgcac gtcgaccgct cgatccacgg ccccgaagac ttcgtgcaga ccaacgtgct   600
gggcaccttc cgcctgctcg aatccgtgcg cggtttctgg aatgcccctgc cggccgacca   660
gaaggccgcc ttccgcttcc tgcatgtgtc gaccgacgag gtctacggct cgctctccaa   720
gaccgacccg gccttcaccg aagagaacaa gtacgagccc aacagccgt actcggccag    780
caaggccgcc agcgaccacc tcgtgcgcgc ctggccaacc acctacggcc tgccggtggt   840
caccaccaac tgctcgaaca actacggcc gttccacttc cccgagaagc tcattccct    900
gatgatcgtc aacgcgctgg cgggcaagcc gctgcccgtg tacggcgacg gcatgcaggt   960
gcgcgactgg ctctacgtga aggaccctg cagcgccatc cgccgcgtgc tcgaagccgg  1020
caagctcggc gagacctaca acgtgggcgg ctggaacgag aagcccaaca tcgagatcgt  1080
caacaccgtc tgcgcgctgc tcgacgagct gagcccaag gccggcggca agccgtacaa   1140
ggaacagatc acctatgtga ccgaccgccc cggccacgac cgccgctacg cgatcgacgc  1200
acgcaagctc gagcgcgaac tcggctggaa acctgccgag accttcgaca gcggcatccg  1260
caagcggctc gagtggtacc tcgcgaacgg cgagtggtg cgcaacgtgc aaagcggcgc  1320
gtaccgcgag tgggtcgaga agcaatacga cgccgcaccg gcgaaggcca ccgcatgaag  1380
ctgctgctgc tgggcaaggg cggacaggtc ggctgggagc tgcaacgcag cctcgcgccc  1440
ctgggcgaac tggtggcgct cgatttcgac agcaccgact tcaacgccga cttcagtcgc  1500
cccgagcagc tggccgagac agtgctgaag gtgcgccccg acgtcatcgt caatgccgcg  1560
gcgcacaccg cggtcgacaa ggccgagagc gagcccgagt tcgcgcgcaa gctcaacgcc  1620
acctcgcccg cgtggtggc cgaagccgcg cagcagatcg gcgcgctgat ggttcactac  1680
tcgaccgact acgtcttcga cggcagcggc agcaagccgt ggaaagaaga cgatgcgacc  1740
ggcccgctca gcgtctacgg cagcaccaag ctcgaaggcg agcaactggt ggcaaagcac  1800
tgtgcgaagc acctgatctt tcgcaccagc tgggtctatg ccgcgcgcgg cggcaacttc  1860
gccaagacca tgctgcgcat cgccaaggag cgcgacaagc tgaccgtcat cgacgaccag  1920
ttcggcgcgc ccaccggcgc ggaactgctg gccgacatca ccgcgcacgc gattcgcgcg  1980
acgctgcagg acccgtccaa ggcgggctct tatcacgcgg tggccggtgg cgtgaccacg  2040
tggcacggct atgcgcgctt cgtgatcgag caggccaggc ggcgcgt ggaactggga     2100
gccggccccg aagcggtcga gcccgtgccc accacggcat tcccgacgcc ggccaggcgg  2160
ccgcacaact cgcgcctgga caccaccaag ctgcaatcga ccttcggcct cgtgctgccc  2220
gagtggcagt ccggcgtcgc ccgcatgttg cgcgaaacct tctgatattc gcagagcaag  2280
agagacacga acaccccatg accaagacga cgcaacgcaa aggcatcatc ctcgccggtg  2340
gctcgggcac ccgcctgcac cccgcgacgc ttgccatgag caaacaactg ctgccggtgt  2400
acgacaagcc gatgatctat tacccgctga gcacgctgat gctgggcggc atgcgcgaca  2460
tcctgatcat cagcacgccg caggacacgc gcgtttcca gcaactgctg ggggatggca  2520
gccaatgggg catcaacctg cagtacgcgg tgcagccgga cccggatggt ctggcgcagg  2580
cgttcatcat cggtgacaag ttcgtgggca acgaccccga tgcgctggtg ctgggggaca  2640
acatcttcta tggccacgac ttcgcccatc tgctggccga tgccgacgcc aagacctcgg  2700
gtgcgacggt gttcgcctac cacgtgcacg accccgagcg ctacgcgtg gtggccttcg  2760
atgccaaggg cagggcgagc agcatcgaag aaaagccgct caagcccaag agcagctatg  2820
cggtcacggg cctctacttc tacgacaacc aggtcgtcga catcgccaag gccgtgaagc  2880
cgagcgcgcg cggcgaactc gagatcaccg cggtcaacca ggcgtatctc gacctcgacc  2940
agctgaacgt gcagatcatg cagcgcggct atgcgtggct cgataccggt acgcacgaca  3000
gcctgctgga agcggggcag ttcattgcca cgctcgagca ccgccagggg ctgaagatcg  3060
catgcccgg a agagatcgca tggcgcaatg gcttcatctc aaccgagaca ctcgaaaagc  3120
tcgcggcgcc gctggaaaag agcggctacg gcaagtacct caagcacctg ctgaacgacg  3180
aggtgcgctc gtgaaggcca cgcccacctc gattcctgac gtgctcgtga tcgagccgaa  3240
ggtgtttggc gatgcacggg gcttcttctt cgaaagcttc aaccagaagg ccttcgacga  3300
agcgatcggc aagcatgtcg acttcgtgca ggacaaccat tcgcgatcgg ccaaggtgt   3360
gctgcggggg ctgcattacc aggtccagca gccgcaaggc aagctcgtgc gggtggtgcg  3420
tggtgcggtg ttcgacgtgg ccgtcgacat ccgcaagtcg tcgccgactt tggcaaatg   3480
ggtgggtgtc gagttgaacg aagacaacca caagcagctc tggtgccgg caggattcgc   3540
gcacggtttc ctggtgtga gcgagaccgc ggaattcctg tacaagacca ccgactacta  3600
cgcgccccgcc cacgagccgg cgattgtctg aacgaccccg ctgtcggta ttcgatggcc  3660
ggatgtgggg ggcaccgg tcctgtcgaa aaggacgaa gacgggtgtc ttctgcaagc    3720
ggcagaggtt ttctagtgtc ctttcgtcag atagcggggc ggcttcgcgt atcgggatcc   3780
cgcgttgagc ccgcaagagt gcccgagag ggggggcgaa aaactcacaa cgccactgcc   3840
tcgagcaaac gtgcgtctcg cagctttctg aagttgttgc accttctttt ttttctctt   3900
acatcttga aatgatttg aaaatccgcg cgatcgcat gcatgctgct ggaatcacc     3959
```

| SEQ ID NO: 3 | moltype = DNA  length = 915 |
| FEATURE | Location/Qualifiers |
| source | 1..915 |
| | mol_type = genomic DNA |

```
                        organism = Variovorax paradoxus
SEQUENCE: 3
atgaatggca tgcatatcga ctcggtcgac ctcaatctgc tgcgcctgtt cgatgcggtc     60
taccgcgagc gcagcgtgag ccgcgccgcg gagtcgctgg gcctcacgca gcctgcggca    120
agccatgggc tgggacggct gcggctgctt tgaaaagacg cgctcttcac gcgtgccccg    180
ggcggcgtgg cgcccacgcc gcgcgccgac cggctcgcgg tggcggtgca ggcggcgctc    240
ggcacgatcg aagcggcgct gcacgagccc gatcgcttcg agcccaggt gtcgcgcaag     300
agctttcgta ttcacatgag cgacatcggc gaggggcgct tcctgcccgc gctgatggcg    360
cggctcggcg agctggcgcc cggcgtgcgg ctggagaccc tgccgctctt gcctgcggag    420
gttgcgcccg cactcgacag cggccgcatc gatttcgcct tcggctttct ctcgaccgtg    480
cgcgacacgc agcgcacgca tcttctgaaa gaccgctaca tcgtgctgct gcgcaagggc    540
catccctttg tgaagcgccg gcgcaagggg caggcgctgc tcgaggcgct gcaggagctc    600
gactacgtgg cggtgcgcac gcacgccgac acgctgcgca tcttgcagtt gctcaacctc    660
gaagacgcc tgcgcctcac gaccgagcac ttcatggtgc taccggccat cgtgcgcgcc    720
accgatctcg cggtggtgat gccgcgcaac atcgcgcgag ggtttgcgga ggagggcggc    780
tacgcgatcg tcgagccgcc gttttcgctg cgcgatttca gcgtgtcgct gcactggagc    840
aagcgcttcg agggcgaccc ggccaaccgt tggttgcggc aggtgatcac ggcgctgttc    900
tccgagcgcg gctga                                                     915

SEQ ID NO: 4              moltype = AA  length = 304
FEATURE                   Location/Qualifiers
source                    1..304
                          mol_type = protein
                          organism = Variovorax paradoxus
SEQUENCE: 4
MNGMHIDSVD LNLLRLFDAV YRERSVSRAA ESLGLTQPAA SHGLGRLRLL LKDALFTRAP     60
GGVAPTPRAD RLAVAVQAAL GTIEAALHEP DRFEPQVSRK SFRIHMSDIG EGRFLPALMA    120
RLGELAPGVR LETLPLLPAE VAPALDSGRI DFAFGFLSTV RDTQRTHLLK DRYIVLLRKG    180
HPFVKRRRKG QALLEALQEL DYVAVRTHAD TLRILQLLNL EDRLRLTTEH FMVLPAIVRA    240
TDLAVVMPRN IARGFAEEGG YAIVEPPFPL RDFSVSLHWS KRFEGDPANR WLRQVITALF    300
SERG                                                                 304

SEQ ID NO: 5              moltype = DNA  length = 7476
FEATURE                   Location/Qualifiers
source                    1..7476
                          mol_type = genomic DNA
                          organism = Variovorax paradoxus
SEQUENCE: 5
atgagtaccg tcgatcagct gggccgcacc gcccccctta cctcggggca gatggcgatg     60
tggctcggcg caaagttcgc gtcgcccgac accaatttca atctcgccga agccatcgac    120
atcgcaggcg agatcgaccc cgcgatcttc tggcggcca tgcgcaggt ggccgatgaa      180
gtcgaggcca cgcgcctgag cttcatcgat acccgcaag gccacgaca ggtcgtcgcg      240
cccgttttca ccggcgagat cccctacctc gacctgacg gcgagagcgt tccgcaggcg    300
gaggccgagc gctggatgca tgcggactac acccgcagca tcgacctcgc gcacgggcag    360
ctgtggctgt ccgcgctgat ccgcctcgcg cccgatcgcc acatctggta ccaccgcagc    420
catcacatcg cgctcgacgg cttcagcggc ggcctcatcg cacgccgctt cgccgacatc    480
tacaccgcga tggtcgacaa caacgcagcg gtgcccgaag actcgcgcct tgcaccgatc    540
tcgcagctgg ccgacgaaga acatgcctat cgcgagtccg gccgcttccc gcgcgaccgc    600
cagtactgga ccgagcgctt cgccgatgca cccgatccgt tgagcctcgc ctcgcaccgc    660
tcggtcaacg tcggtggcct cttcgcgcag acggtgcacc tgccggcggc cagcgtgcaa    720
gccctgcaga ccatcgcgca agagctcggc accacgctgc cgcaaatcct catcgccatc    780
accgcggcct acctgtaccg cgcaacgggc atcgaggaca tggcaatcgg catccccgtc    840
accgcgcgcc acaacgaccg catgcgccgc gtgcccgcga tggtggccaa cgcgctgccg    900
ctgcgcctgg cgatgcgcgc ggacctgccg attccggaac tgatccgcga agtcggccgg    960
cagatgcggc agatcctgcg gcaccagtcg tatcgctacg agcatttgcg cagcgacctc   1020
aacatgctgg tgaacaaccg gcagctcttc accaccgtgg tcaacgtcga gcccttcgac   1080
tacgacttcc gctttgcggg ccatgccgcg aagccgcgca acctctcgaa cggcacggcc   1140
gaggacctcg gcatcttcct gtacgagcgc ggcaacgggc aggacctgca gatcgacttc   1200
gacgccaacc ccgcggttca caccgcagag gaactggccg atcaccagcc ccggctgctt   1260
gccttcatcg acgccgtgat ccgcctgccg ttgcaggccg tcggccagat cgacctgctc   1320
ggtgccgaag agcggcagca attgctggtc gagtggaacg cacggccca cgccgtgccc   1380
gacacccatc tcaccgcgtt gatcgaacgg cagctcgcag ccgatccgca agccatcgca   1440
ttgcgcttcg acgcgaggc gatgaacaac gaagaactga accgccgcgc caaccgtctc   1500
gcccacctgc tgcgcgcacg cggcgctggc ccggagccga ccgtgccgct cgcgatcccg   1560
cgttcgatgc acctgatgat tgccttgctc gccacgttga agaccggcgc ggcctacctg   1620
ccggtcgatc cggatttccc ggcggaccgc atcgccttca tgctcggcga tgcgcagccc   1680
gtgtgcctcg tcacgaccga agccctcgcg gagtcgctgc cggcagccgc cccacattg   1740
ctgctcgatg tagcgcaaac gattgcggat ctggagagtt gcaacgacac caacccgggc   1800
atcgcgatcg accccttcgca tccggcctat gtgatctaca cctcgggctc gaccggcatc   1860
cccaagggtg cggtcgtgtc gcaccgcgcc atcgtcaacc gcctgcgctg gatgcaggac   1920
cgctacggcc ttcaggccga cgccgcgtg ctgcagaaga cgcttccag cttcgacgtg    1980
tcggtgtggg agttcttctg gccgctgatc acggtgcca cgctggtgct tgcgaaaccg   2040
ggcggccaca aggatgcggc ctacctcgcg gggctgatcg cggaggaggg catcaccacg   2100
atccacttcg tgcctccgat gctcgaggtc ttcctgctca acgacgcg gctgccatgc   2160
accacgctgc gccgcgtgat ctgcagcggc gaagccttgt cgcccgcgct gcaatcgag   2220
ttccagcagc acctctcgtg cgagctgcac aacctctacg gtccgaccga ggcggcggtc   2280
gacgtcacct cgtgggagtg cgaacgcacg gacgacgcag aagcctcgag cgttcccatc   2340
ggccgcccga tctggaacac ccagatgcac gtgctcgaca gcggcctgca gcccgtgccg   2400
gccggcgtga ctgcgagct gtacatcgcg ggcgtcggcc tcgcacgcgg ctacctcaag   2460
```

```
cgcccgttgc tgagcgccga gcgtttcatc gccaacccct acggcacacc cggcagccgc  2520
atgtaccgca ccggcgacct cgcgcgctgg cgcaaggacg gcagccttga cttcctcggc  2580
cgcgccgacc agcaggtgaa gatccggggc ctgcgcatcg agccgggaga gatcgaatcc  2640
gtgctgctgc agcatccgca agtcgcgcag gccgccgtgg tggcgcgcga agacgtaccg  2700
ggcgaaaagc gtctcgtggc ctacgtcgtt gcgacgaacg ctgccgatcc gcaagcggcc  2760
gaactgcgca cgcgcctcgc gcaatcgctg cccgagtaca tggtgccttc ggccttcgtc  2820
agcctcccgt cgctgccgct cggacccagc ggcaagctcg accgcaaggc gctgccgccc  2880
cccgaagtga aggccgccac gccgtacgcc gcgccgcgca cgccgaccga aaagatcctg  2940
gccggcctct gggccgagac gctgcatttg ccgcgcgtcg gtgtcaacga caacttcttc  3000
gaactcggcg gccactcgct gatgatcgtg cagctcatgt cgatgatccg gcagcaattc  3060
atgatcgacc tgccggtcga cacgctgttc caggtctcca ccatcgcggg ccttgccgag  3120
ctgctcgacc aggaatcggt cgcccgtccg agcctgactc cgatgccgcg ccccgcgcgc  3180
attccgctgt ccttcgcgca gcgccgcctg tggctgatga accagctcga aggcgcgaac  3240
ccggcctaca acatgccgct cgcgctgcgc ctgtcggggtg tgctcgatcg caccgcattg  3300
catgcggcgc tcggcgacct ggtgcagcgc cacgagagcc tgcgcacggt ctacccgaac  3360
gaagacgggc tgccgtacca gcacatcctc gacggcgcgg atgcgcgtcc ggcggtgatc  3420
gaggccgaca gcagcgaaga agaaatcgcg gcgcagcttc acgccgctgc gggccatgcc  3480
ttcgatctcg gcagcgcggc gcccttgcgc tgtctacctg tcaagctcgc cggcgacgaa  3540
cacgtgctgc tgctgctcac gcaccacatt gccggcgatg gcgcctcgct gctgccgcta  3600
gcgcgcgaca tcagcgtggc ctatgccgcg cgctgcgaag gcaaggcgcc gggctgggag  3660
ccgctgccgc tgcaatacgc cgactacgcg ctgtggcagc aggagctgct cggcagcgaa  3720
gacgatgccg agagcatggc cggccgccag cgtgagttct ggcgttcctc gcgaagcgaa  3780
ctgcccgagc aactggcgct gcccgtcgac cacgcacggc cgctcgtgcc gacctaccgc  3840
ggcgatgtgg tcccgctgca gattccgtcg catgtgcatg aacgcatcct gcaactggcg  3900
cgcgacgggc aggccagcgt cttcatggtg ctgcaggccg cactcgcggg cctcctgagc  3960
cgcctcggcg cgggcgacga catcgtcatc ggcagcccgc tcgcggggcg cagcgaccat  4020
gcgctggacg aactcatcgg ctgcttcgtc aacacgctgg tgctgcgcac tgacacctcg  4080
ggccagccga gctgcgcga gctggtctcg cgcgtgcgcg ccaccaacct cgcggcctat  4140
gcgaaccagg agtttccgta cgaccgcctc gtggagctgc tgcgtccggg ccgctcgcgc  4200
gccaacctgc cgctgttcca ggtcttccag gcgcttccag ggacgagccg ctcgtcgttc  4260
agcctgccgg gcctgtcgat cgcgccgcag ccggtggcca tcgacaccgc gaagttcgca  4320
ctgtcgttca tcctcggcga gcaacgcggt gccgatggcc tgccgggcgg catctccggc  4380
ggcatccagt acagcaccga cctgttcgag cgcagcacgg tcgaggccat gggcgcgcgg  4440
ctggtgcgtt tgctggaaga ggcctgcgag gcgcccgacg atgcggtgag tggcctcgcc  4500
atcctgagcg cggaagaaac cgaccgcctg ctgtccgact cacgcgcgac cacgcgcgac  4560
cttgcgccgc tctcgttcgc cgacatggtg gcctcgcatg ccgcggagcg cccgcttgca  4620
gatgcagtgg tgctcgacga cgcgaccgtc agctacgccg aactcgatgc acgcgccaac  4680
cggctctcgc acctgctgcg tgcgcaaggc atcggggttg cgccatcgt cgcgacagtg  4740
ctgccgcgtt cgctcgacct catcgcggcg cacttgccca tcgtgaaggc cgtgcgtgag  4800
tacctgccca tcgaccccaa ccacatggcc gcgcgcagcg ccttcgtgtt cgaggaggcc  4860
gcgcccgccg cggtgctgac gcacgatgcg ctgttgcccg agctggtcgg cgttccccgc  4920
tgcatcgcgc tcgacagcga cagcatggtt gccgcgctgg ccatccagtc ggatacgccg  4980
ctggtgcatg cggccaatcc acaggatgcc gcctacctca tctacacctc cggctccacc  5040
ggcatgccca agggcgtggt ggtgccgcat gcggggcctgg gcagcctcgg caccgcgatg  5100
gcggagcggc tcgtcatcgg ccacggctcg cgcgtgctgc agttctcctc cagcggcttc  5160
gacgcgtcgg tgatgaccca gctgatggcc tttggcgccg gtgccgcgct ggtggtgccg  5220
ggccggacga aactgctcgg cacggagctg gccgatctgc tcgagaagca ggccgtgagc  5280
cacgcgctga ttccgccccgc cgcgctcgcg accctgccgc acggcgagtt cccgcacctg  5340
cagacgctgg tggtcggcgg cgatgcctgc accgccgcgc tggcggcgaa gtggtcgcaa  5400
ggccgccgca tgatcaacgc ctacggcccg accgagatca ccatctgcgc gagcatgagc  5460
gcgccgatga cggccgagga gttgcccttcc atcgggcagc cgatctgaag cacgcggatg  5520
tatgtgctcg acagcgccct gcaaccggtg ccgccgggtg tcgcgggcga gctctacatc  5580
gccggcagcg gcgtggcgcg cggctatctc aaccggccgg cattgagtgc ggaacgcttc  5640
atcgccgacc gcatggcgc gcccggcagc cgcatgtacc gcagcggcga cctcgcacgc  5700
tggcgccgca acggcacgct cgacttcctc ggccgcgccg accagcaggt gaagatccgg  5760
ggcttccgca tcgagccggg cgagatcgaa tccgtgctgc tcaagcaccc gttgatcacg  5820
caggccgccg tgatcgcccg cgaggacgtg cccggcgaga agcgcctggt cgcctacttc  5880
gtcgccggtt ccgagccgca gcccaccgag ctgcgcgccc acatggcgca ggccttgccc  5940
gactacatgg tgccttcggc cttcgtgcgc ctgccgtcgc tgccgctcac gcaaaagcgc  6000
aagctcgaca agaaggcgct gccggtgccc gaccagcagc ccgccgcgct gtacgtggag  6060
ccccgcacgc cgaccgagaa actgctcgcg ggcctctggt ccgagacgct gcacctggag  6120
cgtgtcggca tccacgacaa cttcttcgag atcggcgggc attcgctcat ggcgatccag  6180
ctgggcatgc gcatccgcca gcaggtcgcg cgggacttcc cgcacgccga ggtctacaac  6240
cgcccgacga ttgccgaccg gccgcctgg cgcgacaacg aaggcggcac ggtcgaggcg  6300
ctggacctgt cgcgcgagct cgacctgccc gcgcacatcc gcccgcaggc cactgcaccg  6360
aagctcgcac cgcgccgcgt gttcctcacc ggcgcgagcg gcttcgtcgg cagtcacctg  6420
ctggccgcgc tgttgcgcga caccgcggcc tgcgtggtct gccacgtgcg cgcgcccgac  6480
gagcaggccg gcgagcagcg cctcaagcgc acgcgtggccc agcgccagct cggtgcgatc  6540
tgggacaacg cgcgcatcaa ggtcgtgacc ggcgacctcg gcaagccgcg cctgggcctc  6600
gatgacgctg ccgtgcaact ggtgcgcgac ggctcgacg ccatctacca ctgcgccgcg  6660
caggtcgact tcctgcatcc ctacgcgagc ctcaagcccg cgaacctcga cagcgtggtc  6720
acgctgctcg aatggacggc gcaggggcgc gcgaagagca tgcactacgt ctccacgctg  6780
gctgtgatcg accagaacaa caaggaagac accatcaccg agcaatcggc gctggcctca  6840
tggagcggc tggtcgacgg ctacagccag agcaagtggg tcggcgatgc gctggcccgc  6900
gaggcgcagg cgcgcggcat gccggtggcg atctaccggc tggggcagt caccggcgac  6960
cacacgcacg cgatctgcaa tgccgacgac ctgatctggc gcgtggcca tctctatgcc  7020
gacctggaag cgattcccga tatggacctg ccgctcaacc tcacaccggt ggacgacgtg  7080
gcgcgcgcca tcctcggcct tgcggcgcag gaggcctcgt ggggcaggt gttccacctg  7140
atgagccagg cggcgctgcg ggtgcgcgac attccgcacg tcttcgagcg catgggcatg  7200
```

```
cggctggagc cggtcgggct ggagccctgg ctgcagcgcg cgcatgcacg gctggccgtc   7260
gcgcatgacc gcgaccggcc cgcggtgctc gccatcctcg accgctacga caccacggcc   7320
acgccgccgc aggtgagcgg cgcggccacg catgcgcagc tcgaggccat cggcgcgccg   7380
atccgcccgg tggaccgcga cctgctgcag cgctacttcg tcgacctggg catcgacacc   7440
aaggcgcgcc gcgccctgga aaccaccact tcatag                             7476

SEQ ID NO: 6            moltype = AA   length = 2491
FEATURE                 Location/Qualifiers
source                  1..2491
                        mol_type = protein
                        organism = Variovorax paradoxus
SEQUENCE: 6
MSTVDQLGRT APLTSGQMAM WLGAKFASPD TNFNLAEAID IAGEIDPAIF LAAMRQVADE    60
VEATRLSFID TPQGPRQVVA PVFTGEIPYL DLSGESDPQA EAERWMHADY TRSIDLAHGQ   120
LWLSALIRLA PDRHIWYHRS HHIALDGFSG GLIARRFADI YTAMVDNNAA VPEDSRLAPI   180
SQLADEEHAY RESGRFPRDR QYWTERFADA PDPLSLASHR SVNVGGLLRQ TVHLPAASVQ   240
ALQTIAQELG TTLPQILIAT TAAYLYRATG IEDMAIGIPV TARHNDRMRR VPAMVANALP   300
LRLAMRADLP IPELIREVGR QMRQILRHQS YRYEHLRSDL NMLVNNRQLF TTVVNVEPFD   360
YDFRFAGHAA KPRNLSNGTA EDLGIFLYER GNGQDLQIDF DANPAVHTAE ELADHQRRLL   420
AFIDAVIRLP LQAVGQIDLL GAEERQQLLV EWNDTAHAVP DTHLTALIEA QLAADPQAIA   480
LRFDGEAMNN EELNRRANRL AHLLRARGAG PERTVALAIP RSMDLMIALL ATLKTGAAYL   540
PVDPDFPADR IAFMLGDAQP VCLVTTEALA ESLPAAAPTL LLDVAQTIAD LESCNDTNPG   600
IAIDPSHPAY VIYTSGSTGM PKGAVVSHRA IVNRLRWMQD RYGLQADDRV LQKTPSSFDV   660
SVWEFFWPLI DGATLVLAKP GGHKDAAYLA GLIAEEGITT IHFVPSMLEV FLLEPTAGAC   720
TTLRRVICSG EALSPALQSQ FQQHLSCELH NLYGPTEAAV DVTSWECERT DDAEASSVPI   780
GRPIWNTQMH VLDSGLQPVP AGVTGELYIA GVGLARGVLK RPLLSAERFI ANPYGTPGSR   840
MYRTGDLARW RKDGSLDFLG RADQQVKIRG LRIEPGEIES VLLQHPQVAQ AAVVAREDVP   900
GEKRLVAYVV ATDAADPQAA ELRTRLAQSL PEYMVPSAFV SLPSLPLGPS GKLDRKALPP   960
PEVQAATPYA APRTPTEKIL AGLWAETLHL PRVGVNDNFF ELGGHSLMIV QLMSMIRQQF  1020
MIDLPVDTLF QVSTIAGLAE LLDQESVARP SLTPMPRPAR IPLSFAQRRL WLMNQLEGAN  1080
PAYNMPLALR LSGVLDRTAL HAALGDLVQR HESLRTVYPN EDGLPYQHIL DGADARPAVI  1140
EADSSEEEIA AQLHAAAGHA FDLGSAAPLR VYLFKLAGDE HVLLLLTHHI AGDGASLLPL  1200
ARDISVAYAA RCEGKAPGWE PLPLQYADYA LWQQELLGSE DDAESMAGRQ REFWRSSLSD  1260
LPEQLALPVD HARPLVPTYR GDVVPLQIPS HVHERILQRA RDGQASVFMV LQAALAGLLS  1320
RLGAGDDIVI GSPVAGRSDH ALDELIGCFV NTLVLRTDTS GQPSLRELVS RVRATNLAAY  1380
ANQEFPYDRL VELLRPGRSR ANLPLFQVML GFQGTSRLSF SLPGLSIAPQ PVAIDTAKFD  1440
LSFILGEQRG ADGLPGGISG GIQYSTDLFE RSTVEAMGAR LVRLLEEACE APDDAVSGLA  1500
ILSAEETDRL LSDWSGRTRD LAPLSFADMV ASHAAERPLA DAVVLDDATV SYAELDARAN  1560
RLSHLLRAQG IGVGAIVATV LPRSLDLIVA HLAIVKAGAA YLPIDPNHMA ARSAFVFEEA  1620
APAAVLTHDA LLPELVGVPR CIALDSDSMV AALAIQSDTP LVHAANPQDA AYLIYTSGST  1680
GMPKGVVVPH AGLSLGTAM  AERLVIGHGS RVLQFSSSGF DASVMDQLMA FGAGAALVVP  1740
GPEQLLGTEL ADLLEKQAVS HALIPPAALA TLPHGEFPHL QTLVVGGDAC TAALAAKWSQ  1800
GRRMINAYGP TEITICASMS APMTAEELPS IGQPIWNTRM YVLDSALQPV PPGVAGELYI  1860
AGSGVARGYL NRPALSAERF IADPHGAPGS RMYRSGDLAR WRADGTLDFL GRADQQVKIR  1920
GFRIEPGEIE SVLLKHPLIT QAAVIAREDV PGEKRLVAYF VAGSEPQPTE LRAHMAQALP  1980
DYMVPSAFVR LPSLPLTQSG KLDKKALPVP DQQPAALYVE PRTPTEKLLA GLWSETLHLE  2040
RVGIHDNFFE IGGHSLMAIQ LGMRIRQQVR ADFPHAEVYN RPTIADLAAW LDNEGGTVEA  2100
LDLSRELDLP AHIRPQATAP KLAPRRVFLT GASGFVGSHL LAALLRDTAA CVVCHVRAPD  2160
EQAGEQRLKR TLAQRQLGAI WDNARIKVVT GDLGKPRLGL DDAAVQLVRD GCDAIYHCAA  2220
QVDFLHPYAS LKPANVDSVV TLLEWTAQGR AKSMHYVSTL AVIDQNNKED TITEQSALAS  2280
WSGLVDGYSQ SKWVGDALAR EAQARGMPVA IYRLAGDTGD HTHAICNADD LIWRVAHLYA  2340
DLEAIPDMDL PLNLTPVDDV ARAILGLAAQ EASWGQVFHL MSQAALRVRD IPHVFERMGM  2400
RLEPVGLEPW LQRAHARLAV AHDRDLAAVL AILDRYDTTA TPPQVSGAAT HAQLEAIGAP  2460
IRPVDRDLLQ RYFVDLGIDT KARRALETTT S                                2491

SEQ ID NO: 7            moltype = DNA   length = 1320
FEATURE                 Location/Qualifiers
source                  1..1320
                        mol_type = genomic DNA
                        organism = Variovorax paradoxus
SEQUENCE: 7
atggcacgct atctcatcgc agcaaccgcc ttgccgggac acgtcctgcc gatgctggcc    60
atcgcgcagc atctggtgaa ccaggggcac gaggtgcggg tgcacaccgc gagccagttc   120
agggcgcagg ccgaggcgac cggtgcgggc ttcacgcccc tcgagcgcag gatcgacttc   180
gactaccgcg acctggacaa gcgctttccc gagcgccagc gcatcgcctc ggcgcatgcg   240
cagctgtgct tcggcctgaa gcacttcttt gccgatgcga tggccgcgca gatgcgggc   300
ctgcaatcga tcctcgaaga cttcgaggcc gatgccatcg tggtcgacac gatgttctgc   360
ggcactttcc cgctgctgct aggcaaggag cgcgaagacc gcccggccat cgtcggcatc   420
ggcatctgc cgctgccgct ctcgagctgc gacaccgcct tcttcggcac gcgcgtgcag   480
ccgtcgtcca cgccggaagg gcgggtgcgc aacaaggcgt tgaacgccaa cctcaaacag   540
gcgatgttcg cgaggtgcag acgctacttt gacacgctgc tcgcgcgttc gggcctggcc   600
gcgctgcccg atttcttcgt cgatgcgatg gtgaagctgc ccgatcttta cctgcagctc   660
accgcgcctt cgttcgaata cccgcgcagc gacctgcccg tcggtgcga tttcgtcggc   720
ccgctcgtcc gagacgcttc acgccgcctc agtggtgtga cgagctggac   780
gacggccgc cggtcgtgct ggtcacgcag ggcacgctgg ccaaccgaa tccgtcgcag   840
ctgatcggcc cgacgctgca ggcctggcc ggcgacaaga acatcctcgt catcgccacc   900
accggcggcc ccggtgccgcc cgccctgacg gtgaacctgc cgccaacgc ccgcgtggtg   960
ccgttcctgc cctacgaccg gctgctgccc aagctgcacg cgatggtcac caacggcggc  1020
tacggctcgg tcaaccatgc attgagcctc ggtgtgccgc tggtggtggc cggcacctcc  1080
```

```
gaagagaagc cgagatcgc cgcgcgcgtg gcctggtcgg gcgcgggcat caacctcgcc    1140
accggccagc cgaccgcgcg ccaggtcggc gacgcggtgc gcaaggtact gggcaactcg    1200
acctatcgcc agcgtgcggc ggtgctgcgt gaggacttcg cttgccatcg cgcgctgacc    1260
ggcatcgccg gcgccctcga ggcacttctg caaaccttcg catccgcgga aatggcttga    1320

SEQ ID NO: 8              moltype = AA   length = 439
FEATURE                   Location/Qualifiers
source                    1..439
                          mol_type = protein
                          organism = Variovorax paradoxus
SEQUENCE: 8
MARYLIAATA LPGHVLPMLA IAQHLVNQGH EVRVHTASQF RAQAEATGAG FTPFERTIDF     60
DYRDLDKRFP ERQRIASAHA QLCFGLKHFF ADAMAAQHAG LQSILEDFEA DAIVVDTMFC    120
GTFPLLLGKE REDRPAIVGI GISALPLSSC DTAFFGTALP PSSTPEGRVR NKAMNANLKQ    180
AMFGEVQRYF DTLLARSGLA ALPDFFVDAM VKLPDLYLQL TAPSFEYPRS DLPASVHFVG    240
PLLSPASRDF TPPEWWHELD DGRSVVLVTQ GTLANQNPSQ LIGPTLQALA GDKNILVIAT    300
TGGPVPPALT VNLPANARVV PFLPYDRLLP KLHAMVTNGG YGSVNHALSL GVPLVVAGTS    360
EEKPEIAARV AWSGAGINLA TGQPTARQVG DAVRKVLGNS TYRQRAAVLR EDFACHRALT    420
GIAGALEALL QTFASAEMA                                                 439

SEQ ID NO: 9              moltype = DNA   length = 213
FEATURE                   Location/Qualifiers
source                    1..213
                          mol_type = genomic DNA
                          organism = Variovorax paradoxus
SEQUENCE: 9
atgagcaacc cgttcgacga caagaacgcc agcttccagg tgctggtgaa cgacgagggc     60
cagcactcgc tgtggcccgc cttcatcgcc gtgcccgccg gctggcaggt ggcgctggcg    120
ccgaccgacc gcgacgcctg cagcgcctac atcgcggcga actggcagga catgcgcccg    180
cgttcgctgg tggtggccac ggcggccggc tga                                 213

SEQ ID NO: 10             moltype = AA   length = 70
FEATURE                   Location/Qualifiers
source                    1..70
                          mol_type = protein
                          organism = Variovorax paradoxus
SEQUENCE: 10
MSNPFDDKNA SFQVLVNDEG QHSLWPAFIA VPAGWQVALA PTDRDACSAY IAANWQDMRP     60
RSLVVATAAG                                                            70

SEQ ID NO: 11             moltype = DNA   length = 969
FEATURE                   Location/Qualifiers
source                    1..969
                          mol_type = genomic DNA
                          organism = Variovorax paradoxus
SEQUENCE: 11
atgtccttcc cgttcggtgc cgtcgtcgtc acctatttcc cgaccggcga gcaagtggcg     60
aacctccatt cgctggcggc ctcgtgtccg cacctctgcg tggtcgacaa cacgccgcag    120
gtgggcgatt ggcatgcggc gctcgtcgat gcgggcgttt cggtgctgca caacggcaac    180
cgcggcggca tcgcgggcgc cttcaaccgc ggcatcatcg acctcgaagc gcggggcgcc    240
gaactcttct tcctgctcga ccaggattcg aagctgccgg gctactttga tgccatg       300
tgcgaggctg cgatggtggc ccgggagcgg aagggcgagg gcaatggtga ggaagacgcg    360
gccttcctga tcgcccgcct cgtccacgac acgaacctgg acgcgctgat cccgcaattc    420
ggcctccagg gcaaacgcgt ctaccagttc gacctgcggc agcccttcac cgagccgctg    480
atgcgctgcg ccttcatgat ttcctcgggc tccctgattt cgcgcggcgc ctgggccagg    540
atcggccggt tcgacgagcg ctatgtgatc gaccacgtgg acaccgacta ctgcatgcgt    600
gccctgggtc gcggcgtgcc gctctacctg aatccgcacg tcgtgctgcg caccagatt    660
ggcgacatcc gtgcccggtc gctgttcggc tggaagatcc acttcatcaa ctacccggcc    720
gcgcggcgct actacatcgc gcgcaatgcc atcgatctct cgcgcgcgca tgtcgcgcg    780
tttcccgcga tcctgttcat caacgtttac acgctcaagc agatcctgcc gatgctgatg    840
ttcgagcgcg accgcttcaa gaagaccatc gcgctgatgc tcggctgctt cgatggcctg    900
ttcgggcggc tcgggggcct cggcgaggtg catccgcgga tggcaaata cctgggccgc    960
agcgattga                                                            969

SEQ ID NO: 12             moltype = AA   length = 322
FEATURE                   Location/Qualifiers
source                    1..322
                          mol_type = protein
                          organism = Variovorax paradoxus
SEQUENCE: 12
MSFPFGAVVV TYFPTGEQVA NLHSLAASCP HLCVVDNTPQ VGDWHAALVD AGVSVLHNGN     60
RGGIAGAFNR GIIDLEARGA ELFFLLDQDS KLPPGYFDAM CEAAMVARER KGEGNGEEDA    120
AFLIGPLVHD TNLDALIPQF GLQGKRVYQF DLRQPFTEPL MRCAFMISSG SLISRGAWAR    180
IGRFDERYVI DHVDTDYCMR ALGRGVPLYL NPHVVLRHQI GDIRARSLFG WKIHFINYPA    240
ARRYYIARNA IDLSRAHVRA FPAILFINVY TLKQILPMLM FERDRFKKTI ALMLGCFDGL    300
FGRLGGLGEV HPRMGKYLGR SD                                             322

SEQ ID NO: 13             moltype = DNA   length = 1260
FEATURE                   Location/Qualifiers
```

-continued

| | | |
|---|---|---|
| source | 1..1260<br>mol_type = genomic DNA<br>organism = Variovorax paradoxus | |

SEQUENCE: 13

```
ttgaccgcca cccttccagc gccgcgcgta cgccgcgccg cgctcgcctt catcttcgtc    60
acggtgctga tcgacttcat ggcgttcggc ctgatcctgc ccggcctgcc gcacctggtg   120
gagcggctgg ccggcggcag cacggtaacg cgggcgtact ggatcgctgt gttcggcacc   180
gcgttcgcgg cgatccagtt cgtgagctcg ccgatccagg gcgcgctgtc cgaccgcttc   240
gggcggcggc cggtgatcct gctgtcgtgc ttcggcctcg gcgtggattt cgtgttcatg   300
gccctggccg acagcctgcc gtggctgttc gtcggccgag tggtctccgg cgtgttctcg   360
gccagcttca ccatcgccaa tgcctacatc gccgatgtga cgctgccgga ggagcgcgcc   420
cgcagctacg gcatcgtggg ggccgcgttc ggcatgggcc tggtgttcgg gccggtgctc   480
ggcgggcaac tgagccacat cgatccgcgc ctgccgttct tggtcgcggc cggcttgacg   540
ctgctcagct tctgctacgg atggttcgtg ttgcccgaat cgctgccgcc cgagcggtcg   600
gcccgcaagt tcgactggtc gcatgccaat ccggttggga cgctggtgct gctcaagcgc   660
tatccgcagg tgttcggact ggcggcgtg atcttcctcg tgaacctggc tcagtacgtc   720
tatcccagcg tgttcgtgct gttcgccgac taccggtatc actggaagga agacgccgtg   780
ggctgggtgc tcggcgcggt gggcgtgctc agcgtgctcg tcaatgcgct gttgatcggc   840
ccgggcgtga agcgcttcgg cgagcgcgcc gccctgttgc tcggcatggg cttcggcgtg   900
ctcggcttcg tcatcatcgg gtttgccgac gctggatgga tcctcctggc cggggtgccg   960
ttcggcattc tgctggcgtt cgccggaccg gcggcgcagg cgctggtcac gctgcaggtc  1020
ggcaccgccg agcaggggcg catccagggg cgctcacca cctggtgc ggtggcgggt  1080
atcgtcgggc cggcgatgtt cgccggcagc ttcggttact tcatcggcgc ggacgcgccg  1140
gtgcacttgc ccggcgcgcc gttttcctc gctcgcgcgt tcctctgcat cggcacgctg  1200
atcgcgtggc gctacgcaca gccgaagccc gcgacggcag cggtgcccga gccgacctga  1260
```

| | | |
|---|---|---|
| SEQ ID NO: 14<br>FEATURE<br>source | moltype = AA length = 419<br>Location/Qualifiers<br>1..419<br>mol_type = protein<br>organism = Variovorax paradoxus | |

SEQUENCE: 14

```
MTATLPAPRV RRAALAFIFV TVLIDFMAFG LILPGLPHLV ERLAGGSTVT AAYWIAVFGT    60
APAAIQFVSS PIQGALSDRF GRRPVILLSC FGLGVDFVFM ALADSLPWLF VGRVVSGVFS   120
ASFTIANAYI ADVTLPEERA RSYGIVGAAF GMGLVFGPVL GGQLSHIDPR LPFWFAAGLT   180
LLSFCYGWFV LPESLPPERR ARKFDWSHAN PVGTLVLLKR YPQVFGLAAV IFLVNLAQYV   240
YPSVFVLFAD YRYHWKEDAV GWVLGAVGVL SVLVNALLIG PGVKRFGERR ALLLGMGFGV   300
LGFVIIGFAD AGWILLAGVP FGILLAFAGP AAQALVTLQV GTAEQGRIQG ALTSLVSVAG   360
IVGPAMFAGS FGYFIGADAP VHLPGAPFFL AAAFLCIGTL IAWRYAQPKP ATAAVPEPT   419
```

| | | |
|---|---|---|
| SEQ ID NO: 15<br>FEATURE<br>source | moltype = DNA length = 1080<br>Location/Qualifiers<br>1..1080<br>mol_type = genomic DNA<br>organism = Variovorax paradoxus | |

SEQUENCE: 15

```
atgatcctgg taaccggcgg cgcaggcttc attggcgcca atttcgtact cgactggctc    60
gcacagagcg atgaaccggt cgtgaaccta gacaagctga cctacgcggg caacctcgag   120
acgctcgcat cgctcaagga caaccccgaa gcacatcttcg tgcagggcga catcggcgac   180
agcgcgctgc tcgaccgcct gctggccgag cacaagccgc gtgccgtggt caacttcgcg   240
gccgaatcgc acgtcgaccg ctcgatccac ggccccgaag acttcgtgca gaccaacgtg   300
ctgggcaccct tccgcctgct cgaatccgtg cgcggtttct ggaatgccct gccggccgac   360
cagaaggccg ccttccgctt cctgcatgtg tcgaccgacg aggtctacgg ctcgctctcc   420
aagaccgacc cggccttcac cgaagagaac aagtacgagc ccaacagccc gtactcggcc   480
agcaaggccg ccagcgacca cctcgtgcgc gcctggcacc acacctacgg cctgccggtg   540
gtcaccacca actgctcgaa caactacggg ccgttccact ccccgagaa gctcattccc   600
ctgatgatcg tcaacgcgct ggcgggcaag ccgctgcccg tgtacggcga cggcatgcag   660
gtgcgcgact ggctctacgt gaaggaccac tgcagcgcca tccgccgcgt gctcgaagcc   720
ggcaagctcg gcgagaccta caacgtgggc ggctggaacg agaagcccaa catcgagatc   780
gtcaacaccg tctgcgcgct gctcgacgag ctgagcccca aggccggcgg caagcgtac   840
aaggaacaga tcacctatgt gaccgaccgc cccggccacg accgccgcta cgcgatcgac   900
gcacgcaagc tcgagcgcga actcggctgg aaacctgccg agaccttcga cagcggcatc   960
cgcaagacgg tcgagtggta cctcgcgaac ggcgagtggg tgcgcaacgt gcaaagcggc  1020
gcgtaccgcg agtgggtcga agaacatac gacgccgcac cggcgaaggc caccgcatga  1080
```

| | | |
|---|---|---|
| SEQ ID NO: 16<br>FEATURE<br>source | moltype = AA length = 359<br>Location/Qualifiers<br>1..359<br>mol_type = protein<br>organism = Variovorax paradoxus | |

SEQUENCE: 16

```
MILVTGGAGF IGANFVLDWL AQSDEPVVNL DKLTYAGNLE TLASLKDNPK HIFVQGDIGD    60
SALLDRLLAE HKPRAVVNFA AESHVDRSIH GPEDFVQTNV LGTFRLLESV RGFWNALPAD   120
QKAAFRFLHV STDEVYGSLS KTDPAFTEEN KYEPNSPYSA SKAASDHLVR AWHHTYGLPV   180
VTTNCSNNYG PFHFPEKLIP LMIVNALAGK PLPVYGDGMQ VRDWLYVKDH CSAIRRVLEA   240
GKLGETYNVG GWNEKPNIEI VNTVCALLDE LSPKAGGKPY KEQITYVTDR PGHDRRYAID   300
ARKLERELGW KPAETFDSGI RKTVEWYLAN GEWVRNVQSG AYREWVEKQY DAAPAKATA   359
```

| | | |
|---|---|---|
| SEQ ID NO: 17 | moltype = DNA length = 891 | |

| FEATURE | Location/Qualifiers |
|---|---|
| source | 1..891<br>mol_type = genomic DNA<br>organism = Variovorax paradoxus |

SEQUENCE: 17

```
atgaagctgc tgctgctggg caagggcgga caggtcggct gggagctgca acgcagcctc   60
gcgcccctgg cgaactggt ggcgctcgat ttcgacagca ccgacttcaa cgccgacttc   120
agtcgccccg agcagctggc cgagacagtg ctgaaggtgc gccccgacgt catcgtcaat   180
gccgcagcgc acaccgcggt cgacaaggcc gagagcgagc ccgagttcgc gcgcaagctc   240
aacgccacct cgcccggcgt ggtgccgaa gccgcgcagc agatcggcgc gctgatgggt    300
cactactcga ccgactacgt cttcgacggc agcgcagca agccgtggaa agaagacgat    360
gcgaccggcc cgctcagcgt ctacggcagc accaagctcg aaggcgagca actggtggca   420
aagcactgtg cgaagcacct gatctttcgc ccagctgggg tctatgccgc gcgcggcggc   480
aacttcgcca agaccatgct gcgcatcgcc aaggagcgcg acaagctgac cgtcatcgac   540
gaccagttcg gcgcgcccac cggcgcgaa ctgctggccg acatcaccgc gcacgcgatt    600
cgcgcgacgc tgcaggaccc gtccaaggcc gggctctatc acgcggtggc cggtggcgtg   660
accacgtggc acggctatgc gcgcttcgtg atcgagcagg ccaaggcggc gggcgtggaa   720
ctgaaggcgg gccccgaagc ggtcgagccc gtgcccacca cggcattccc gacgccggcc   780
aggcggccgc acaactcgcg cctggacacc accaagctgc aatcgacctt cggcctcgtg   840
ctgcccgagt ggcagtccgg cgtcgcccgc atgttgcgcg aaaccttctg a             891
```

| SEQ ID NO: 18<br>FEATURE<br>source | moltype = AA length = 296<br>Location/Qualifiers<br>1..296<br>mol_type = protein<br>organism = Variovorax paradoxus |
|---|---|

SEQUENCE: 18

```
MKLLLLGKGG QVGWELQRSL APLGELVALD FDSTDFNADF SRPEQLAETV LKVRPDVIVN    60
AAAHTAVDKA ESEPEFARKL NATSPGVVAE AAQQIGALMV HYSTDYVFDG SGSKPWKEDD   120
ATGPLSVYGS TKLEGEQLVA KHCAKHLIFR TSWVYAARGG NFAKTMLRIA KERDKLTVID   180
DQFGAPTGAE LLADITAHAI RATLQDPSKA GLYHAVAGGV TTWHGYARFV IEQAKAAGVE   240
LKAGPEAVEP VPTTAFPTPA RRPHNSRLDT TKLQSTFGLV LPEWQSGVAR MLRETF       296
```

| SEQ ID NO: 19<br>FEATURE<br>source | moltype = DNA length = 897<br>Location/Qualifiers<br>1..897<br>mol_type = genomic DNA<br>organism = Variovorax paradoxus |
|---|---|

SEQUENCE: 19

```
atgaccaaga cgacgcaacg caaaggcatc atcctcgccg gtggctcggg caccgcctg    60
caccccgcga cgcttgccat gagcaaacaa ctgctgccgg tgtacgacaa gccgatgatc   120
tattaccccg tgagcacgct gatgctgggc ggcatgcgcg acatcctgat catcagcacg   180
ccgcaggaca cgccgcgttt ccagcaactg tgggggatgg cgcaatg gggcatcaac      240
ctgcagtacg cggtgcagcc gagcccggat ggtctggcgc aggcgttcat catcggtgac   300
aagttcgtgg gcaacgaccc gagtgcgctg gtgctggggg acaacatctt ctatggccac   360
gacttcgccc atctgctggc cgatgccgac gccaagaccc cggtgcgac ggtgttcgcc    420
taccgctgc acgaccccga gcgctacggc gtggtgcct tcgatgccaa gggcagggcg    480
agcagcatcg aagaaaagcc gctcaagccc aagagcagct atgcggtcac gggcctctac   540
ttctacgaca accaggtcgt cgacatcgcc aaggccgtga agccgagcgc gcgcggcgaa   600
ctcgagatca cggcgtcaa ccaggcgtat ctcgacctcg accagctgaa cgtgcagatc    660
atgcagcgcg gctatgcgtg gctcgatacc ggtacgcacg acagcctgct ggaagccggg   720
cagttcattg ccacgctcga gcaccgccaa gggctgaaga tcgcatgccc cgaagagatc   780
gcatggcgca atggcttcat ctcaaccgag caactcgaaa agctcgcggc cgctggaa    840
aagagcggct acggcaagta cctcaagcac ctgctgaacg acgaggtgcg ctcgtga      897
```

| SEQ ID NO: 20<br>FEATURE<br>source | moltype = AA length = 298<br>Location/Qualifiers<br>1..298<br>mol_type = protein<br>organism = Variovorax paradoxus |
|---|---|

SEQUENCE: 20

```
MTKTTQRKGI ILAGGSGTRL HPATLAMSKQ LLPVYDKPMI YYPLSTLMLG GMRDILIIST    60
PQDTPRFQQL LGDGSQWGIN LQYAVQPSPD GLAQAFIIGD KFVGNDPSAL VLGDNIFYGH   120
DFAHLLADAD AKTSGATVFA YHVHDPERYG VVAFDAKGRA SSIEEKPLKP KSSYAVTGLY   180
FYDNQVVDIA KAVKPSARGE LEITAVNQAY LDLDQLNVQI MQRGYAWLDT GTHDSLLEAG   240
QFIATLEHRQ GLKIACPEEI AWRNGFISTE QLEKLAAPLE KSGYGKYLKH LLNDEVRS     298
```

| SEQ ID NO: 21<br>FEATURE<br>source | moltype = DNA length = 546<br>Location/Qualifiers<br>1..546<br>mol_type = genomic DNA<br>organism = Variovorax paradoxus |
|---|---|

SEQUENCE: 21

```
gtgaaggcca cgcccacctc gattcctgac gtgctcgtga tcgagccgaa ggtgtttggc    60
gatgcacggg gcttcttctt cgaaagcttc aaccagaagg ccttcgacga agcgatcggc   120
aagcatgtcg acttcgtgca ggacaaccat tcgcgatcgg ccaagggtgt gctgcggggc   180
ctgcattacc aggtccagca gccgcaaggc aagctcgtgc gggtggtgcg tggtgcggtg   240
ttcgacgtgc ccgtcgacat ccgcaagtcg tcgccgactt ttggcaaatg gtgggtgtc    300
gagttgaacg aagacaacca caagcagctc tgggtgccgc aggattcgc gcacggtttc    360
```

-continued

```
ctggtgttga gcgagaccgc ggaattcctc tacaagacca ccgactacta cgcgcccgcc    420
cacgagcgcg cgattgtctg gaacgacccc gctgtcggta ttcgatggcc ggatgtggga    480
ggggcaccgg tcctgtcgaa gaaggacgaa gacgggtgtc ttctgcaagc ggcagaggtt    540
ttctag                                                               546

SEQ ID NO: 22           moltype = AA  length = 181
FEATURE                 Location/Qualifiers
source                  1..181
                        mol_type = protein
                        organism = Variovorax paradoxus
SEQUENCE: 22
MKATPTSIPD VLVIEPKVFG DARGFFFESF NQKAFDEAIG KHVDFVQDNH SRSAKGVLRG      60
LHYQVQQPQG KLVRVVRGAV FDVAVDIRKS SPTFGKWVGV ELNEDNHKQL WVPAGFAHGF    120
LVLSETAEFL YKTTDYYAPA HERAIVWNDP AVGIRWPDVG GAPVLSKKDE DGCLLQAAEV    180
F                                                                   181

SEQ ID NO: 23           moltype = DNA  length = 1029
FEATURE                 Location/Qualifiers
source                  1..1029
                        mol_type = other DNA
                        organism = Variovorax paradoxus
SEQUENCE: 23
atgggcagca gccatcatca tcatcatcac agcagcggcc tggtgccgcg cggcagccat     60
atgtccttcc cgttcggtgc cgtcgtcgtc acctatttcc cgaccggcga gcaagtggcg    120
aacctccatt cgctggcggc ctcgtgtccg cacctctgcg tggtcgacaa cacgccgcag    180
gtgggcgatt ggcatgcggc gctcgtcgat gcgggcgttt cggtgctgca caacgcaac    240
cgcggcggca tcgcgggcgc cttcaaccgc ggcatcatcg acctcgaagc gcggggcgcc    300
gaactcttct tcctgctcga ccaggattcg aagctgccac ccggctactt cgatgccatg    360
tgcgaggctg cgatggtggc ccgggagcgg aagggcgagg gcaatggtga ggaagacgcg    420
gccttcctga tcgggccgct cgtccacgac acgaacctgg acgcgctgat cccgcaattc    480
ggcctccagg gcaaacgcgt ctaccagttc gacctgcgcg agcccttcac cgagccgctg    540
atgcgctgcg ccttcatgat ttcctcgggc tccctgattt cgcgcggcgc ctgggccgg    600
atcggccggt tcgacgagcg ctatgtgatc gaccacgtgg acaccgacta ctgcatgcgt    660
gccctgggtc gcggcgtgcc gctctacctg aatccgcacg tcgtgctgcg gcaccagatt    720
ggcgacatcc gtgcccggtc gctgttcggc tggaagatcc acttcatcaa ctacccggcc    780
gcgcggcgct actacatcgc gcgcaatgcc atcgatctct cgcgggcgca tgtgcgcgcc    840
tttcccgcga tcctgttcat caacgtttac acgctcaagc agatcctgcc gatgctgatg    900
ttcgagcgcg accgcttcaa gaagaccatc gcgctgatgc tcggctgctt cgatggcctg    960
ttcgggcggc tcgggggcct cggcgaggtg catccgcgga tgggcaaata cctgggccgc   1020
agcgattga                                                          1029

SEQ ID NO: 24           moltype = AA  length = 342
FEATURE                 Location/Qualifiers
source                  1..342
                        mol_type = protein
                        organism = Variovorax paradoxus
SEQUENCE: 24
MGSSHHHHHH SSGLVPRGSH MSFPFGAVVV TYFPTGEQVA NLHSLAASCP HLCVVDNTPQ     60
VGDWHAALVD AGVSVLHNGN RGGIAGAFNR GIIDLEARGA ELFFLLDQDS KLPPGYFDAM    120
CEAAMVARER KGEGNGEEDA AFLIGPLVHD TNLDALIPQF GLQGKRVYQF DLRQPFTEPL    180
MRCAFMISSG SLISRGAWAR IGRFDERYVI DHVDTDYCMR ALGRGVPLYL NPHVVLRHQI    240
GDIRARSLFG WKIHFINYPA ARRYYIARNA IDLSRAHVRA FPAILFINVY TLKQILPMLM    300
FERDRFKKTI ALMLGCFDGL FGRLGGLGEV HPRMGKYLGR SD                      342
```

GLYCOLIPOPEPTIDE BIOSURFACTANTS

CROSS REFERENCE TO RELATED APPLICATIONS

This application is a Continuation of U.S. application Ser. No. 16/817,193, filed Mar. 12, 2020, which is a Division of U.S. application Ser. No. 16/090,888, filed Oct. 3, 2018, now abandoned, which is the U.S. National Stage Application of International Applcation. No. PCT/EP2017/058296, filed Apr. 6, 2017, which claims priority of GB Application No. 1605875.2, filed Apr. 6, 2016, the entirety of each of which are incorporated herein by reference for all purposes.

REFERENCE TO SEQUENCE LISTING

The present application is being filed along with a Sequence Listing in electronic format. The Sequence Listing is provided as a file entitled GLYCOLIPOPEPTIDE BIOSURFACTANTS created on Mar. 9, 2023 and which is 60 KB bytes in size. The information in the electronic format of the Sequence Listing is identical to that in International Application PCT/EP2017/058296, filed Apr. 6, 2017 and U.S. application Ser. No. 16/817,193, filed Mar. 12, 2020 and incorporated herein by reference in its entirety.

FIELD OF THE INVENTION

This invention relates generally to the fields of surfactant chemistry, biochemistry, and microbiology. More specifically the invention relates to biosurfactants having a hydrophobic lipid oligomer covalently linked to a peptide or peptide-like (e.g. non-proteinogenic amino acid or single amino acid) chain and a carbohydrate moiety, various amino acid and nucleic acid sequences which encode components of biosynthetic pathways for these biosurfactants, and methods of making and using these biosurfactants.

BACKGROUND

Surfactants are amphiphilic chemicals that possess both hydrophobic and hydrophilic moieties which allow them to interact with polar and non-polar systems. Surfactants exert their activity at interfaces between different phases (gas, liquid, solid) and as a result exhibit a range of functions including, but not limited to the ability to act as detergents, emulsifiers, wetting agents and foaming agents. Most chemical surfactants are alkyl sulfates or sulfonates derived from petro- or oleo-chemical sources. The use of these products has been steadily growing with an estimated worldwide consumption of 13 million tonnes in 2008 and an estimated market value of $27 billion (USD) in 2012. In response to environmental and sustainability concerns, many companies utilizing chemical surfactants in their products have been exploring environmentally responsible alternatives as partial or full replacements for chemical surfactants. An alternative to chemical surfactants are biosurfactants, which are surface active molecules originating from microorganisms. These surfactants offer advantages over chemical surfactants such as production from sustainably produced feed stocks, biodegradability and lower toxicity.

SUMMARY

It was discovered that the bacterium *Variovorax paradoxus* RKNM-096, deposited on Apr. 10, 2015 as accession number NRRL B-67038 under the terms of the Budapest Treaty with the Agricultural Research Service Culture Collection (NRRL, 1818 North University Street, Peoria, Illinois, 61064) produces a previously unknown class of biosurfactants termed "glycolipopeptides". Unlike known biosurfactants, glycolipopeptides typically contain a hydrophobic lipid oligomer covalently linked to a peptide chain and a carbohydrate moiety. The deposit of NRRL B-67038 in support of this application was made by Nautilus Bioscience Canada Inc., 550 Unv. Ave., Charlottetown, PE, Canada, C1A4P3. Nautilus Bioscience Canada Inc. authorise the applicant to refer to the deposited biological material in this application and give their unreserved and irrevocable consent to the materials being made available to the public in accordance with appropriate national laws governing the deposit of these materials, such as Rule 31 and 33 EPC. The expert solution under Rule 32 EPC is also hereby requested.

Described herein are purified biosurfactants that include a hydrophobic lipid component including a carboxyl end and a hydroxyl end, wherein the lipid component is covalently linked to (i) a peptide or peptide-like chain at the carboxyl end of the lipid component and (ii) a carbohydrate moiety at the hydroxyl end of the lipid component via a glycosidic linkage. The peptide or peptide-like chain can include a serine-leucinol dipeptide, the lipid component can include three β-hydroxyalkanoic acid moieties (e.g., wherein the length of each acyl chain of the lipid component is $C_6$, $C_8$, $C_{10}$, or $C_{12}$), and the carbohydrate moiety can include a rhamnose moiety attached to the lipid component via a glycosidic linkage. In certain embodiments, the carbohydrate moiety can include two rhamnose moieties and/or an acetyl group. Analogues and derivatives of these glycolipopeptides can be made by conventional methods.

Glycolipopeptides can have the structure:

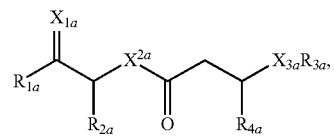

wherein $R_{1a}$ is H, OH, $OCH_3$, SH, $S(CH_3)$, $NH_2$, $NH(CH_3)$, $N(CH_3)_2$, or a peptide or peptide-like structure having the structure:

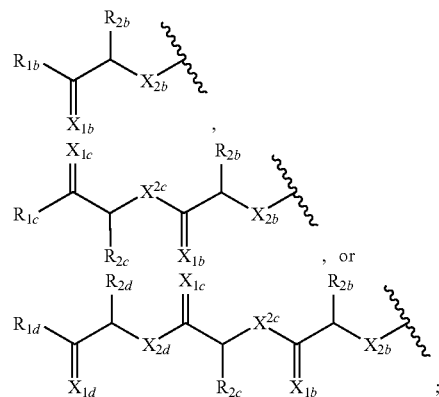

wherein $R_{1b}$, $R_{1c}$, and $R_{1d}$, are H, OH, $OCH_3$, SH, $S(CH_3)$, $NH_2$, $NH(CH_3)$, or $N(CH_3)_2$; $R_{2a}$, $R_{2b}$, $R_{2c}$, and $R_{2d}$ are each independently an amino acid side chain; $X_{1a}$, $X_{1b}$, $X_{1c}$, and $X_{1d}$ are each independently one oxygen atom or two hydrogen atoms; $X_{2a}$, $X_{2b}$, $X_{2c}$, and $X_{2d}$ are each independently NH, N(CH$_3$), or O; $R_{3a}$ is a carbohydrate portion or a lipid monomer having the structure:

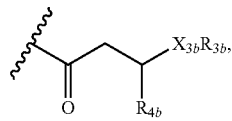

or a lipid oligomer having the structure of:

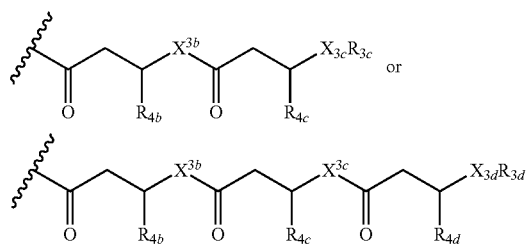

wherein $X_{3a}$, $X_{3b}$, $X_{3c}$, and $X_{3d}$ are each independently NH, N(CH$_3$), or O; $R_{3a}$, $R_{3b}$, $R_{3c}$, and $R_{3d}$ includes a carbohydrate portion including a monomer having the structure:

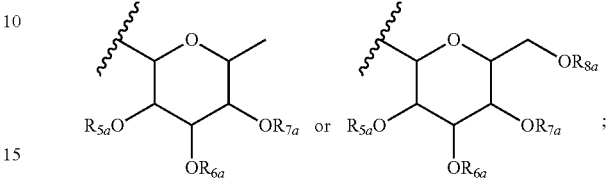

wherein $R_{5a}$, $R_{6a}$, $R_{7a}$, and $R_{8a}$ are each independently a hydrogen atom, methyl, acetyl, or a carbohydrate; and $R_{4a}$, $R_{4b}$, $R_{4c}$, and $R_{4d}$ are each independently a hydrogen atom, methyl, or a $C_2$ to $C_{19}$ saturated or unsaturated linear, branched-chain, cyclic, or aromatic hydrocarbon groups. Naturally occurring glycolipopeptides include those having the following structures:

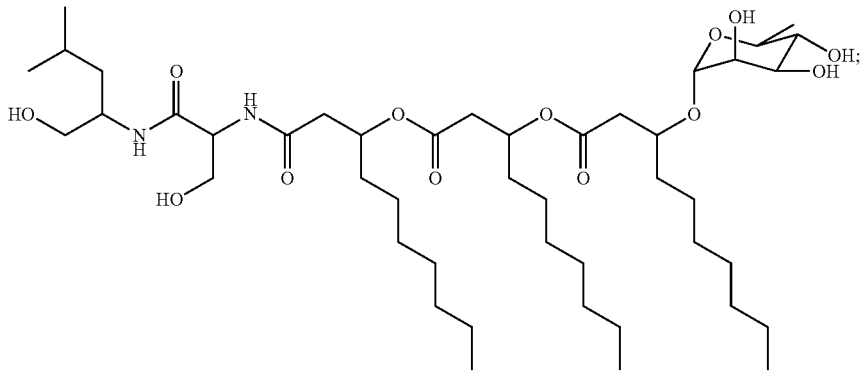

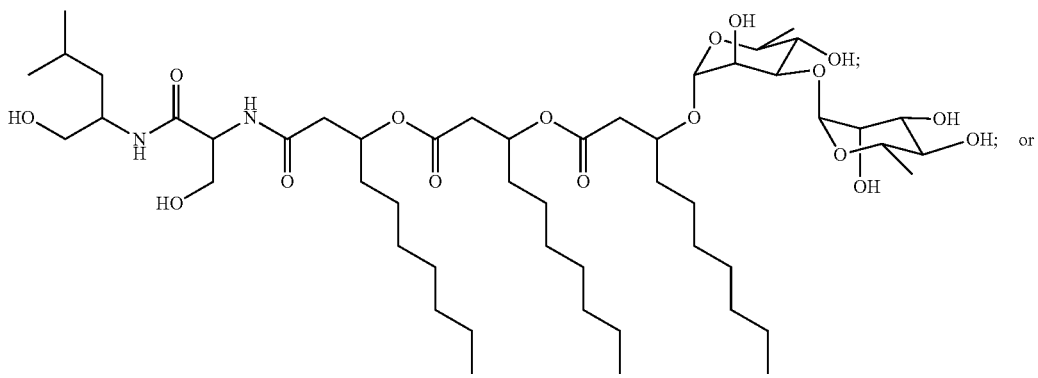

-continued

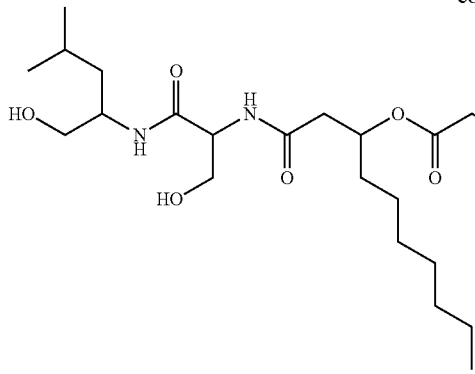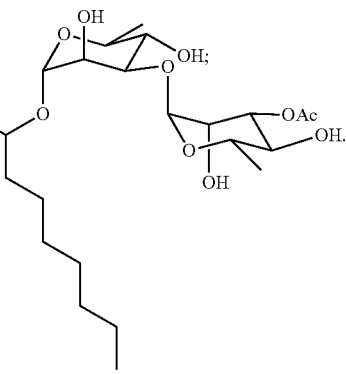

Also described herein are emulsified compositions (e.g., oil-in-water or water-in-oil emulsions) including: a polar component, a non-polar component, and one or more of the above described biosurfactants; and a method of making an water-in-oil or oil-in-water emulsion by mixing together a polar component, a non-polar component, and one or more of the above described biosurfactants. Further described herein are a method of making one of the above described biosurfactants by
  (a) isolating a microorganism which includes the biosurfactant,
  (b) placing the microorganism in a culture under conditions that promote the synthesis of the biosurfactant, and
  (c) isolating the biosurfactant from the culture; and an isolated microorganism engineered to produce one of the above described biosurfactants, wherein a set of heterologous genes involved in the biosynthesis of the biosurfactant has been introduced into the microorganism.

Unless otherwise defined, all technical terms used herein have the same meaning as commonly understood by one of ordinary skill in the art to which this invention belongs. Commonly understood definitions of chemical and biological terms can be found in Rieger et al., Glossary of Genetics: Classical and Molecular, 5th edition, Springer-Verlag: New York, 1991; and A Dictionary of Chemistry, Ed. J. Daintith, 7$^{th}$ Ed., Oxford University Press, 2016.

As used herein, when referring to a chemical or molecule, the term "purified" means separated from components that occur with it in nature or in an artificially produced mixture. Typically, a molecule is purified when it is at least about 10% (e.g., at least 9%, 10%, 20%, 30% 40%, 50%, 60%, 70%, 80%, 90%, 95%, 98%, 99%, 99.9%, and 100%), by weight (excluding solvent), free from components that occur with it in nature or in an artificially produced mixture. Purity can be measured by any appropriate method, e.g., column chromatography, polyacrylamide gel electrophoresis, or HPLC analysis.

By "sequence identity" is meant the relatedness between two amino acid sequences or between two nucleotide sequences. Herein, the degree of identity between two amino acid sequences or two deoxyribonucleotide sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix for amino acid sequences or the EDNAFULL (EMBOSS version of NCBI NUC4.4) substitution matrix for nucleotide sequence. The output of Needle labeled "longest identity" (obtained using the -nobrief option) is used as the percent identity and is calculated as follows:

(Identical Amino Acid of Nucleotide Residues×100)/
(Length of Alignment−Total Number of Gaps in Alignment).

Although methods and materials similar or equivalent to those described herein can be used in the practice or testing of the present invention, suitable methods and materials are described below. All patents, patent applications, and publications mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

FIG. 4 is the nucleic acid sequence SEQ ID NO:1.
FIG. 5 is the nucleic acid sequence SEQ ID NO:2.
FIG. 6 is the nucleic acid sequence SEQ ID NO:3.
FIG. 7 is the nucleic acid sequence SEQ ID NO:5.

FIG. 8 is the nucleic acid sequence SEQ ID NO:7.
FIG. 9 is the nucleic acid sequence SEQ ID NO:9.
FIG. 10 is the nucleic acid sequence SEQ ID NO:11.
FIG. 11 is the nucleic acid sequence SEQ ID NO:13.
FIG. 12 is the nucleic acid sequence SEQ ID NO:15.
FIG. 13 is the nucleic acid sequence SEQ ID NO:17.
FIG. 14 is the nucleic acid sequence SEQ ID NO:19.
FIG. 15 is the nucleic acid sequence SEQ ID NO:21.
FIG. 16 is the amino acid sequence SEQ ID NO:4.
FIG. 17 is the amino acid sequence SEQ ID NO:6.
FIG. 18 is the amino acid sequence SEQ ID NO:8.
FIG. 19 is the amino acid sequence SEQ ID NO:10.
FIG. 20 is the amino acid sequence SEQ ID NO:12.
FIG. 21 is the amino acid sequence SEQ ID NO:14.
FIG. 22 is the amino acid sequence SEQ ID NO:16.
FIG. 23 is the amino acid sequence SEQ ID NO:18.
FIG. 24 is the amino acid sequence SEQ ID NO:20.
FIG. 25 is the amino acid sequence SEQ ID NO:22.
FIG. 26 is the amino acid sequence SEQ ID NO:23.
FIG. 27 is the amino acid sequence SEQ ID NO:24.

DETAILED DESCRIPTION

Figure 1:
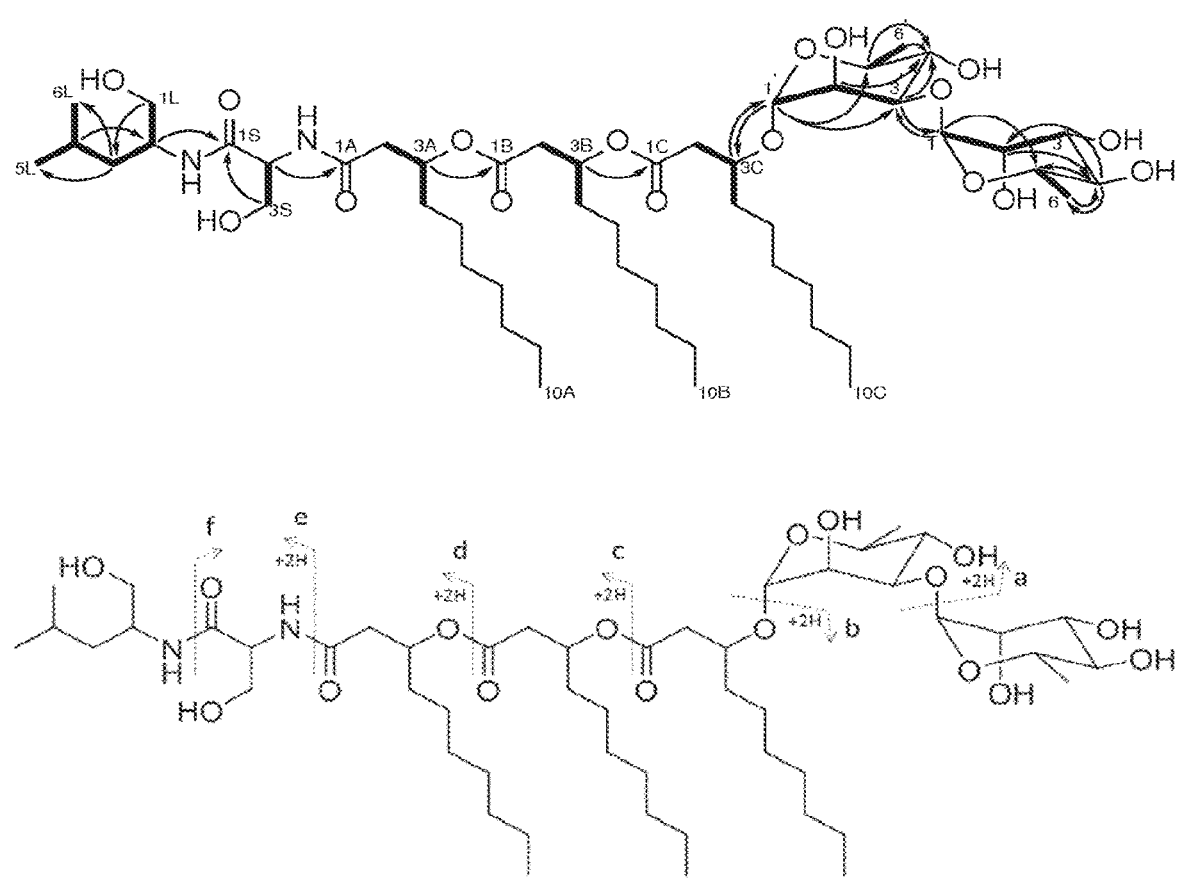
FIG. 1 is an illustration of selected HMBC ($^1$H→$^{13}$C) and COSY correlations (bold bonds) of NB-RLP1006 and assigned fragment ions from MS/MS collision-induced dissociation of the glycolipopeptides.

The invention encompasses glycolipopeptide surfactant compositions, methods of making and using such biosurfactants, and bacteria and bacterial culture that produce glycolipopeptides. The below described preferred embodiments illustrate adaptation of these compositions and methods. Nonetheless, from the description of these embodiments, other aspects of the invention can be made and/or practiced based on the description provided below.

General Methodology

Methods involving conventional organic chemistry, biochemistry, microbiology, and molecular biology are described herein. Such methods are described in, e.g., Clayden et al., Organic Chemistry, Oxford University Press, 1st edition (2000); Molecular Cloning: A Laboratory Manual, 2nd ed., vol. 1-3, Sambrook et al., ed., Cold Spring Harbor Laboratory Press, Cold Spring Harbor, N.Y., 2001; Current Protocols in Molecular Biology, Ausubel et al., ed., Greene Publishing and Wiley-Interscience, New York; and in the various volumes of Methods in Microbiology and Methods in Biochemistry and Molecular Biology both published by Elsevier.

Glycolipopeptides

Naturally occurring glycolipopeptides and synthetic analogues and derivatives thereof typically include a hydrophobic lipid component including a carboxyl end and a hydroxyl end, wherein the lipid component is covalently linked to (i) a peptide or peptide-like chain at the carboxyl end of the lipid component and (ii) a carbohydrate moiety at the hydroxyl end of the lipid component via a glycosidic linkage.

The peptide chain may comprise in the range of between 2 and 10 amino acids, preferably 2 to 8, more preferably 2 to 4 amino acids. The peptide chain may most preferably comprise 2 amino acids. The peptide or peptide-like chain can comprise and/or consist of a serine-leucinol dipeptide.

The lipid component may comprise in the range of between 1 and 6 alkanoic acid moieties, preferably 2 to 4, and more preferably 3. Most preferably the lipid component can include three β-hydroxyalkanoic acid moieties. The length of each acyl chain of the lipid component may be in the range of between $C_4$ to $C_{20}$, preferably $C_6$ to $C_{16}$, more preferably $C_8$ to $C_{14}$. Most preferably the length of each acyl chain may be selected from $C_8$, $C_{10}$, or $C_{12}$.

The carbohydrate moiety may be selected from saccharides including glucose, fructose, galactose, mannose, ribose, or deoxy saccharide variants including deoxyribose, fucose, or rhamnose. Preferably the carbohydrayte moiety is rhamnose. In particular, a rhamnose moiety attached to the lipid component via a glycosidic linkage. In certain embodiments, the carbohydrate moiety can include one, two, or three rhamnose moieties and/or an acetyl groups. Preferably the carbohydrate moiety includes two.

Glycolipopeptides can include the structure:

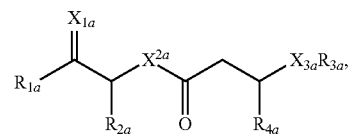

wherein $R_{1a}$ is H, OH, $OCH_3$, SH, $S(CH_3)$, $NH_2$, $NH(CH_3)$, $N(CH_3)_2$, or a peptide or peptide-like structure having the structure:

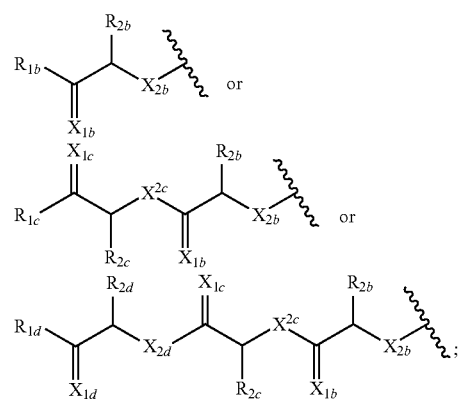

wherein $R_{1b}$, $R_{1c}$, and $R_{1d}$, are H, OH, $OCH_3$, SH, $S(CH_3)$, $NH_2$, $NH(CH_3)$, or $N(CH_3)_2$; $R_{2a}$, $R_{2b}$, $R_{2c}$, and $R_{2d}$ are each independently an amino acid side chain; $X_{1a}$, $X_{1b}$, $X_{1c}$, and $X_{1d}$ are each independently one oxygen atom or two hydrogen atoms; $X_{2a}$, $X_{2b}$, $X_{2c}$, and $X_{2d}$ are each independently NH, $N(CH_3)$, or O; $R_{3a}$ is a carbohydrate portion or a lipid monomer having the structure:

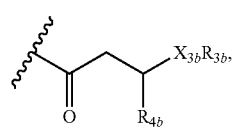

or a lipid oligomer having the structure of:

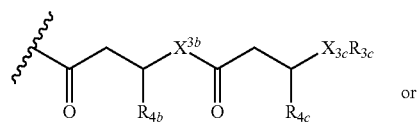

or

-continued

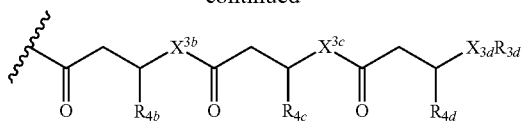

wherein $X_{3a}$, $X_{3b}$, $X_{3c}$, and $X_{3d}$ are each independently NH, N(CH$_3$), or O; $R_{3a}$, $R_{3b}$, $R_{3c}$, and $R_{3d}$ includes a carbohydrate portion including a monomer having the structure:

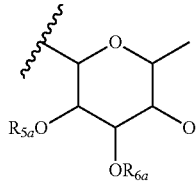 or 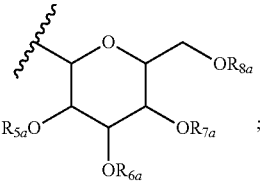 ;

wherein $R_{5a}$, $R_{6a}$, $R_{7a}$, and $R_{8a}$ are each independently a hydrogen atom, methyl, acetyl, or a carbohydrate; and $R_{4a}$, $R_{4b}$, $R_{4c}$, and $R_{4d}$ are each independently a hydrogen atom, methyl, or a $C_2$ to $C_{19}$ saturated or unsaturated linear, branched-chain, cyclic, or aromatic hydrocarbon groups. In the foregoing, at least one of $R_{6a}$, $R_{7a}$, and $R_{8a}$ can include a carbohydrate monomer having the structure:

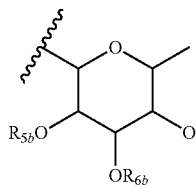 or 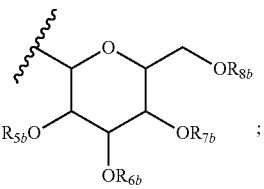 ;

wherein $R_{5b}$, $R_{6b}$, $R_{7b}$, and $R_{8b}$ are each independently a hydrogen atom, methyl, acetyl, or a carbohydrate.

In certain embodiments the peptide or peptide-like portion includes at least one proline or proline-like monomer having the structure:

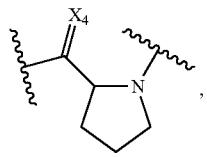

wherein $X_4$ is one oxygen atom or two hydrogen atoms, or a single proline or proline-like monomer or a terminal proline or proline-like monomer having the structure:

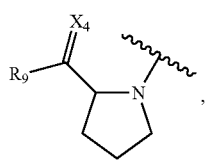

wherein $R_9$ is of H, OH, OCH$_3$, SH, S(CH$_3$), NH$_2$, NH(CH$_3$), or N(CH$_3$)$_2$; and $X_4$ is one oxygen atom or two hydrogen atoms.

Glycolipopeptides can have the following structures:

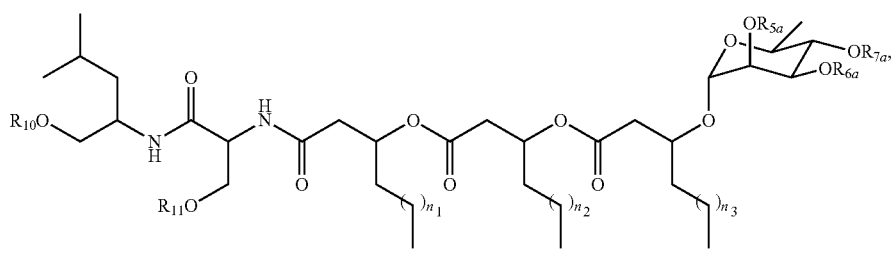

wherein $R_{5a}$, $R_{6a}$, $R_{7a}$, $R_{10}$, and $R_{11}$ are each independently a hydrogen atom or acetyl; and $n_1$, $n_2$, and $n_3$ are integers each independently ranging from 1 to 7;

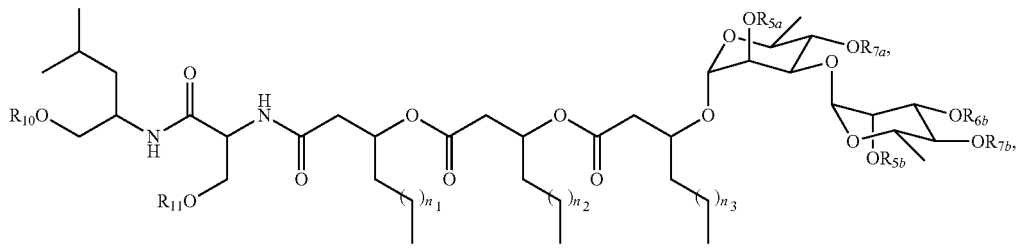

wherein $R_{5a}$, $R_{5b}$, $R_{6b}$, $R_{7a}$, $R_{7b}$, $R_{10}$, and $R_{11}$ are each independently a hydrogen atom or acetyl; and $n_1$, $n_2$, and $n_3$ are integers each independently ranging from 1 to 7;

chain, cyclic, or aromatic hydrocarbon groups. The rhamnose moieties could be linked together via 1,2-, 1,3-, or 1,4-glycosidic linkages, which may possess either the α- or

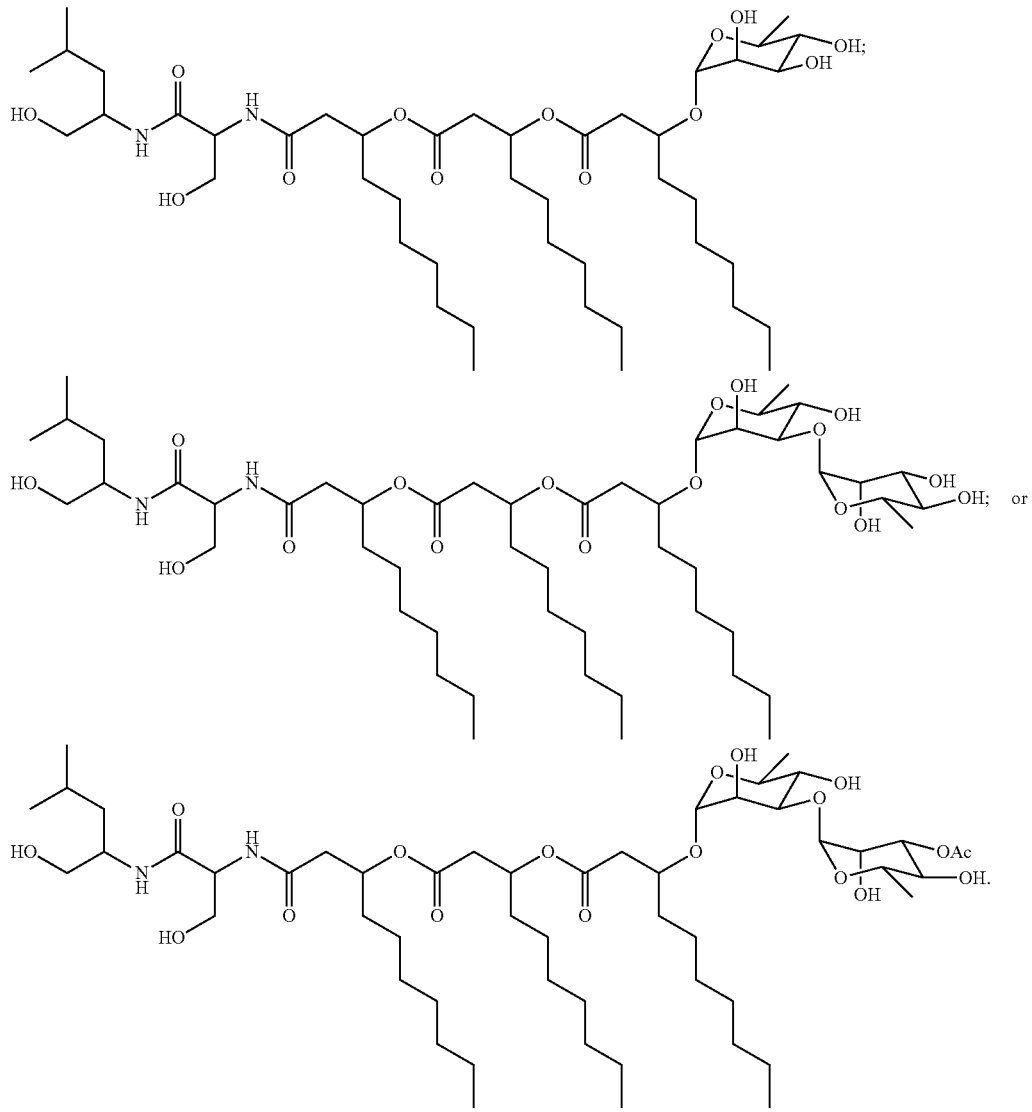

Derivatives, analogues, and other variants of the foregoing glycolipopeptides can be made by one of skill in the art. For instance, the amino acid composition and length of the peptide chain could be modified in a combinatorial fashion, introducing either proteinogenic or unnatural amino acids to modulate the solubility, hydrophilic-lipophilic balance (HLB), and other surfactant characteristics of the glycolipopeptides. The peptide portion may also contain amino acids with charged functional groups, which may result in cationic, anionic, or zwitterionic surfactants with unique surfactant applications. The carboxylic acid functionality at the C-terminus position of the peptide may also be reduced to a primary hydroxyl group. Similarly, the lipid portion may contain various numbers (e.g., 1, 2, 3, 4 or more) of β-hydroxyalkanoate units, which themselves may be comprised of $C_2$ to $C_{19}$ saturated or unsaturated linear, branched- β-configuration. In addition to rhamnose, the carbohydrate portion may also be composed of glucose or other monosaccharide units.

Variants of the *Variovorax paradoxus* RKNM-096 glycolipopeptide biosurfactants that have altered properties could be made. Altered properties of such variants may include, but are not limited to, alterations in emulsification, foaming and surface tension reducing properties exhibited under differing physiochemical conditions such as, but not limited to, temperature, pH, and salinity.

The variovaricins describe herein may be at least 5, 10, 20, 30, 40, 50, 60, 70, 80, 90, 95, 99, 99.5, 99.9, or 99.99 percent purified (by weight). They may be in crystalline or non-crystalline (amorphous) form, and in some cases also be obtained as salts derived from such organic and inorganic acids as: acetic, trifluoroacetic, lactic, citric, tartaric, formate, succinic maleic, malonic, gluconic, hydrochloric, hydrobromic, phosphoric, nitric, sulfuric, methane sulfonic and similarly known acids. The salts can be prepared by adapting commonly known procedures.

In some embodiments, the composition includes additional compounds such as carriers, other surfactants (e.g., non-glycolipopeptide surfactants), or biologically active compounds (non-glycolipopeptide surfactants, such as pharmaceutical agents or other non-glycolipopeptide antimicrobial agents). The addition of the aforementioned agents to glycolipopeptide surfactants can be selected by one skilled in the art based on the chosen application.

The composition can include a carrier, such as conventional pharmaceutically acceptable carriers as described in *Remington: The Science and Practice of Pharmacy*, The University of the Sciences in Philadelphia, Editors, Lippincott, Williams, & Wilkins, Philadelphia, Pa., $21^{st}$ Edition (2005). Pharmaceutically acceptable carriers vary depending on the mode of administration. Fluid formulations used for parenteral injection may include fluids such as water, physiological saline, aqueous dextrose or glycerol. Solid formulations may include highly purified solid carriers such as magnesium stearate, starch, or lactose. Pharmaceutical compositions may also contain minor quantities of non-toxic auxiliary substances, such as buffers and preservatives.

In some embodiments, the compositions include a non-glycolipopeptide surfactant. Examples include non-ionic, cationic, anionic and amphoteric surfactants. Representative examples of anionic surfactants include carboxylates, sulfonates, petroleum sulfonates, alkylbenzene sulfonates, naphthalene sulfonates, olefin sulfonates, alkyl sulfates, sulfates, sulfated natural oils and fats, sulfated esters, sulfated alkanolamides, alkylphenols, ethoxylated and sulfated aklylphenols and rhamnolipids. Examples of cationic surfactants include quaternary ammonium salts, N, N, N', N' tetrakis substituted ethylenediamines and 2-alkyl-1-hydroxethyl-2-imidazolines. Examples of non-ionic surfactants include ethyoxylated aliphatic alcohols, polyoxyethylene surfactants, carboxylic esters, polyethylene glycol esters, anhydrosorbitol ester and ethoxylated derivatives, glycol esters of fatty acids, carboxylic amides, monoalkanolamine condensates and polyoxyethylene fatty acid amides. Examples of amphoteric surfactants include sodium salts of N-coco-3-aminopropionic acid, N-tallow-3-iminodipropionate and N-cocoamidethyl-N-hydroxyethylglycine, as well as N-carboxymethyl-N-dimethyl-N-(9-octadecenyl) ammonium hydroxide. In further embodiments, the composition includes one or more food or food additive, cosmetic or pharmaceutical agents or antimicrobial agents (such as an antibacterial or antifungal agents).

Methods of Making Glycolipopeptides

The glycolipopeptides described herein may be made by isolation or purification from bacteria strains which produce them, such as *Variovorax paradoxus* RKNM-096. As described in the Examples section below, bacteria which produce one or more glycolipopeptides can be isolated from natural habitats or obtained from publicly accessible sources. Bacteria can be determined to produce glycolipopeptides by the methods described in the Examples. The glycolipopeptide-producing bacterium can be placed in a bioreactor (vessel) containing suitable culture medium, and then incubated under conditions that promote bacterial replication and production of one or more glycolipopeptides. The produced glycolipopeptide(s) can be purified or isolated from the culture mixture by conventional techniques such as extraction followed by chromatographic separation (e.g., using ultra high performance liquid chromatography). Chemical analyses (determination of molecular weight, melting point, NMR, IS spectroscopy, etc.) can be performed to confirm the structure and purity of the isolated glycolipopeptide(s). Alternatively, the glycolipopeptides described herein may be made by total synthesis or semi-synthesis, e.g. as described herein.

Glycolipopeptides Gene Clusters and Methods of Use

As described in Example 7 below, the glycolipopeptide and rhamnose biosynthetic gene clusters of *V. paradoxus* RKNM-096 were characterized. The polypeptides encoded in the gene cluster function in a coordinated fashion to synthesize the NB-RLP series of biosurfactants. The nucleotide sequence encoding these genes and the amino acid sequences of the corresponding polypeptides are shown in the sequence listing. Other amino acid sequences and the nucleic acid sequences that share at least 70% (e.g., at least 70, 80, 90, 95, 97, 98, or 99%) sequence identity with those shown in the sequence listing might also be used in the methods and compositions described herein particularly when such other sequences exhibit (or encode a molecule exhibiting) at least 50% (e.g., at least 50, 60, 70, 80, 90, or 100%) of the corresponding native polypeptide enzymatic activity. Nucleic acid sequences which encode the same polypeptides described herein but are not included in the sequence listing might also be used.

The foregoing polynucleotides might be used in a method for producing recombinant biosynthetic enzymes. As one example, such a method might include culturing a host cell (e.g., *E. coli* or another suitable prokaryotic or eukaryotic host cell) which contains an expression vector having a nucleic acid sequence of one or more of SEQ ID NO:1, SEQ ID NO:2, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19 and SEQ ID NO:21 in a culture medium under conditions suitable for expression of the recombinant protein in the host cell, and b) isolating the recombinant protein(s) from the host cell or the culture medium.

Also contemplated is method of producing a glycolipopeptide in a heterologous host cell by expressing the complete or partial biosynthetic gene cluster. This method might include the steps of a) culturing a host cell which contains an expression vector having nucleic acid sequences comprising SEQ ID NO:1, SEQ ID NO:2, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19 and SEQ ID NO:21 in a culture medium under conditions suitable for expression of the recombinant proteins in the host cell, and b) isolating produced glycolipopeptides from the culture medium.

Further contemplated are methods for using a nucleic acid molecule that hybridizes to or includes a portion of SEQ ID NO:1, SEQ ID NO:2, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19 or SEQ ID NO:21 as a probe or PCR primer to identify other organisms capable of producing glycolipopeptides or structurally similar biosurfactants.

Synthesis

The compounds of the present invention may be achieved using chemical methods as noted herein.

The total synthesis of the glycolipopeptides can be achieved using established synthetic methodology to assemble commercially available building blocks. A retrosynthetic analysis of NB-RLP1006 (1) demonstrates the feasibility of the total synthesis. As an example, one skilled in the art of organic synthesis may couple the dipeptide substituent (4) to the tridecanoic acid (5) and perform a chemical glycosylation of the lipopeptide intermediate (2) using glycosyl donor 3 as shown below. The dipeptide moiety can be prepared using standard amide coupling methods, while the tridecanoic acid can be generated from commercially available ethyl trans-2-decenoate. Meanwhile, the α-1,3-linked dirhamnose substituent (3) can be assembled using glycosyl donor 6 and glycosyl acceptor 7.

To generate the carbohydrate substituent, α-1,3 linked dirhamnose, a number of protecting group manipulations must be performed to enable regioselective glycosylation of the rhamnose sugar at the 3-OH position (Scheme 2). The p-methoxyphenyl α-L-rhamnopyranoside (8), which serves as a synthetic precursor to both rhamnose moieties, can be synthesized from commercially available L-rhamnose in three steps. The terminal rhamnose sugar can then be prepared by perbenzylation of 8 and removal of the p-methoxyphenyl substituent to allow synthesis of the rhamnosyl trichloroacetimidate (9). Meanwhile, a six-step sequence of protecting group manipulations can provide p-methoxyphenyl 2,4-di-O-benzyloxyrhamnopyranoside (10) (Cai, X.; et al. Carbohydr. Res. 2010, 345, 1230), which can be glycosylated at the 3-OH position to achieve the α-1,3 glycosidic linkage between the two rhamnose substituents. The anomeric effect is expected to direct the formation of an α-glycosidic linkage with high stereoselectivity in this chemical glycosylation (Takahashi, O.; et al. Carbohydr. Res. 2007, 342, 1202).

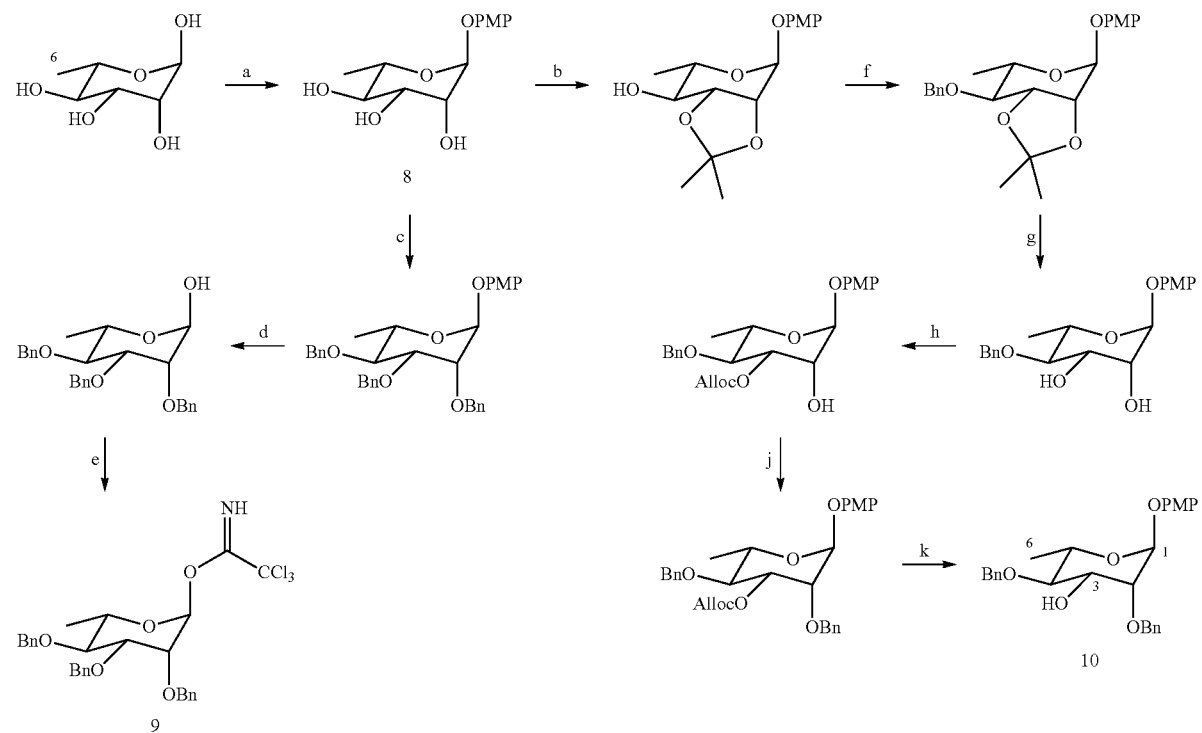

Scheme 2. Synthesis of rhamnosyl donor 9 and glycosyl accepter 10 as building blocks for the assembly of the dirhamnose substituent.

Reagents and conditions: (a) (i) Ac$_2$O, pyridine, 70° C., 16 h. (ii) p-methoxyphenol, BF$_3$•Et$_2$O, CH$_2$Cl$_2$, 0° C. → 25° C., 3 h. (iii) NaOCH$_3$, CH$_3$OH. 125(b) CH$_3$C(OCH$_3$)$_2$CH$_3$, DMF, TsOH•H$_2$O. (c) BnBr, Bu$_4$NI, DMF, 0° C. → 25° C., 3 h. (d) 80% CH$_3$CN, CAN, 35° C., 30 min. (e) CCl$_3$CN, DBU, CH$_2$Cl$_2$, 25° C., 30 min. (f) BnBr, Bu$_4$NI, NaH, DMF, 0° C. → 25° C., 3 h. (g) 70% AcOH, 70° C., 3 h. (h) AllocCl, pyridine, DMF, CH$_2$Cl$_2$, -15° C. → 0° C., 3 h. (j) BnBr, Bu$_4$NI, NaH, DMF, 0° C → 25° C., 3 h.; (k) NaBH$_4$, Pd[P(C$_6$H$_5$)$_3$]$_4$, CH$_3$COONH$_4$, CH$_3$OH: THF (1:1), -5° C., < 30 min.

It is understood that this general approach, or other similar approaches in which one assembles commercially available starting materials, could enable the synthesis of glycolipopeptide analogues. For instance, different amino acids can be incorporated into the peptide or peptide-like portion while the length of the peptide chain can be increased or decreased. Similarly, structural modifications could be made to the lipid and carbohydrate portions of the glycolipopeptides to produce analogues with potentially useful biosurfactant characteristics.

To assemble the dirhamnose substituent, glycosyl donor 9 can be linked to glycosyl acceptor 10 through activation of the anomeric trichloroacetimidate using either BF$_3$·Et$_2$O or TMSOTf (Scheme 3). The anomeric p-methoxyphenyl protecting group must then be replaced with a good leaving group, such as a trichloroacetimidate, to enable glycosylation of the decanoic acid moiety. Alternatively, a thiophenyl group could be installed instead of the p-methoxyphenyl group during reaction A of Scheme 2. This approach would allow an orthogonal glycosylation to be pursued given the dual role of the anomeric thiophenyl group as a protecting and leaving group (Gampe, C. M.; et al. Tetrahedron 2011, 67, 9771; Wu, C.-Y.; Wong, C.-H. Top. Curr. Chem. 2011, 301, 223). It is known that the total synthesis of NB-RLP860 could be achieved using rhamnosyl donor 9 or other suitable rhamnosyl donors. Furthermore, it is recognized that a skilled chemist could modify the carbohydrate moiety of the glycolipopeptides by using glycosyl donors other than 9, 11, or 12.

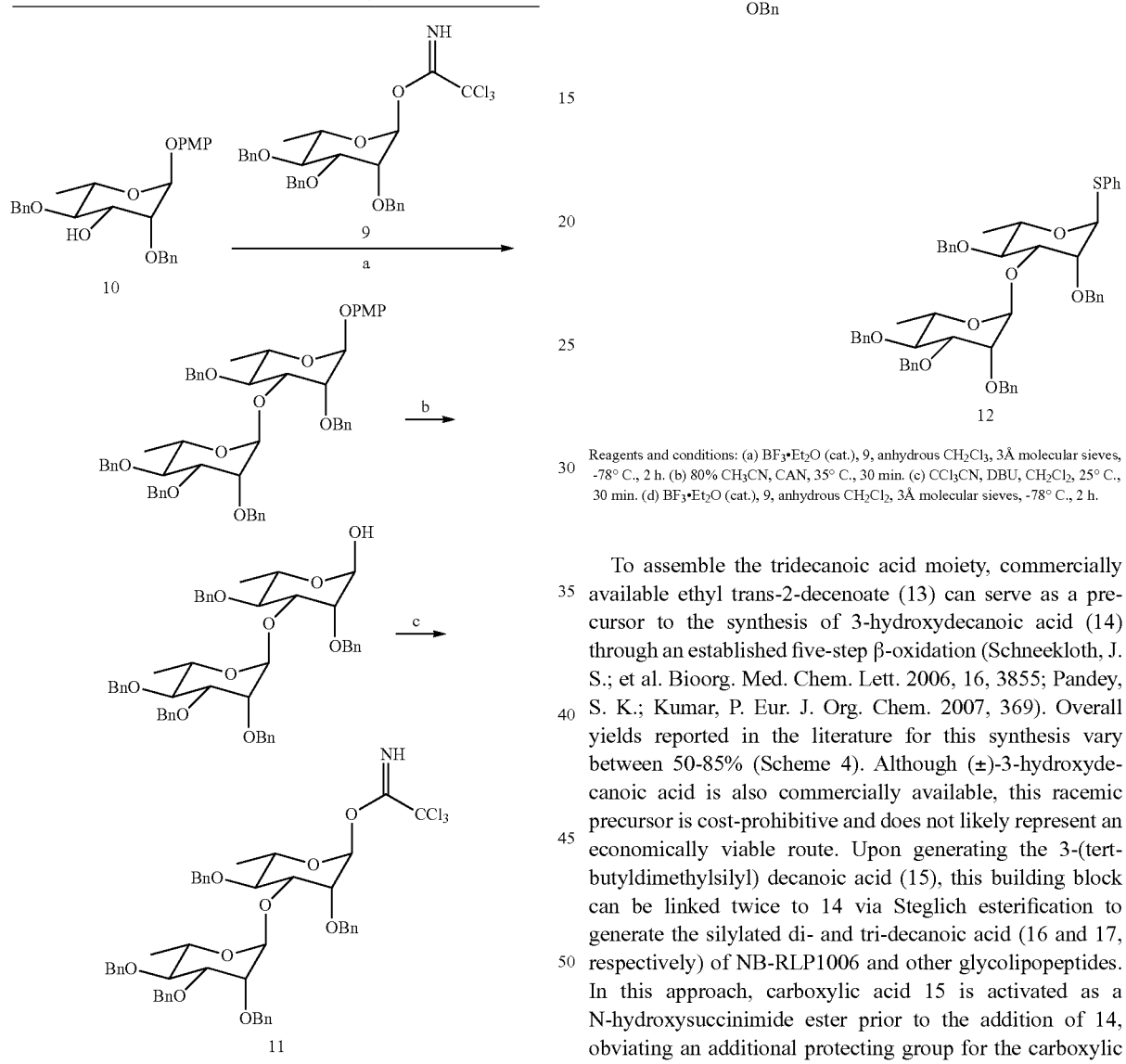

Reagents and conditions: (a) BF$_3$•Et$_2$O (cat.), 9, anhydrous CH$_2$Cl$_3$, 3Å molecular sieves, -78° C., 2 h. (b) 80% CH$_3$CN, CAN, 35° C., 30 min. (c) CCl$_3$CN, DBU, CH$_2$Cl$_2$, 25° C., 30 min. (d) BF$_3$•Et$_2$O (cat.), 9, anhydrous CH$_2$Cl$_2$, 3Å molecular sieves, -78° C., 2 h.

To assemble the tridecanoic acid moiety, commercially available ethyl trans-2-decenoate (13) can serve as a precursor to the synthesis of 3-hydroxydecanoic acid (14) through an established five-step β-oxidation (Schneekloth, J. S.; et al. Bioorg. Med. Chem. Lett. 2006, 16, 3855; Pandey, S. K.; Kumar, P. Eur. J. Org. Chem. 2007, 369). Overall yields reported in the literature for this synthesis vary between 50-85% (Scheme 4). Although (±)-3-hydroxydecanoic acid is also commercially available, this racemic precursor is cost-prohibitive and does not likely represent an economically viable route. Upon generating the 3-(tert-butyldimethylsilyl) decanoic acid (15), this building block can be linked twice to 14 via Steglich esterification to generate the silylated di- and tri-decanoic acid (16 and 17, respectively) of NB-RLP1006 and other glycolipopeptides. In this approach, carboxylic acid 15 is activated as a N-hydroxysuccinimide ester prior to the addition of 14, obviating an additional protecting group for the carboxylic acid functionality of 14.

Scheme 4. Synthesis of tridecanoic acid moiety (17) of NB-RLP1006.

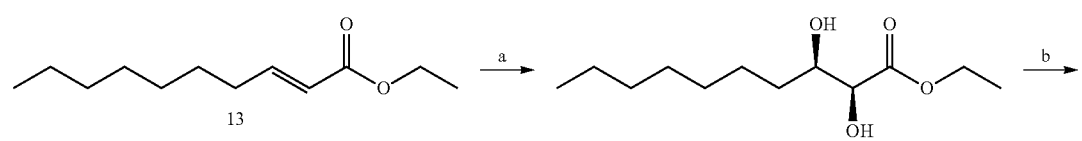

-continued

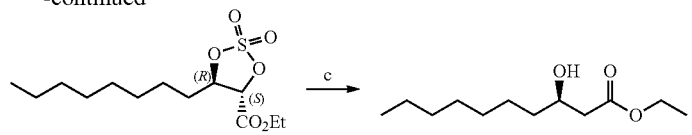

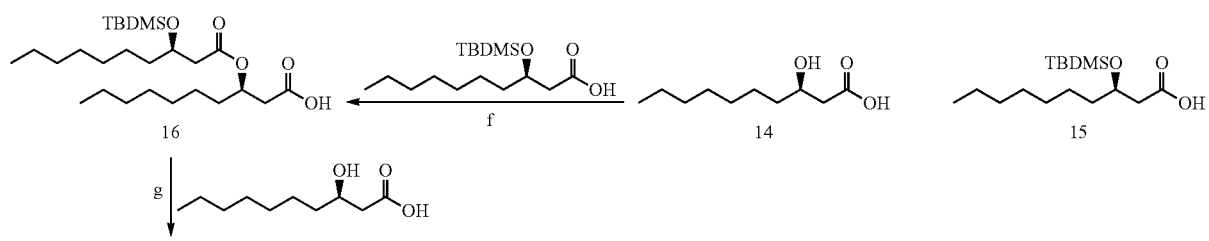

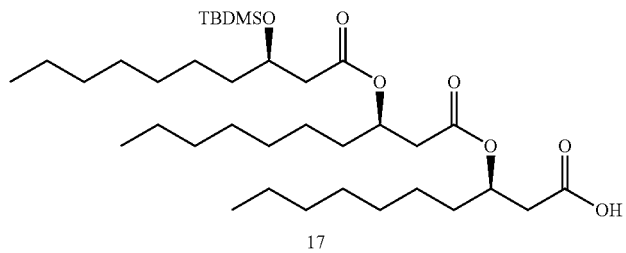

Reagents and conditions: (a) (DHQD)$_2$PHAL (1 mol %), 0.1M OsO$_4$ (0.5 mol %), K$_2$CO$_3$, K$_3$Fe(CN)$_6$, CH$_3$SO$_2$NH$_2$, t-BuOH:H$_2$O (1:1), 0° C., 24 h. (b) (i) SOCl$_2$, Et$_3$N, CH$_2$Cl$_2$, 0° C., 30 min. (ii) RuCl$_3$, NaIO$_4$, CCl$_4$:CH$_3$CN:H$_2$O (2:2:3), 0° C., 1 h. (c) NaBH$_4$, DMAC, 25° C., 30 min. (d) NaOH, Acetone:H$_2$O (1:1), 25° C., 16-24 h. (e) (i) TBDMSCl, imidazole, DMF, 25° C. (ii) NaOH, Acetone:H$_2$O (1:1), 25° C., 16-24 h. (f) (i) 3-benzyloxydecanoic acid, DIC, NHS, 0° C. → 25° C., 3 h. (ii) 3-hydroxydecanoic acid, Et$_3$N, DMAP, 25° C., 3 h. (g) (i) 3-(3-(benzyloxy)decanoyloxy) decanoic acid, DIC, NHS, 0° C. → 25° C., 3 h. (ii) 3-hydroxydecanoic acid, Et$_3$N, DMAP, 25° C., 3 h.

An alternative approach is also available in which the carboxylic acid group of 14 is protected as a benzyl ester before esterification (Scheme 5). In this approach, building blocks 15 and 18 are linked together in a synthesis that requires additional steps for installing and removing silyl ether and benzyl ester protecting groups. It is known that a chemist skilled in the art of organic synthesis could utilize either approach to introduce C$_2$ to C$_{19}$ saturated or unsaturated linear, branched-chain, cyclic, or aromatic hydrocarbon moieties in order to modify the lipid portion of the glycolipopeptides. It is anticipated that analogues generated through this approach may also exhibit surfactant properties.

Scheme 5. Alternative route to the tridecanoic acid moiety (17) of NB-RLP1006.

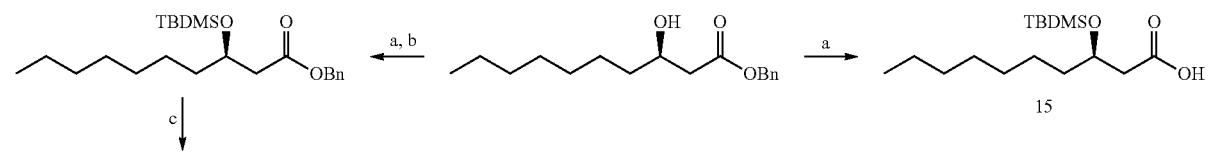

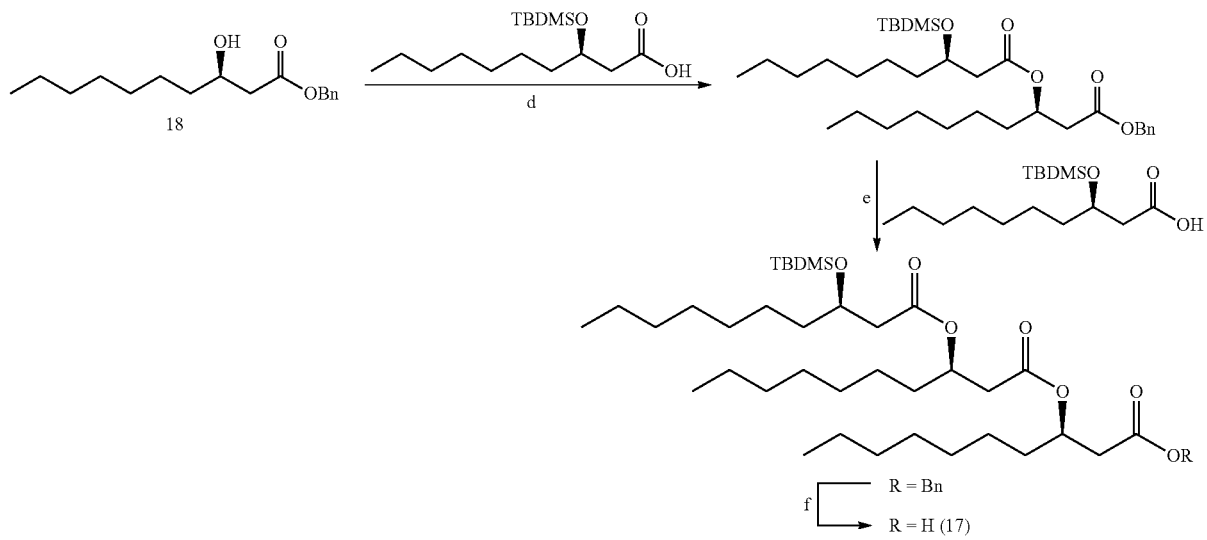

Reagents and conditions: (a) (i) TBDMSCl, imidazole, DMF, 25° C. (ii) NaOH, Acetone:H₂O (1:1), 25° C., 16-24 h. (b) (i) DIC, NHS, 0° C. → 25° C., 3 h. (ii) BnOH, Et₃N, DMAP, 25° C., 3 h. (c) Bu₄NF, THF, 25° C., 3 h. (d) (i) 3-(tert-butyldimethylsilyloxy)decanoic acid (15), DIC, NHS, 0° C. → 25° C., 3 h. (ii) benzyl 3-hydroxydecanoate (18), Et₃N, DMAP, 25° C., 3 h. (e) (i) Bu₄NF, THF, 25° C., 3 h. (ii) 3-(tert-butyldimethylsiloxy)decanoic acid (15), DIC, NHS, 0° C. → 25° C., 3 h. (iii) benzyl 3-(3-hydroxydecanoyloxy)decanoate, Et₃N, DMAP, 25° C., 3 h. (f) 10% Pd/C (20 wt %), H₂, CH₂Cl₂, 25° C., 16 h.

The leucinol-serine dipeptide can be assembled from commercially available Boc-leucinol (19) and Fmoc-Ser(Bzl)-OH (20) using well-established amide coupling chemistry (Scheme 6) (Valeur, E.; Bradley, M. Chem. Soc. Rev. 2009, 38, 606). The five-step reaction sequence involves protecting the primary hydroxyl group of 19 as a benzyl ether and coupling the two amino acids before removing the 9-fluorenylmethyloxycarbonyl (Fmoc) protecting group to generate the leucinol-serine dipeptide (21) that is poised for amide coupling to the decanoic acid. It is conceivable that other commercially available amino acids, including but not limited to D-amino acids and β-amino acids, could be assembled in a similar fashion to introduce structural modifications at the peptide portion of the glycolipopeptide. The C-terminus of the peptide or peptide-like portion could exist as a carboxylic acid functionality or be reduced to a primary hydroxyl group. Other modifications of the C-terminus position include, but are not limited to, alkylation, acylation, glycosylation, phosphorylation, and sulfation. The chain length of the peptide or peptide-like portion could be increased by coupling additional amino acid monomers to the dipeptide intermediate. Alternatively, a single amino acid monomer could be coupled to the tridecanoic acid intermediate (17) to decrease the chain length.

Scheme 6. Preparation of the leucinal-serine dipeptide residue of NB-RLP1006.

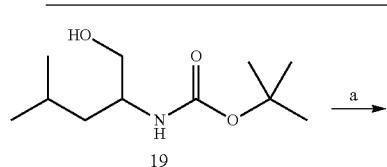

Reagents and conditions: (a) (i) BnBr, Bu₄NI, NaH, DMF, 0° C. → 25° C., 3 h. (ii) HCl, CH₃OH, 25° C., 1 h. (b) (i) Fmoc-Serine(Bzl)—OH, DIC, NHS, 0° C. → 25° C., 3 h. (ii) Leucinol(Bzl), Et₃N, DMAP, 25° C., 3 h. (c) Piperidine (20 vol %), DMF, 25° C., 3 h The tridecanoic acid (17) can readily undergo amide coupling to the benzylated dipeptide (21), upon which the tert-butyldimethyl silyl ether protecting group can be removed using tetrabutylammonium fluoride to provide glycosyl acceptor 22 (Scheme 7). Glycosylation of 22 with either 11 or 12, followed by global deprotection via hydrogenolysis of the benzyl ethers, furnishes the deprotected glycolipopeptide NB-RLP1006.

Scheme 7. Final steps in the assembly of the glycolipopeptide NB-RLP1006.

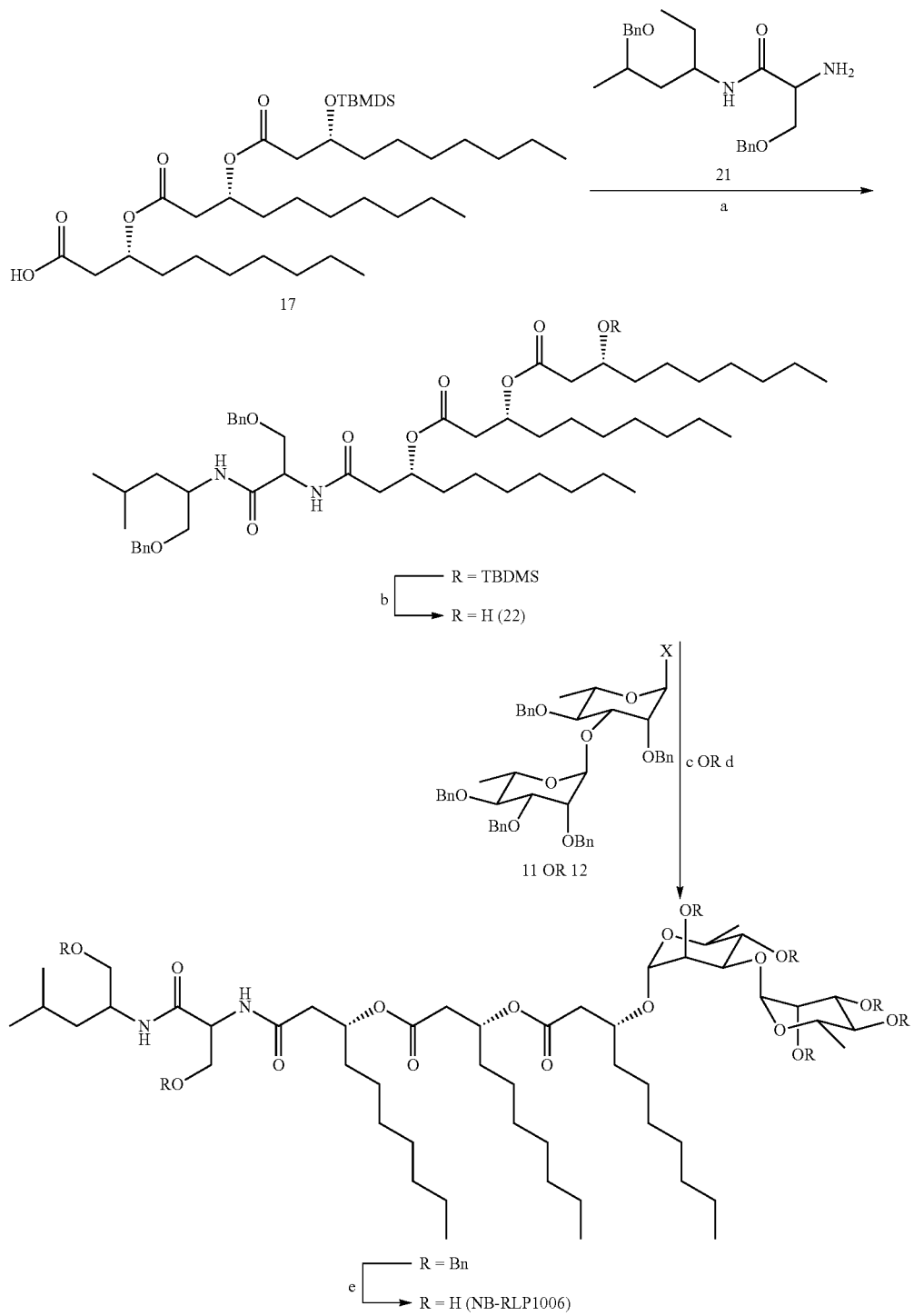

Reagents and conditons: (a) (i) DIC, NHS, 0° C. → 25° C., 3 h. (ii) Leucinol(Bzl)-Ser(Bzl)NH$_2$ (21), Et$_3$N, DMAP, 25° C., 3 h. (b) Bu$_4$NF, THF, 25° C., 3 h. (c) If glycosyl donor 11 (X = CNHCl$_3$), BF$_3$·Et$_2$O (cat.), 3Å molecular sieves anhydrous CH$_2$Cl$_2$, -78° C., 2 h. (d) If glycosyl donor 12 (X = SPh), NIS, TfOH (10 mol %), 1,2-DCE, 4Å molecular sieves. (e) 10% Pd/C (20 wt %), H$_2$, CH$_2$Cl$_2$, 25° C., 16 h.

Although the total synthesis of NB-RLP1006 may require between 14-18 steps (longest linear sequence, 34-40 steps total), the synthesis could be expedited by utilizing solid-phase synthetic techniques in which the terminal leucinol residue is immobilized onto a solid support. For example, the Leucinol(Bzl) (19) can be tethered to a polystyrene-bound p-alkoxybenzyl hydroxyl group (Wang resin) through a silyl ether linkage (Scheme 8) (Scott, P. J. H. Linker Strategies in Solid-Phase Synthesis, John Wiley & Sons Ltd: Chichester, U.K., 2009; pp 50-51). Following previously described amide coupling and Steglich esterification methodologies (Coin, I.; et al. Nat. Protoc. 2007, 2, 3247.), the remaining serine and decanoic acid residues can then be attached in a step-wise approach using Fmoc-Ser(Bzl)-OH (20) and 3-(tert-butyldimethylsilyl)decanoic acid (23). After releasing the lipopeptide intermediate, the primary hydroxyl group can be selectively protected as a tert-butyldiphenylsilyl ether to provide glycosyl acceptor 24. The glycolipopeptide NB-RLP1006 can then be synthesized by chemical glycosylation and removal of the silyl and benzyl ether protecting groups. Analogues of the glycolipopeptides can also be produced using solid-phase synthetic techniques as described in the foregoing solution-phase synthesis of NB-RLP1006.

thesis of the tridecanoic acid (23) by acid hydrolysis of the glycolipopeptide mixture (Scheme 9). See Miao, S.; et al. J. Agric. Food Chem. 2015, 63, 3367. Tridecanoic acid (23) could then be coupled to the peptide portion and glycosylated with commercially available disaccharides, such as lactose or maltose, to generate novel glycolipopeptide analogues (e.g. 24). The aglycone of glycolipopeptides may also be produced by *V. paradoxus* RKNM-096 and undergo chemical glycosylation to produce similar analogues. It is also known that the rhamnolipids could be utilized as an advanced precursor and linked to various dipeptides (e.g. 21) through the carboxylic acid functional group to produce glycolipopeptides similar to NB-RLP1006 (Scheme 10).

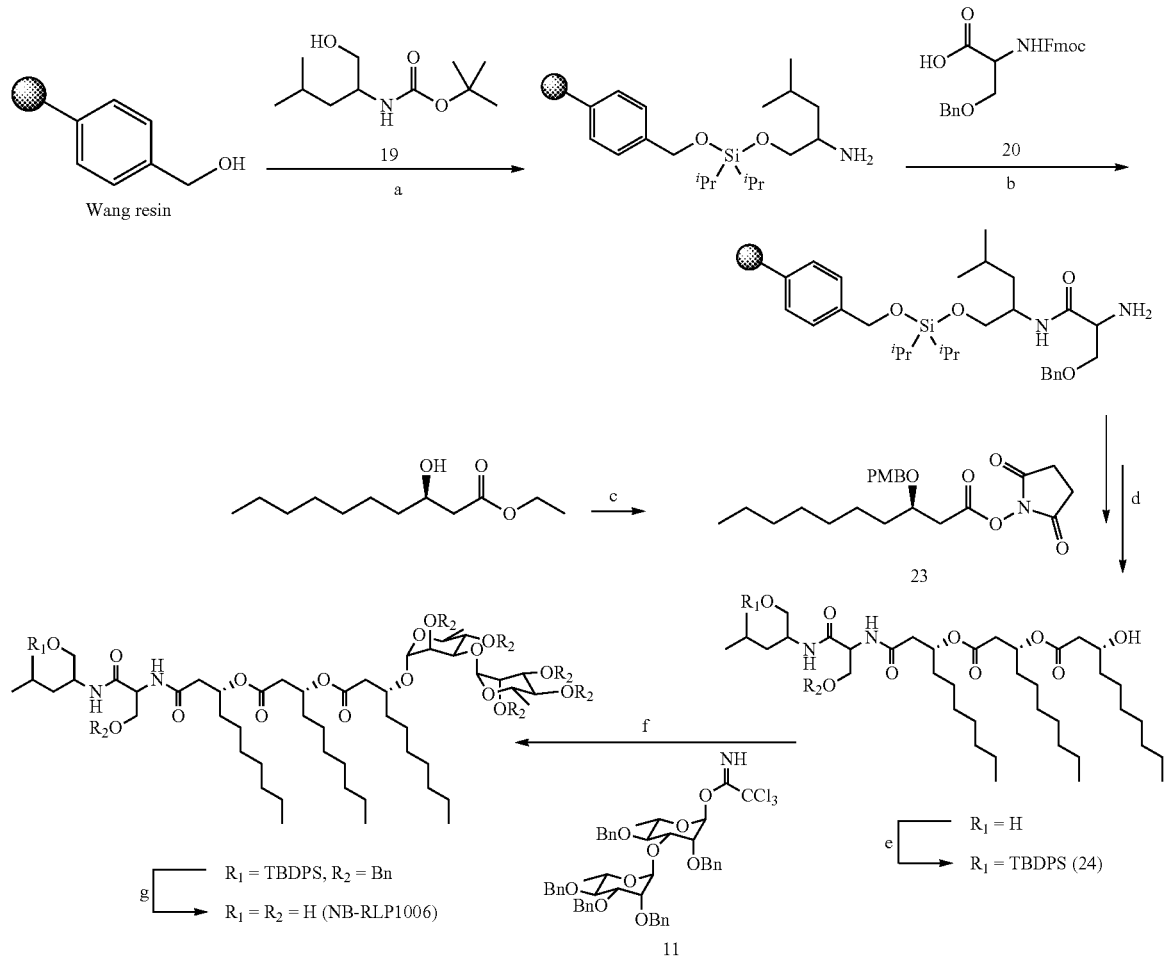

Scheme 8. Solid-phase total synthesis of NB-RLP1006.

Reagents and conditions: (a) (i) Leucinol(Bzl) (19), $^{i}Pr_2SiCl_2$, imidazole, DMF, 25° C., 1 h. (ii) HCl, CH$_3$OH, 25° C., 1 h. (b) (i) Fmoc-Serine(Bzl)-OH (20), DIC, NHS, 0° C. → 25° C., 2 h. (ii) Et$_3$N, DMAP, 25° C., 3 h. (c) (i) PMBCl, NaH, DMF, 0° C. → 25° C., 3 h. (ii) NaOH, Acetone:H$_2$O (3:1), 25° C., 16-24 h. (iii) DIC, NHS, 0° C. → 25° C., 3 h. (d) (i) 23, Et$_3$N, DMAP, 25° C., 3 h. (ii) 80% CH$_3$CN, CAN, 35° C., 30 min. (iii) 23, Et$_3$N, DMAP, 25° C., 3 h. (iv) 80% CH$_3$CN, CAN, 35° C., 30 min. (v) 23, Et$_3$N, DMAP, 25° C., 3 h. (vi) 80% CH$_3$CN, CAN, 35° C., 30 min. (vii) Bu$_4$NF, THF, 25° C., 3 h. (e) TBDPSCl, imidazole, DMAP, DMF, 25° C., 2 h. (f) BF$_3$·Et2O (cat.), anhydrous CH$_2$Cl$_2$, -78° C., 2 h. (g) (i) Bu4NF, THF, 25° C., 3 h. (ii) 10% Pd/C (20 wt %), H$_2$ CH$_2$Cl$_2$, 25° C., 16 h.

Semisynthesis of the Glycolipopeptides

Synthetic analogues of NB-RLP1006 and other glycolipopeptides may also be of interest for assessing the structure-activity relationships of this class of biosurfactants. Unlike the total synthesis, a semisynthesis could represent a rapid approach for developing a number of glycolipopeptide analogues. For instance, strategies may involve a semisyn- Given the commercial availability of the rhamnolipids, conceivably one skilled in the art of organic synthesis would also recognize that peptide chains other than leucinol-serine could be introduced to expand on the structural diversity of glycolipopeptide analogues accessible through this semisynthetic approach.

Scheme 9. Alternative semisynthetic route to glycolipopeptide analogues from tridecanoic acid (23) and commercially available disaccharides.

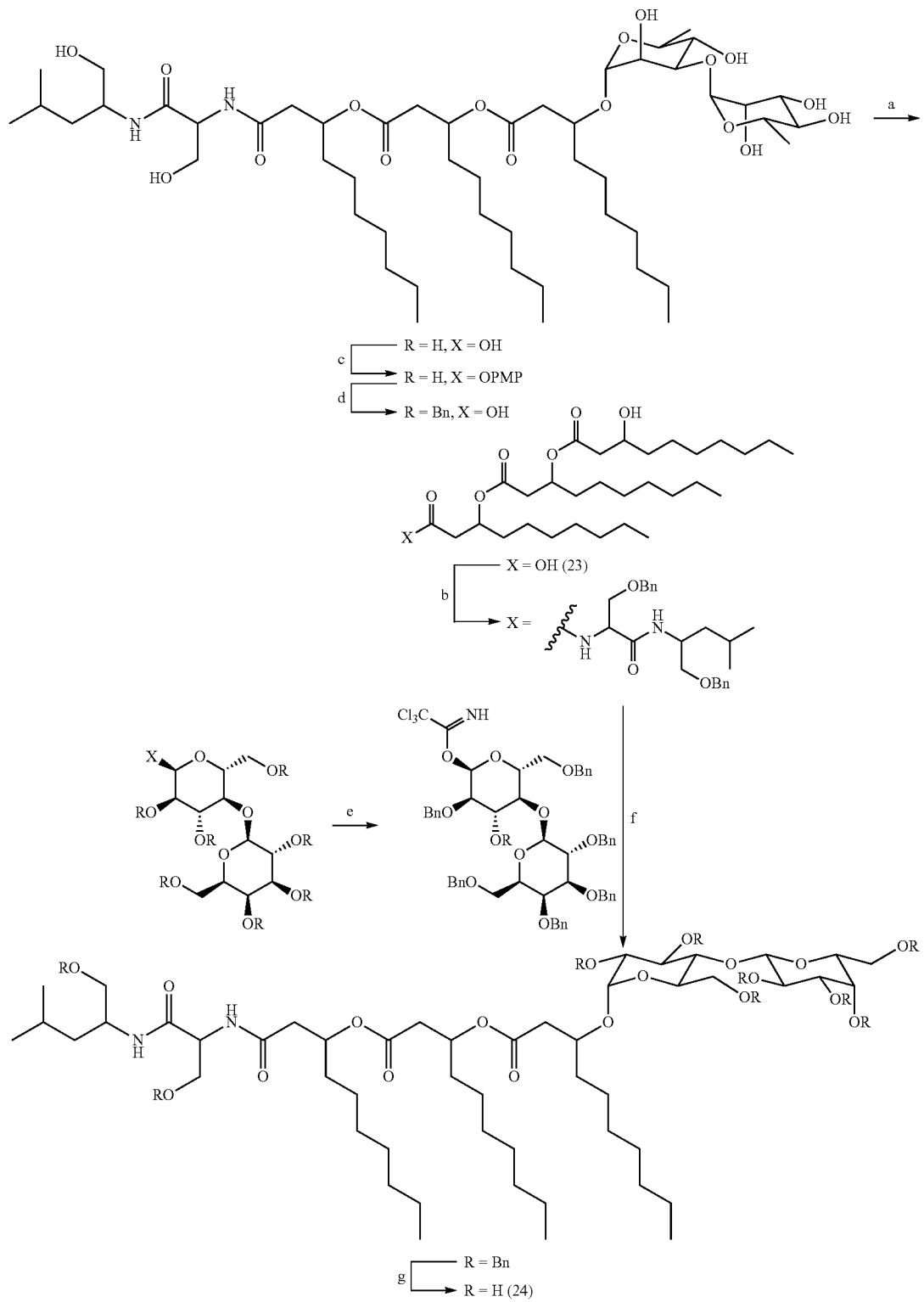

Reagents and conditions: (a) 1M HCl, CH$_3$CN:H$_2$O (1:), 95° C., 16 h. (b) (i) DIC, NHS, 0° C. → 25° C., 3 h. (ii) Leucinol(Bzl)-Ser(Bzl)NH$_2$ (21), Et$_3$N, DMAP, 25° C., 3 h. (c) (i) Ac$_2$O, pyridine, 70° C., 16 h. (ii) p-methoxyphenol, BF$_3$·Et$_2$O, CH$_2$Cl$_2$, 0° C. → 25° C., 3 h. (iii) NaOCH$_3$, CH$_3$OH. (d) (i) BnBr, Bu$_4$NI, NaH, DMF, 0° C. → 25° C., 3 h. (ii) 80% CH$_3$CN, CAN, 35° C., 30 min. (e) CCl$_3$CN, DBU, CH$_2$Cl$_2$, 25° C., 30 min. (f) BF$_3$·Et$_2$O (cat.), anhydrous CH$_2$Cl$_2$, -78° C., 2 h. (g) 10% Pd/C (20 wt %), H$_2$, CH$_2$Cl$_2$, 25° C., 16 h.

Scheme 10. Semisynthesis of a glycolipopeptide analogue (25) from commercially available rhamnolipids.

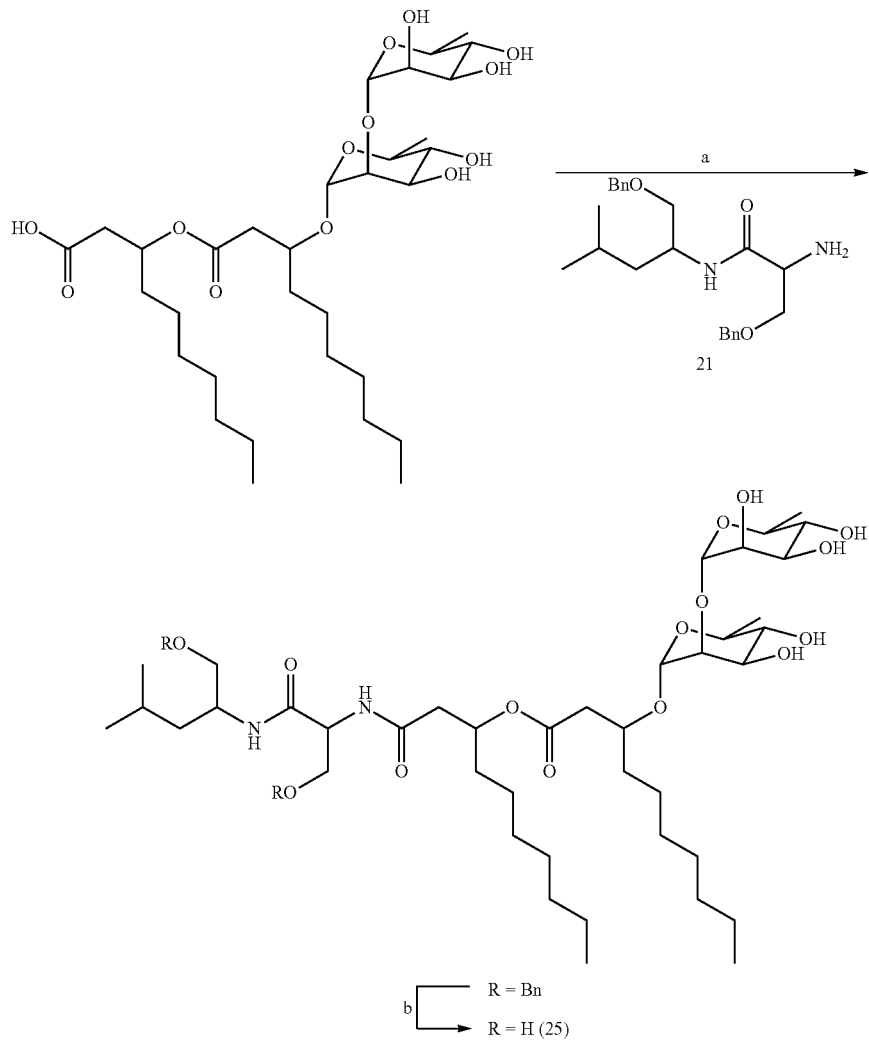

Reagents and conditions: (a) (i) PyBOP, DMF, 0° C. → 25° C., 2 h. (ii) Leucinol(Bzl)-Ser(Bzl)NH$_2$ (21), Et$_3$N, 0° C. → 25° C., 2 h. (b) 10% Pd/C (20 wt %). H$_2$, CH$_2$Cl$_2$, 25° C., 16 h.

Conceivably one skilled in the art of organic synthesis could isolate naturally occurring glycolipopeptides from a microbial fermentation and synthesize derivatives, analogues, and other structural variants. For instance, modifications that could occur at $R_{5a}$, $R_{5b}$, $R_{6a}$, $R_{6b}$, $R_{7a}$, $R_{7b}$, $R_{10}$, and $R_{11}$ include, but are not limited to, alkylation, acylation, glycosylation, phosphorylation, and sulfation. The glycolipopeptides could also undergo a base hydrolysis to produce rhamnolipid-like compounds with potentially useful surfactant properties. It is also known that a base hydrolysis reaction would provide NB-RLP374.

Methods of Use

The glycolipopeptides described herein might be used similarly to other surfactants. They may, for example, be used as detergents, emulsifiers, dispersants, wetting agents, foaming agents, or biofilm inhibitors/disruptors. A typical use would be for the preparation of emulsions for cosmetic or pharmaceutical formulations (eg., water-in-oil or oil-in-water emulsions), where one or more glycolipopeptides or derivatives or analogues thereof is mixed with a polar component and a non-polar component.

The properties of the surfactants of this invention also make them suitable as emulsifiers particularly in oil in water or water-iin-oil emulsions e.g. in personal care applications. Personal care emulsion products can take the form of creams and milks desirably and typically include emulsifier to aid formation and stability of the emulsion. Typically, personal care emulsion products use emulsifiers (including emulsion stabilisers) in amounts of about 3 to about 5% by weight of the emulsion.

The oil phase of such emulsions are typically emollient oils of the type used in personal care or cosmetic products, which are oily materials which is liquid at ambient temperature or solid at ambient temperature, in bulk usually being a waxy solid, provided it is liquid at an elevated temperature, typically up to 100° C. more usually about 80° C., so such solid emollients desirably have melting temperatures less than 100° C., and usually less than 70° C., at which it can be included in and emulsified in the composition.

The concentration of the oil phase may vary widely and the amount of oil is typically from 1 to 90%, usually 3 to 60%, more usually 5 to 40%, particularly 8 to 20%, and especially 10 to 15% by weight of the total emulsion. The amount of water (or polyol, e.g. glycerin) present in the emulsion is typically greater than 5%, usually from 30 to 90%, more usually 50 to 90%, particularly 70 to 85%, and especially 75 to 80% by weight of the total composition. The amount of surfactant used in such emulsions may be in the range from 0.001 to 10% by weight of the emulsio, preferably 0.01 to 6% by weight, more preferably 0.1 to 5% by weight, further preferably 1 to 3% by weight. The amount of surfactant used on such emulsions is typically from 2 to 5.5%, by weight of the emulsion.

The end uses formulations of such emulsions include moisturizers, sunscreens, after sun products, body butters, gel creams, high perfume containing products, perfume creams, baby care products, hair conditioners, skin toning and skin whitening products, water-free products, antiperspirant and deodorant products, tanning products, cleansers, 2-in-1 foaming emulsions, multiple emulsions, preservative free products, emulsifier free products, mild formulations, scrub formulations e.g. containing solid beads, silicone in water formulations, pigment containing products, sprayable emulsions, colour cosmetics, conditioners, shower products, foaming emulsions, make-up remover, eye make-up remover, and wipes, A preferred formulation type is a sunscreen containing one or more organic sunscreens and/or inorganic sunscreens such as metal oxides, but desirably includes at least one particulate titanium dioxide and/or zinc oxide.

All of the features described herein may be combined with any of the above aspects, in any combination. It is to be understood that the invention is not to be limited to the details of the above embodiments, which are described by way of example only. Many variations are possible.

In order that the present invention may be more readily understood, reference will now be made, by way of example, to the following description.

EXAMPLES

Example 1: Isolation of *Variovorax paradoxus* RKNM-096.

Bacterial strain RKNM-096 was isolated from soil collected from the Battle Bluffs area west of Kamloops, British Columbia. RKNM-096 was isolated as a mucoid, yellow pigmented colony, and purified by serial subculturing. The bacterium was identified by 16S rRNA gene analysis, which indicated that RKNM-096 was a strain of *V. paradoxus*.

Example 2: Identifying *Variovorax paradoxus* RKNM-096 as a Biosurfactant Producer

*V. paradoxus* RKNM-096 was identified as a biosurfactant producer in a screen aimed at identifying bacterial producers of biosurfactants with emulsifying properties. The assay utilized to identify bacterial producers of biosurfactants was the emulsification activity assay. In this assay cultures were grown in 10 mL of liquid medium in 25 mm×150 mm glass tubes at 30° C. with shaking at 200 rpm for 5 days. After 5 days, the cells were removed by centrifugation and 3.5 mL of cell free culture broth was mixed with 3.5 mL of kerosene in a 13 mm×100 mm test tube with a screw cap tube. The tubes were vortexed for two minutes and then allowed to stand overnight at room temperature after which the height of the emulsion ($h_{emuls}$) and the total height ($h_{total}$) of the liquid in the tube were measured. The emulsification index ($E_{24}$) was calculated using the equation $E_{24}=h_{emuls}/h_{total}\times 100\%$. Fermentation broths of *V. paradoxus* RKNM-096 cultured in ISP2 broth (0.4% maltose, 0.4% yeast extract, 1.0% dextrose, pH 7.0) exhibited an $E_{24}$ value of 50.7%.

Example 3: Identification of Glycolipopeptide Biosurfactants Produced by *Variovorax paradoxus* RKNM-096

To determine if a small molecule was responsible for the observed emulsification activity, *V. paradoxus* RKNM-096 was fermented in ISP2 broth as described above and the broth was extracted twice with 10 mL of ethyl acetate (EtOAc). The EtOAc extract was then washed twice with 10 mL of water to remove any remaining polar media components from the EtOAc extract. For comparison purposes an ISP2 media blank was extracted in an identical manner. The EtOAc extracts were evaporated in vacuo and reconstituted in $CH_3OH$ at a concentration of 0.5 mg/mL.

The extracts were separated by ultra high performance liquid chromatography (UPLC; Accela™, Thermo Fisher Scientific Mississauga, ON, Canada) and the eluates analyzed with a photodiode array detector (200-600 nm) (PDA; Accela™, Thermo Fisher Scientific Mississauga, ON, Canada), an evaporative light scattering detector (ELSD; Sedex, Sedere, Alfortville, France) and a high resolution mass spectrometer utilizing electrospray ionization (HRES-IMS) (Orbitrap Exactive; Thermo Fisher Scientific, Mississauga, ON, Canada) (positive mode, monitoring m/z 200-2000). Chromatographic separation was achieved with a Kinetex 1.7 μm $C_{18}$ 100 æ 50×2.1 mm column (Phenomenex, Torrance, CA, USA) and a linear gradient from 95% $H_2O$/0.1% formic acid (FA) (solvent A) and 5% acetonitrile ($CH_3CN$)/0.1% FA (solvent B) to 100% solvent B over 5 min followed by a hold of 100% solvent B for 3 min with a flow rate of 400 μL/min. Examination of the ELSD chromatogram of the *V. paradoxus* RKNM-096 extract revealed five prominent peaks. The first peak eluted at 0.50 min and was present in the media blank indicating this peak was composed of media components. The following four peaks (1-4) eluted at 3.0 min, 5.04 min, 5.29 min and 5.39 min in the ELSD chromatogram, respectively. These peaks were not observed in the media blank extracts, indicating that these peaks were metabolic products of *V. paradoxus* RKNM-096. Peak 1 eluted at 3.00 min and examination of the mass spectrum of the corresponding peak in the total ion chromatogram (3.04 min) revealed the presence of two ions with mass to charge ratios (m/z) of 375.2855 and 397.2673, which is consistent with the anticipated $[M+H]^+$ and $[M+Na]^+$ for a compound with a molecular formula of $C_{19}H_{38}N_2O_5$ and mass of 374.2781. The mass spectra of peaks 2-4 were examined in an identical manner and the $[M+H]^+$ ions were identified as m/z 1007.6628, 1049.6778, and 1049.6734, respectively. The difference in mass between the $[M+H]^+$ ions associated with peaks 3 and 4 was 4.2 ppm, suggesting that these two compounds likely had an identical molecular formula, however the slight difference in retention time indicated that they were probably closely related structural analogues.

The compounds were also elucidated using NMR. The NMR data indicated the presence of four carbonyl groups in addition to two sugar residues with characteristic anomeric carbon chemical shifts at $\delta_C$ 101.4 and $\delta_C$ 103.9. Key COSY and HMBC correlations allowed the chemical characterization of the amino acid-derived leucinol, a serine residue, and three 3-hydroxydecanoic acids (FIG. 1). The connectivity between the different moieties was further confirmed by tandem mass spectrometry. The two deoxyhexose residues were identified by interpretation of $^1$H-$^1$H COSY correlations and coupling constant analysis. The small J-coupling exhibited by the anomeric proton H-1' OH 4.79, d, J=1.4 Hz) and the methine proton H-2' ($\delta_H$ 3.86, dd, J=3.2, 1.4 Hz) placed protons H-1' and H-2' in the equatorial position, while the larger J-coupling for H-4' ($\delta_H$ 3.53-3.48, app. t) indicated the axial relationship with H-3' and H-5', and therefore suggested an α-rhamnopyranosyl residue. The HMBC cross peak between the anomeric proton H-1' and C-3C ($\delta_C$ 76.5) demonstrated the attachment of this sugar to the 3-hydroxydecanoic acid moiety. The second sugar residue was also identified as an α-rhamnopyranose on the basis of coupling constant values. The small J-coupling for H-1" ($\delta_H$ 5.01, d, J=1.5 Hz) and H-2" ($\delta_H$ 3.98, dd, J=3.3, 1.5 Hz) indicated the equatorial orientation of these protons, while the larger coupling constant for H-4" ($\delta_H$ 3.40, app. t, J=9.5 Hz) demonstrated its axial relationship with H-3" and H-5". A key HMBC correlation between H-3' and C-1" established a 1,3-α-glycosidic linkage between the two rhamnopyranose moieties.

The structure of NB-RLP1006 is:

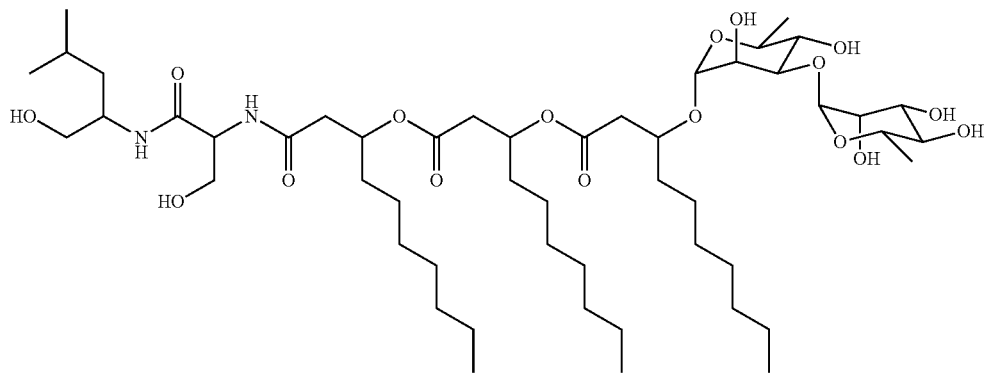 [SMILES: CCCCCCCC(CC(=O)NC(CO)C(=O)NC(CO)CC(C)C)OC(=O)CC(CCCCCCC)OC(=O)CC(CCCCCCC)OC1OC(C)C(O)C(OC2OC(C)C(O)C(O)C2O)C1O]

Organic extracts from *V. paradoxus* RKNM-096 were also fractionated by automated normal-phase chromatography followed by reversed-phase HPLC, which provided NB-RLP1048A and NB-RLP1048B. On the basis of HRES-IMS analysis (NB-RLP1048A: HRESIMS m/z 1049.6778 [M+H]$^+$; NB-RLP1048B: HRESIMS 1049.6734 [M+H]$^+$, calcd for $C_{53}H_{97}N_2O_{18}$, 1049.6731), these compounds were determined to be mono-acetylated analogues of NB-RLP1006. The apparent molecular formula of these compounds is $C_{53}H_{96}N_2O_{18}$. Based on NMR analysis, NB-RLP1048A consisted of an inseparable mixture of acetylated glycolipopeptides with the structure:

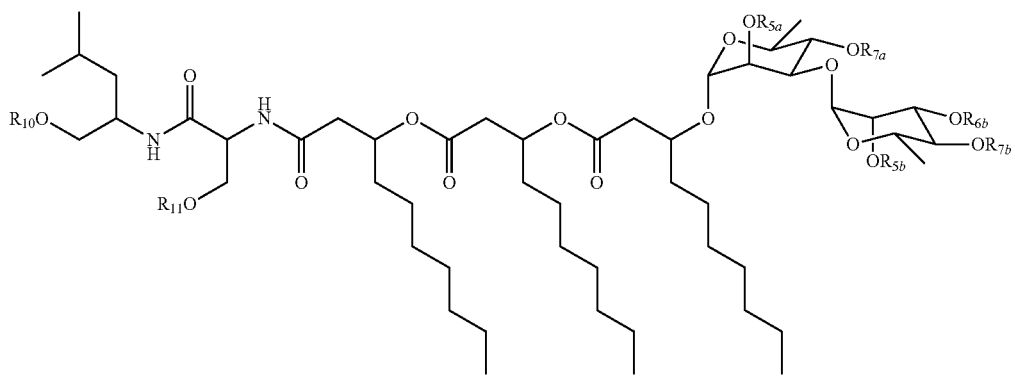

where any single R-group is an acetyl group, while all other R-groups are hydrogen atoms.

The chemical structure of NB-RLP1048B was determined by 1D and 2D NMR spectroscopic techniques, confirming the location of the acetyl group at the C-3" position.

The chemical structure of NB-RLP1048B is:

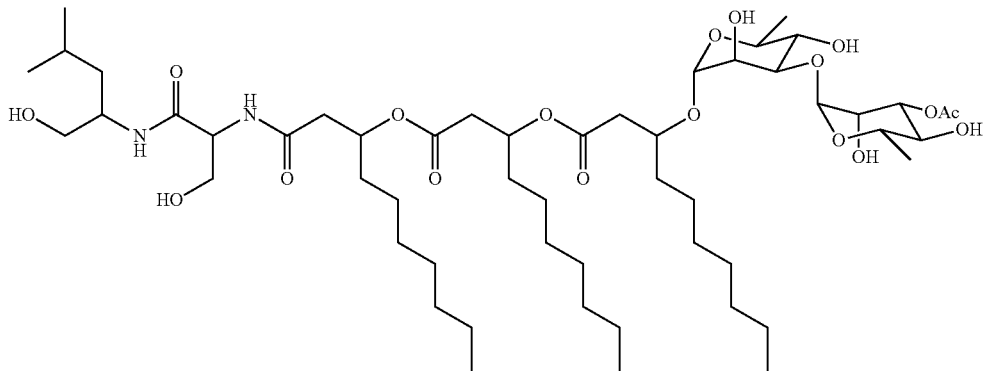 [SMILES: CCCCCCCC(CC(=O)NC(CO)C(=O)NC(CO)CC(C)C)OC(=O)CC(CCCCCCC)OC(=O)CC(CCCCCCC)OC1OC(C)C(O)C(OC2OC(C)C(O)C(OC(C)=O)C2O)C1O]

The described fractionation scheme also yielded several other glycolipopeptide analogues produced by *V. paradoxus* RKNM-096 in smaller quantities, including 10.9 mg of NB-RLP978. The $^1$H and $^{13}$C NMR data were nearly identical to that of NB-RLP1006. The apparent molecular formula of NB-RLP978 is $C_{49}H_{90}N_2O_{17}$ (HRESIMS m/z 979.6307 [M+H]$^+$, calcd for $C_{49}H_{91}N_2O_{17}$, 979.6312). On the basis of tandem mass spectrometry, NB-RLP978 was determined to be an inseparable mixture of three closely related analogues, NB-RLP978A, NB-RLP978B, and NB-RLP978C, containing a $C_8$ acyl chain at one of the 3-hydroxyalkanoic acid positions.

The chemical structure of NB-RLP978A-C is:

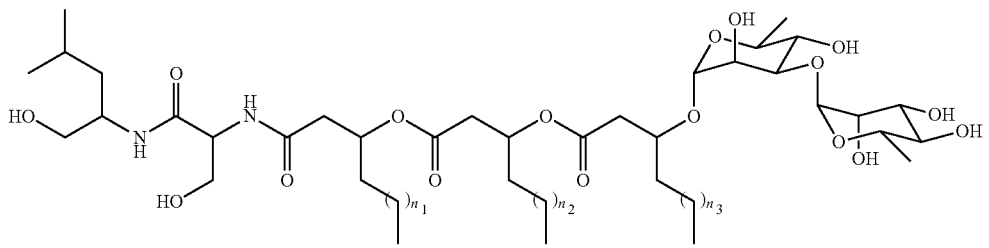

where any single acyl chain is $C_8$ (i.e. $n_1$, $n_2$, or $n_3$=3) while the remaining acyl chains are $C_{10}$ (i.e. n=5). NB-RLP978A: $n_1$=$n_2$=5, $n_3$=3; NB-RLP978B: $n_1$=$n_3$=5, $n_2$=3; NB-RLP978C: $n_1$=3, $n_2$=$n_3$=5.

The reversed-phase HPLC purification of NB-RLP1006 and NB-RLP978A-C also yielded NB-RLP950, an inseparable mixture of compounds with an apparent molecular formula of $C_{47}H_{86}N_2O_{18}$ (HRESIMS m/z 951.5982 [M+H]$^+$, calcd for $C_{47}H_{87}N_2O_{18}$, 951.5999), which is consistent with an analogue of NB-RLP1006 lacking four methylene groups. The $^1$H NMR spectrum of NB-RLP950 was nearly identical to that of NB-RLP1006 and NB-RLP978. A $^{13}$C spectrum was not obtained due to insufficient material. On the basis of tandem mass spectrometry, NB-RLP950 was determined to be a mixture of six closely related analogues: NB-RLP950A, NB-RLP950B, NB-RLP950C, NB-RLP950D, NB-RLP950E, and NB-RLP950F. These glycolipopeptide analogues either contain two $C_8$ acyl chains or one $C_6$ acyl chain at the 3-hydroxyalkanoic acid positions.

The chemical structure of NB-RLP950A-F is:

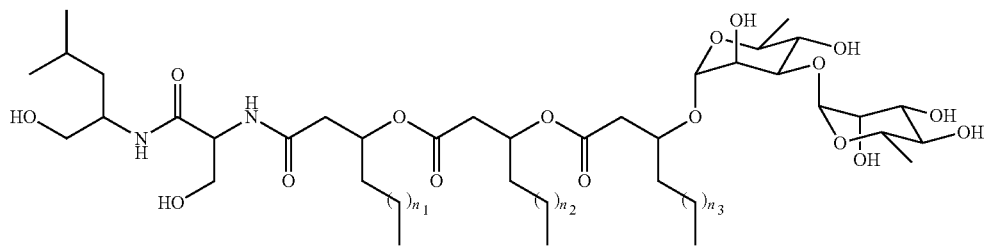

where any two acyl chains are $C_8$ (e.g. $n_1=n_2=3$ and $n_3=5$) while the remaining acyl chain is $C_6$ (i.e. $n=1$). NB-RLP950A: $n_1=5$, $n_2=n_3=3$; NB-RLP950B: $n_2=5$, $n_1=n_3=3$; NB-RLP950C: $n_3=5$, $n_1=n_2=3$; NB-RLP950D: $n_1=n_2=5$, $n_3=1$; NB-RLP950E: $n_1=n_3=5$, $n_2=1$; NB-RLP950F: $n_2=n_3=5$, $n_2=1$.

The reversed-phase HPLC purification of NB-RLP1048B also yielded NB-RLP1020. The $^1$H and $^{13}$C NMR data of NB-RLP1020 were nearly identical to that of NB-RLP1048B. The apparent molecular formula of NB-RLP1020 is $C_{51}H_{92}N_2O_{18}$ (HRESIMS m/z 1021.6415 [M+H]$^+$, calcd for $C_{51}H_{93}N_2O_{18}$, 1021.6418). On the basis of tandem mass spectrometry, NB-RLP1020 was determined to be an inseparable mixture of three closely related analogues, NB-RLP1020A, NB-RLP1020B, and NB-RLP1020C, comprising a $C_8$ acyl chain at one of the 3-hydroxyalkanoic acid positions.

The chemical structure of NB-RLP1020A-C is:

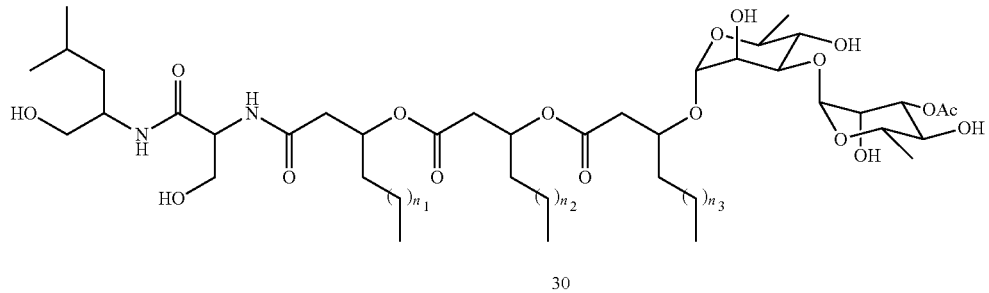

where any single acyl chain is $C_8$ (i.e. $n_1$, $n_2$, or $n_3=3$) while the remaining acyl chains are $C_{10}$ (i.e. $n=5$). NB-RLP1020A: $n_1=n_2=5$, $n_3=3$; NB-RLP1020B: $n_1=n_3=5$, $n_2=3$; NB-RLP1020C: $n_1=3$, $n_2=n_3=5$.

The reversed-phase HPLC fractionation also yielded an inseparable mixture of compounds with an apparent molecular formula of $C_{51}H_{92}N_2O_{18}$ (HRESIMS m/z 1021.6477 [M+H]$^+$, calcd for $C_{51}H_{93}N_2O_{18}$, 1021.6418). Similar to NB-RLP1020A-C, the structure of these compounds is:

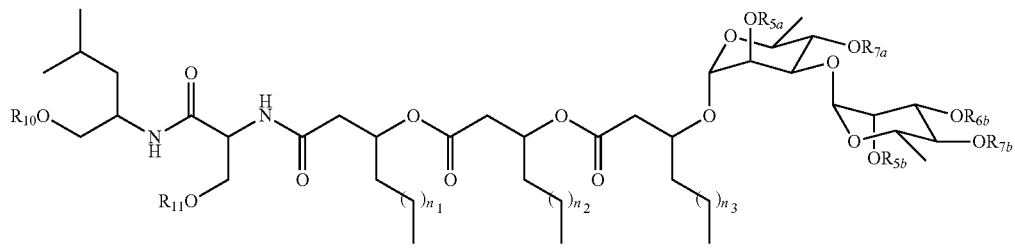

where any single R-group is an acetyl group, while all other R-groups are hydrogen atoms and where any single acyl chain is $C_8$ (i.e. $n_1$, $n_2$, or $n_3=3$) while the remaining acyl chains are $C_{10}$ (i.e. $n=5$).

The reversed-phase HPLC fractionation also yielded NB-RLP1076. The $^1$H and $^{13}$C NMR data were nearly identical to that of NB-RLP1020A-C and NB-RLP1048B. The apparent molecular formula of NB-RLP1076 is $C_{55}H_{100}N_2O_{18}$ (HRESIMS m/z 1077.7046 [M+H]$^+$, calcd for $C_{55}H_{101}N_2O_{18}$, 1077.7044). On the basis of tandem mass spectrometry, NB-RLP1076 was determined to be an inseparable mixture of three closely related analogues, NB-RLP1076A, NB-RLP1076B, and NB-RLP1076C, comprising a $C_{12}$ acyl chain at one of the 3-hydroxyalkanoic acid positions.

The chemical structure of NB-RLP1076A-C is:

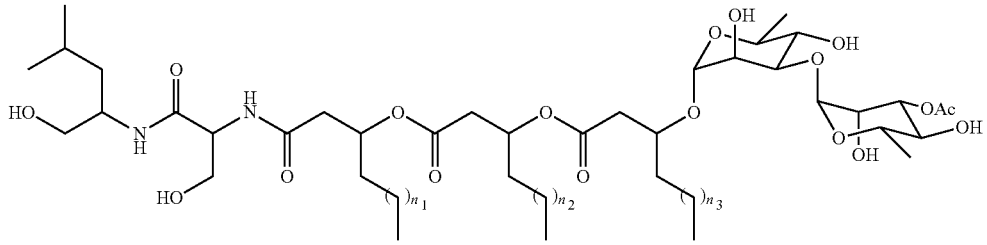

where any single acyl chain is $C_{12}$ (i.e. $n_1$, $n_2$, or $n_3=7$) while the remaining acyl chains are $C_{10}$ (i.e. $n=5$). NB-RLP1076A: $n_1=n_2=5$, $n_3=7$; NB-RLP1076B: $n_1=n_3=5$, $n_2=7$; NB-RLP1076C: $n_1=7$, $n_2=n_3=5$.

The reversed-phase HPLC fractionation also yielded an inseparable mixture of compounds with an apparent molecular formula of $C_{55}H_{100}N_2O_{18}$ (HRESIMS m/z 1077.7098 [M+H]$^+$, calcd for $C_{55}H_{101}N_2O_{18}$, 1077.7044). Similar to NB-RLP1076A-C, the structure of these compounds is:

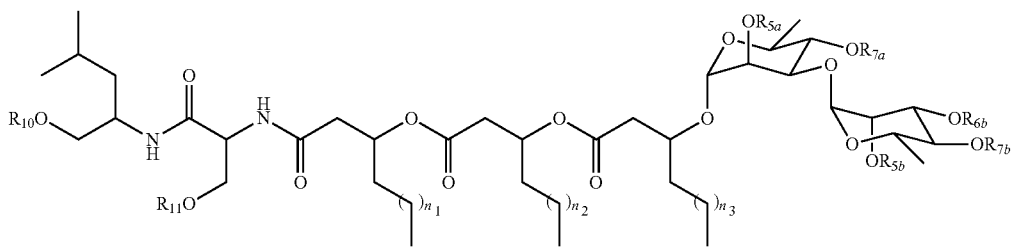

where any single R-group is an acetyl group, while all other R-groups are hydrogen atoms and where any single acyl chain is $C_{12}$ (i.e. $n_1$, $n_2$, or $n_3=7$) while the remaining acyl chains are $C_{10}$ (i.e. $n=5$).

Using portions of the *V. paradoxus* RKNM-096 glycolipopeptide biosurfactant biosynthetic gene cluster as in silico probes against published bacteria genomes (described below), we identified *Janthinobacterium agaricidamnosum* DSM 9628 as a potential producer of glycolipopeptide biosurfactants similar to those isolated from *V. paradoxus* RKNM-096. *J. agaricidamnosum* was cultured and extracted as described above for *V. paradoxus* RKNM-096 and the resulting organic extract (110.4 mg) of was subjected to automated reversed-phase chromatography with a RediSep $C_{18}$ column using a $H_2O/CH_3OH$ gradient. Fractions containing the glycolipopeptide (77.6 mg) were combined and a portion of this material was subjected to further separation by reversed-phase HPLC, which yielded 17.1 mg of NB-RLP860 and 6.4 mg of NB-RLP832. Analysis of NB-RLP860 by HRESIMS (HRESIMS m/z 861.6033 [M+H]$^+$, calcd for $C_{45}H_{85}N_2O_{13}$, 861.6046) indicated an apparent molecular formula of $C_{45}H_{84}N_2O_{13}$ and five degrees of unsaturation. The $^1H$ and $^{13}C$ NMR data of NB-RLP860 were similar to NB-RLP1006, except the NMR spectra lacked resonances belonging to the second a-rhamnopyranose moiety.

The chemical structure of NB-RLP860 was determined by 1D and 2D NMR spectroscopy. The structure of NB-RLP860 is:

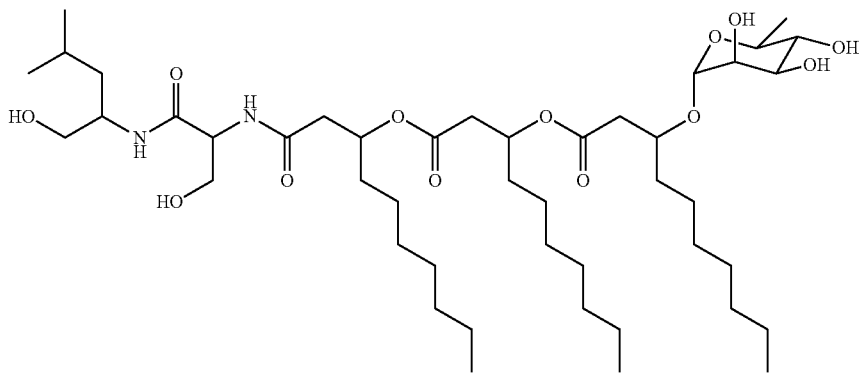 [SMILES: CCCCCCCC(CC(=O)NC(CO)C(=O)NC(CO)CC(C)C)OC(=O)CC(CCCCCCC)OC(=O)CC(CCCCCCC)OC1OC(C)C(O)C(O)C1O]

Analysis of NB-RLP832 by HRESIMS (HRESIMS m/z 833.5734 [M+H]$^+$, calcd for $C_{45}H_{81}N_2O_{13}$, 833.5733) indicated an apparent molecular formula of $C_{43}H_{80}N_2O_{13}$. The $^1$H and $^{13}$C NMR data were nearly identical to that of NB-RLP860. On the basis of tandem mass spectrometry, NB-RLP832 was determined to be an inseparable mixture of three closely related analogues, NB-RLP832A, NB-RLP832B, and NB-RLP832C, comprising a $C_8$ acyl chain at one of the 3-hydroxyalkanoic acid positions.

The chemical structure of NB-RLP832A-C is:

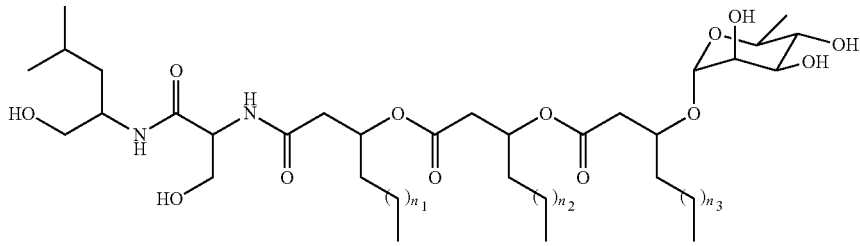

where any single acyl chain is $C_8$ (i.e. $n_1$, $n_2$, or $n_3$=3) while the remaining acyl chains are $C_{10}$ (i.e. n=5). NB-RLP832A: $n_1$=$n_2$=5, $n_3$=3; NB-RLP832B: $n_1$=$n_3$=5, $n_2$=3; NB-RLP832C: $n_1$=3, $n_2$=$n_3$=5.

Glycolipopeptides NB-RLP860 and NB-RLP832A-C were also detected in small quantities in organic extracts of V. paradoxus RKNM-096 by LC-MS analysis. Analysis of HRESIMS chromatograms revealed [M+H]$^+$ ions of m/z 861.6073 and m/z 833.5749, which are consistent with the predicted m/z of [M+H]$^+$ ions for NB-RLP860 (calcd for $C_{45}H_{85}N_2O_{13}$, m/z 861.6046 [M+H]$^+$) and NB-RLP832A-C (calcd for $C_{45}H_{81}N_2O_{13}$, m/z 833.5733 [M+H]$^+$).

Analysis of organic extracts of V. paradoxus RKNM-096 also revealed three peaks in the HRESIMS chromatogram exhibiting [M+H]$^+$ ions of m/z 903.6213, which is consistent with the predicted [M+H]$^+$ ions for an acetylated analogue of NB-RLP860 (m/z 903.6152 [M+H]$^+$). As these compounds were produced in small quantities, attempts to determine their structures unambiguously by NMR spectroscopy were prohibited. These compounds were not detected in organic extracts from J. agaricidamnosum DSM 9628. Given the observed fragment ions of m/z 715.5480 (b) and 598.4310 (bf), these compounds were identified as acetylated glycolipopeptides NB-RLP902 with the structure:

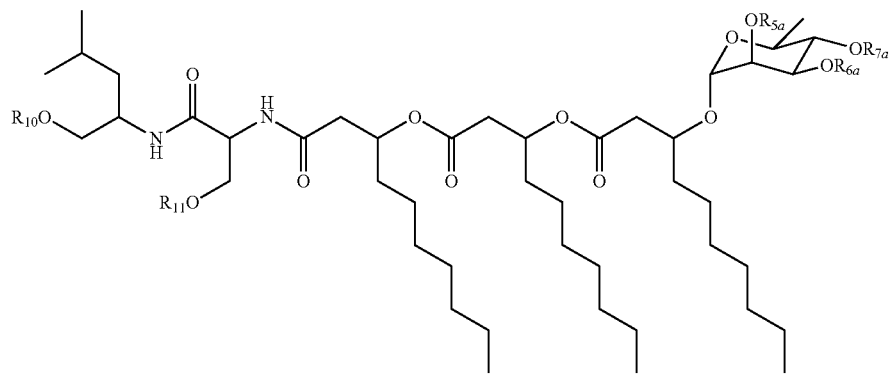

where any single R-group is an acetyl group, while all other R-groups are hydrogen atoms.

Fractions generated by automated reversed-phase chromatography of organic extracts from *V. paradoxus* RKNM-096 were enriched with NB-RLP902. Also detected in the HRESIMS chromatograms of these fractions was a small peak exhibiting a [M+H]+ ion of m/z 875.5888, which is consistent with an analogue of NB-RLP902 lacking two methylene groups. This [M+H]+ ion was not observed in organic extracts from *J. agaricidamnosum* DSM 9628. The observed fragment ion of 687.5164 (b) indicates that this compound is also a glycolipopeptide. Similar to NB-RLP978A-C, NB-RLP1020A-C, and NB-RLP832A-C, it is proposed that this peak is comprised of three compounds NB-RLP874A-C with the structure:

NB-RLP1006 with >95% purity by weight (Scheme 1). The method utilizes NaOH within a narrow concentration range to selectively remove acetate moieties without inducing further hydrolysis of the amide, ester, or glycosidic linkages of the glycolipopeptide. The NaOH concentration and reaction solvent both have a demonstrated role in controlling the extent of hydrolysis and achieving selectively. Optimal NaOH concentrations are directly proportional to the concentration and composition of the glycolipopeptides in the reaction medium. Reaction solvents with higher water composition, such as $H_2O$:acetone (9:1), showed better selectivity and minimized the hydrolysis of the ester linkages between the β-hydroxyalkanoic acid moieties.

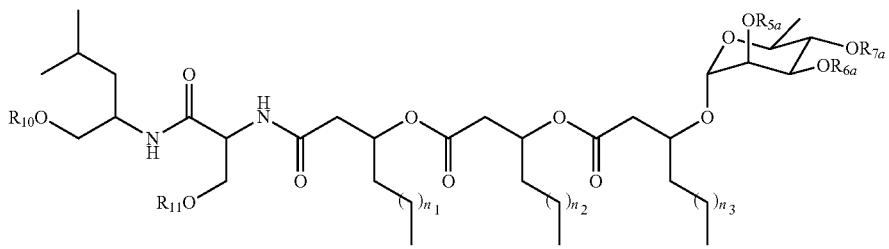

where any single R-group is an acetyl group, while all other R-groups are hydrogen atoms and where any single acyl chain is $C_8$ (i.e. $n_1$, $n_2$, or $n_3$=3) while the remaining acyl chains are $C_{10}$ (i.e. n=5).

Example 4: Deacetylation of NB-RLP1048A and Other Acetylated Glycolipopeptide Biosurfactants Produced by *Variovorax paradoxus* RKNM-096

It is known that the relative amount of NB-RLP1006 and acetylated glycolipopeptides (e.g. NB-RLP1048A) produced by *V. paradoxus* RKNM-096 may vary between batches using different culture media and fermentation conditions. As a result, the surfactant properties of the extracted glycolipopeptide product may also vary. As product consistency is important to be competitive in the biosurfactant industry, a method to selectively remove the acetate from $R_{5a}$, $R_{5b}$, $R_{6a}$, $R_{6b}$, $R_{7a}$, $R_{7b}$, $R_{10}$, and $R_{11}$ was developed to generate a consistent glycolipopeptide product comprised of Scheme 1. Selective hydrolysis of acetate moities on a mixture of glycolipopeptide biosurfactants containing acetylated analogues of NB-RLP1006 (e.g. NB-RLP1048A).

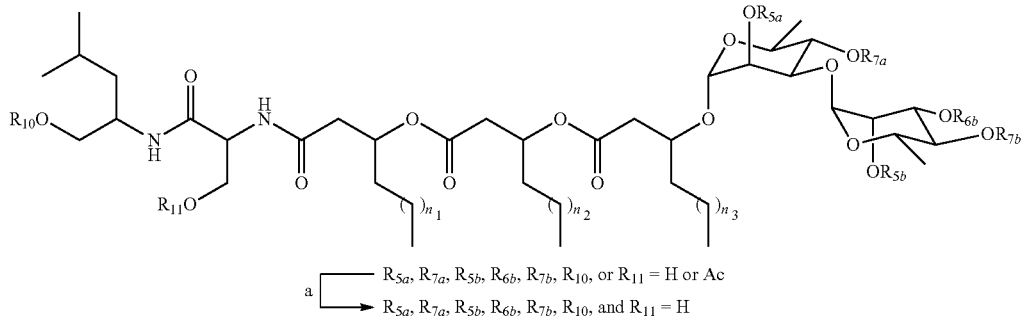

It is known that deacetylation of the glycolipopeptide mixture may be achieved with variations to the method described herein. It is possible that inorganic bases other than NaOH, including but not limited to LiOH, KOH, $Na_2CO_3$, $NH_3$, and $NH_4OH$, or organic bases, including but not limited to tetrabutylammonium hydroxide or alkylamines, may be utilized. The selective deacetylation may also be achieved enzymatically using esterases, including but not limited to acetylesterases and lipases.

Hydrolysis of the glycolipopeptide mixture is known to produce several products, including but not limited to the lipopeptides NB-RLP356 (HRESIMS m/z 357.2745 [M+H]$^+$, calcd for $C_{19}H_{37}N_2O_4$, 357.2748; m/z 379.2567 [M+Na]$^+$, calcd for $C_{19}H_{36}N_2O_4Na$, 379.2565), NB-RLP374 (HRESIMS m/z 375.2851 [M+H]$^+$, calcd for $C_{19}H_{39}N_2O_5$, 375.2854), and NB-RLP526 (HRESIMS m/z 527.4054 [M+H]$^+$, calcd for $C_{29}H_{55}N_2O_6$, 527.4055), and the glycolipids NB-RLP480 (HRESIMS m/z 481.2599 [M+H]$^+$, calcd for $C_{22}H_{41}O_{11}$, 481.2643; m/z 503.2465 [M+Na]$^+$, calcd for $C_{22}H_{40}O_{11}Na$, 503.2463) and NB-RLP650 (HRESIMS m/z 651.3962 [M+H]$^+$, calcd for $C_{32}H_{59}O_{13}$, 651.3950). Given their amphiphilic structures, these compounds are also expected to behave as surface active agents and may exhibit surfactant properties that may be unique or complementary to the glycolipopeptides. These compounds are known to be formed during the deacetylation process described herein and are thus present in the glycolipopeptide final product. Although normally present in small quantities (<5% by weight), these compounds may contribute to the surfactant characteristics of the glycolipopeptide product. Hydrolysis of the glycolipopeptides may also occur spontaneously, for instance during the extraction and purification, to generate these compounds. For instance, the lipopeptide NB-RLP374 is detected in the organic extract of *V. paradoxus* RKNM-096 before the glycolipopeptide material is subjected to any downstream modification.

The chemical structure of NB-RLP356 is:

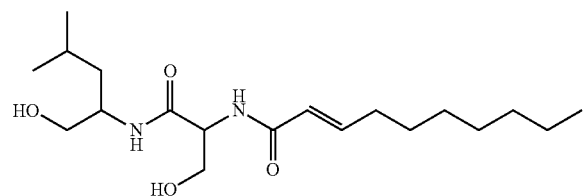 [SMILES: CCCCCCC/C=C/C(=O)NC(CO)C(=O)NC(CO)CC(C)C]

The chemical structure of NB-RLP374 is:

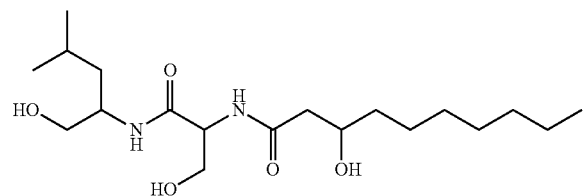 [SMILES: CCCCCCCC(O)CC(=O)NC(CO)C(=O)NC(CO)CC(C)C]

The chemical structure of NB-RLP526 is:

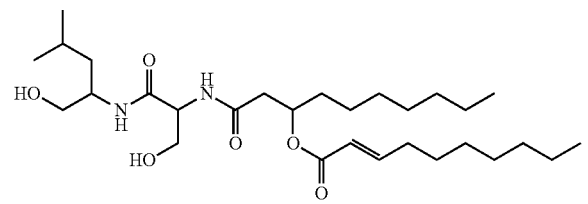 [SMILES: CCCCCCC/C=C/C(=O)OC(CCCCCCC)CC(=O)NC(CO)C(=O)NC(CO)CC(C)C]

The chemical structure of NB-RLP480 is:

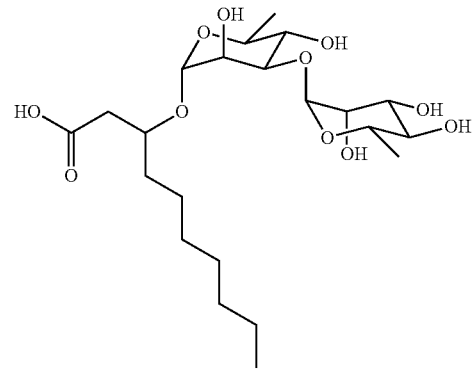 [SMILES: CCCCCCCC(CC(=O)O)OC1OC(C)C(O)C(OC2OC(C)C(O)C(O)C2O)C1O]

The chemical structure of NB-RLP650 is:

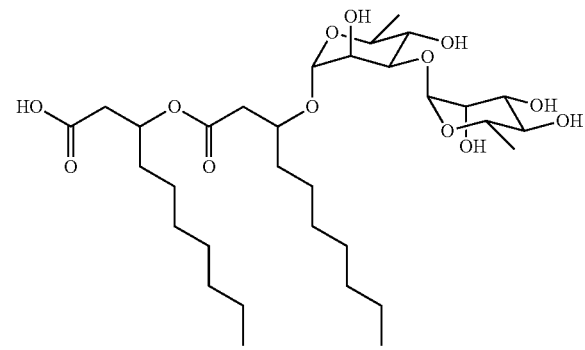 [SMILES: CCCCCCCC(CC(=O)O)OC(=O)CC(CCCCCCC)OC1OC(C)C(O)C(OC2OC(C)C(O)C(O)C2O)C1O]

Example 5: Surface Activity

As summarized in Table 1, the critical micelle concentrations (CMCs) of NB-RLP1006, NB-RLP978, NB-RLP860, and NB-RLP-1048B were determined by the Du Nouy method utilizing a Kibron Delta-8 multichannel microtensiometer (Kibron Inc., Helsinki, Finland). All samples were prepared in degassed deionized water (Millipore, Etobicoke, ON, CA) at concentrations ranging from 0 to 2.0 mM. All measurements were recorded between 24 and 25° C. and performed in duplicate. The critical micelle concentration of both NB-RLP1006 and NB-RLP978 was 0.20 mM (0.02 wt %). Surface tension measurements indicated that NB-RLP1006 and NB-RLP978 were capable of reducing the surface tension of water from 72 to 35.5 mN/m at their CMC. Meanwhile, NB-RLP860 and NB-RLP1048B exhibited CMC values of 0.85 mM (0.07 and 0.09 wt %, respectively), reducing the surface tension of water to 36.2 and 36.9 mN/m, respectively. The surface activity of NB-RLP1006 was compared to rhamnolipids A and B, which were purified from a commercially available rhamnolipid mixture (R90; AGAE Technologies, Corvallis, OR, USA) by reversed-phase HPLC. Rhamnolipids A and B both exhibited a CMC of 0.06 mM (0.003 and 0.004 wt %, respectively) in which the surface tension of water was reduced to 28.2 and 39.0 mN/m, respectively. The higher CMC values for NB-RLP860 and NB-RLP1048B may be due to their poor aqueous solubility.

TABLE 1

Surfactant properties of isolated glycolipopeptides compared to rhamnolipids. Critical micelle concentration (CMC) and surface tension reduction of water are shown.

| Compound | CMC (mM) | Minimum Surface Tension (mN/m) |
|---|---|---|
| NB-RLP1006 | 0.20 | 35.5 |
| NB-RLP1048B | 0.85 | 36.9 |
| NB-RLP860 | 0.85 | 36.2 |
| NB-RLP978 | 0.20 | 35.5 |
| Rhamnolipid A | 0.06 | 28.2 |
| Rhamnolipid B | 0.06 | 39.0 |

The characteristic curvature (Cc) of NB-RLP1006 was determined using the hydrophilic-lipophilic difference-net average curvature (HLD-NAC) model to calculate the shift in chemical potential when NB-RLP1006 is transferred from the oil to the aqueous phase as a function of salinity by the following general equation:

$$HLD = F(S) - k \times EACN + F(A) - \alpha \times \Delta T + Cc$$

where F(S) is a function of salinity, k is a coefficient equal to 0.17, EACN (effective alkane carbon number) is the number of carbons in the alkane oil phase, α is a coefficient dependent on the type of surfactant (ionic, ethoxylates, etc), and ΔT is the effect of temperature. Four mixtures of NB-RLP1006 and sodium dihexyl sulfosuccinate (SDHS) were prepared with a total surfactant concentration of 1.8 mg/mL using the following NB-RLP1006/SDHS ratios: 0, 12, 24, and 40 wt % NB-RLP1006. An electrolyte scan was performed for each mixture by varying the NaCl concentration from 0 to 6.0% (w/v). Each mixture was added to an equal volume of toluene, which constituted the oil phase, and shaken vigorously. The optimal salinity (S*) was identified as the concentration of NaCl in which a Winsor Type III microemulsion was formed, wherein the separate middle phase was composed of an equal volume of oil and water. A plot of the NB-RLP1006/SDHS molar ratios versus S* was generated and Cc was calculated from the line of best fit. The Cc value for NB-RLP1006 was determined to be +5.2, a value that reflects the hydrophobic nature of this biosurfactant.

The emulsifying properties of NB-RLP1006 were determined using the emulsification index as described above. Pure NB-RLP1006 exhibited strong emulsification activity with an $E_{24}$ value of 53% at 1 mg/mL in deionized water. The emulsification of NB-RLP1006 is pH-dependent with $E_{24}$ values of 8, 38, and 31% at pH 3, 6, and 8, respectively. The type of emulsion formed by NB-RLP1006 (e.g. oil-in-water or water-in-oil) was determined using the drop dilution test. An emulsion was formed by vigorously mixing a 1 mg/mL solution of RLP1006 in deionized water with an equal volume of kerosene for 1 min. A portion (20 µL) of the emulsion was transferred to 0.5 mL of deionized water and 0.5 mL of kerosene and dilution of the emulsion in each liquid was monitored. The emulsion formed by NB-RLP1006 was readily dispersed in the aqueous phase, indicating that the continuous phase of the emulsion was water and that an oil-in-water (o/w) emulsion was formed by NB-RLP1006 under these conditions.

These results established that NB-RLP1006 is a potent biosurfactant capable of lowering the surface tension of water to 35.5 mN/m with a CMC comparable to that of two other well-characterized biosurfactants, rhamnolipids A and B. NB-RLP1006 also exhibits strong emulsification activity forming o/w emulsions under the conditions described herein.

Example 6: Cytotoxicity Testing of the Glycolipopeptides

To evaluate the safety profile of the glycolipopeptides, cytotoxicity testing was conducted against two normal human cell lines, BJ fibroblast cells ATCC CRL-2522 and adult epidermal keratinocytes (HEKa; Life Technologies, Carlsbad, CA, USA). BJ fibroblasts were grown and maintained in 15 mL Eagle's minimal essential medium supplemented with fetal bovine serum (10% v/v), penicillin (100 µU) and streptomycin (100 µg/mL). HEKa cells were grown and maintained in 15 mL of EPI life medium (Life Technologies, Carlsbad, CA, USA) supplemented with HKGS growth supplement (10% v/v; Life Technologies, Carlsbad, CA, USA) and 50 µg/mL gentamicin (Sigma-Aldrich, St. Louis, MO, USA). Cells were cultured in T75cm$^2$ cell culture flasks and incubated at 37° C. in a humidified atmosphere of 5% $CO_2$. For BJ fibroblasts culture media was refreshed every two to three days and cells were not allowed to exceed 80% confluence. For HEKa cells growth medium was refreshed every 2 d until the cells reached 50% confluence and then the medium was refreshed every 24 h until 80% confluence was obtained. At 80% confluence, the cells were counted, diluted to 10,000 cells/well in growth medium lacking antibiotics and 90 µL of cell suspension was transferred into the wells of 96-well treated cell culture plates. The plates were incubated as before to allow cells to adhere to the plates for 24 h before treatment. DMSO was used as the vehicle at a final concentration of 1%. All compounds tested were re-solubilized in DMSO and a dilution series was prepared for each cell line using the respective cell culture growth medium, 10 µL of which were added to the assay wells yielding eight final concentrations ranging from 512 µg/mL to 8 µg/mL per well (final well volume of 100 µL). The fibroblasts and HEKa cells were incubated as previously described for 24 h. All samples were tested in triplicate. Each plate contained four un-inoculated media blanks (media+1% DMSO), four untreated growth controls (media+1% DMSO+cells), and one column containing a serially diluted zinc pyrithione positive control. AlamarBlue (Life Technologies, Carlsbad, CA, USA) was added to each well 24 h after treatment (10% v/v). Fluorescence (560/12 excitation, 590 nm emission) was monitored using a Varioskan Flash Multimode plate reader both at time zero and 4 h after the addition of alamarBlue. After subtraction of fluorescence at time zero from 4 h readings the percentage of cell viability relative to vehicle control wells was calculated. Low cytotoxic activity was displayed against the HEKa and BJ fibroblast cell lines. The observed $IC_{50}$ and $MIC_{90}$ values for the glycolipopeptides were significantly higher than the positive control zinc pyrithione, which served as an industry benchmark for topical antimicrobial agents (Table 2). These results indicate that the glycolipopeptides exhibit low cytotoxicity towards human skin cells and thus may be safe for use in applications which result in dermal contact such as cosmetic products.

TABLE 2

Cytotoxicity testing results for the glycolipopeptides. Values indicate the half maximal inhibitory concentrations ($IC_{50}$) and minimum inhibitory concentration that results in 90% of growth inhibition ($MIC_{90}$) in µg/mL. Error is reported as standard deviation.

| | Eukaryotic Cells | | | |
|---|---|---|---|---|
| Compound | HEKa ($IC_{50}$) | HEKa ($MIC_{90}$) | BJ ($IC_{50}$) | BJ ($MIC_{90}$) |
| NB-RLP1006 | 15.5 ± 1.7 | 64-128 | 19.5 ± 2.4 | 32 |
| NB-RLP1048B | 19.3 ± 4.0 | 64-128 | 18.7 ± 1.6 | 32 |
| NB-RLP860 | 15.5 ± 1.6 | 128 | 16.3 ± 0.3 | 32 |
| Zinc pyrithione | 0.20 ± 0.001 | 1 | 2.2 ± 0.3 | 4 |

Example 7: Sequencing of the *V. paradoxus* RKNM-096 Glycolipopeptide and Rhamnose Biosynthetic Gene Clusters To establish the genetic basis for the biosynthesis of the novel glycolipopeptide biosurfactants described here, the genome of *V. paradoxus* RKNM-096 was sequenced. *V. paradoxus* RKNM-096 was cultured in ISP2 broth and genomic DNA was isolated using the UltraClean® Microbial DNA Isolation Kit according to the manufacturer's recommendations (Mo Bio, Carlsbad, CA, USA). The genome was sequenced at the McGill University and Genome Quebec Innovation Centre (Montreal, QC, CA) using 2 SMRT Cells in a PacBio RSII sequencer (Pacific Biosciences, Menlo Park, CA, USA). A total of 140, 476 raw subreads with an average length of 11,269 bpwere generated and genome assembly was achieved using a HGAP workflow (Chin et al. [2013] *Nature Methods* 10, 563). Briefly, raw subreads were generated from raw .bas.h5 PacBio data files. A subread length cutoff value (30×) was extracted from subreads and used in the preassembly (BLASR) step, which consists of aligning short subreads on long subreads (Chaisson and Tesler [2012] *BMC Bioinformatics* 13, 238). Since errors in PacBio reads are random, the alignment of multiple short reads on longer reads enables correction of sequencing errors on long reads. These long corrected reads were then used as seeds in a subsequent assembly prepared using the Celera assembler (Myers et al. [2000] *Science* 287, 2196), which generates contigs. These contigs were then 'polished' by aligning raw reads on contigs (BLASR) which were then processed through a variant calling algorithm (Quiver) that generates high quality consensus sequences using local realignments and PacBio quality scores (Chin et al. [2013] *Nature Methods* 10, 563). Over 161,717,463 bp of corrected long subreads were obtained and resulted in the assembly of two contigs. One contig contained 7,193,071 bp while the other contained 1,767 bp. The genome was annotated using the RAST server (Aziz et al. [2008] *BMC Genomics* 9, 75; Overbeek et al. [2014] *Nucleic Acid Res.* 42, D206; Brettin et al. [2015] *Sci Rep.* 5, 8265). The function of open reading frames (ORFs) identified by the RAST annotation were further explored by BLASTP (Altscul et al. [1997] *Nucleic Acids Res.* 25, 3389) and conserved domain (Marchler-Bauer and Bryant [2004] *Nucleic Acids Res.* 32, W327) analysis of deduced amino acid sequences.

Based on the structure of NB-RLP1006 it was hypothesized that its biosynthesis would require a NRPS to synthesize the dipeptide, one or more acyltransferases to acylate the peptide and generate the 3-(3-(3-hydroxydecanoyloxy) decanoyloxy) decanoyl moiety and one or more glycosyltransferases. Scanning the genome for genes encoding NRPSs identified two loci. One locus contained a single NRPS-encoding gene followed by two glycosyltransferases, thus this locus (12,721 bp) was analyzed further. Six ORFs were identified in this locus, which were predicted to play an integral role in glycolipopeptide biosynthesis (Table 3). The six genes, designated rlpA to rlpE, are oriented in the same direction and form a contiguous region in the *V. paradoxus* RKNM-096 genome.

TABLE 3

Deduced functions of Orfs identified in the *V. paradoxus* RKNM-096 glycolipopeptide (Seq. ID: 1) and dTDP-L-rhamnose biosynthetic gene clusters (Seq. ID: 2).

| Seq. ID. (DNA) | Source | Name | Start | Stop | Seq. ID. (protien) | Size (aa) | Proposed Function |
|---|---|---|---|---|---|---|---|
| 3 | Seq. ID: 1 | rlpA | 121 | 1035 | 4 | 304 | LysR transcriptional regulator |
| 5 | Seq. ID: 1 | rlpB | 1437 | 8912 | 6 | 2491 | Nonribosomal peptide synthetase |
| 7 | Seq. ID: 1 | rlpC | 8924 | 10243 | 8 | 439 | dTDP-rhamnosyl transferase |
| 9 | Seq. ID: 1 | rlpD | 10276 | 10488 | 10 | 70 | MbtH protein |
| 11 | Seq. ID: 1 | rlpE | 10497 | 11465 | 12 | 322 | dTDP-rhamnosyl transferase |
| 13 | Seq. ID: 1 | rlpF | 11462 | 12721 | 14 | 419 | MFS transporter |
| 15 | Seq ID: 2 | rmlB | 299 | 1378 | 16 | 359 | dTDP-glucose 4,6-dehydratase |
| 17 | Seq ID: 2 | rmlD | 1375 | 2265 | 18 | 296 | dTDP-4-dehydrorhamnose reductase |
| 19 | Seq ID: 2 | rmlA | 2298 | 3194 | 20 | 298 | Glucose-1-phosphate thymidylyltransferase |
| 21 | Seq ID: 2 | rmlC | 3191 | 3736 | 22 | 181 | dTDP-4-dehydrorhamnose 3,5-epimerase |

Genes involved in regulation. The first gene, rlpA, encodes a protein that exhibits similarity to transcriptional regulators belonging to the LysR family. Conserved domain analysis indicated that RlpA contained an amino-terminal helix-turn-helix domain and a carboxy-terminal LysR substrate binding domain, which is consistent with the domain architecture of LysR transcriptional regulators. This family of regulators can function as transcriptional activators or repressors (Maddocks and Oyston [2009] *Microbiology* 154, 3609), thus it is likely that R1pA plays a role in the regulation of glycolipopeptide biosynthesis.

Genes involved in peptide biosynthesis. Following rlpA is large gene, rlpB, (7,476 bp), which encodes a NRPS. Domain analysis (Bachmann and Ravel [2009] *Meth. Enzymol.* 458, 181) indicated that that the NRPS consists of two modules (M1 and M2) with the following domain organization (C-A-PCP)$_{M1}$-(C-A-PCP-R)$_{M2}$. The dimodular structure and domain organization suggests that RlpB generates a dipeptide, which is consistent with structure of the *V.*

*paradoxus* RKNM-096 glycolipopeptides. The first domain of the first module of RlpB is a condensation domain. The presence of a C-domain at the beginning of a NRPS initiation module is characteristic of acylated peptides. Aminoterminal C-domains can catalyze amide bond formation between the first amino acid of a peptide and a fatty acid. The fatty acid can be presented to the C-domain as an acyl-ACP intermediate, as in the case of CDA biosynthesis (Kopp et al. [2008] *J. Am. Chem. Soc.* 130, 2656), or an acyl-CoA intermediate, as in the case of surfactin biosynthesis (Krass et al. [2010] *Chem. Biol.* 17, 872). A phylogenetic analysis of the RlpB initiation module C-domain (residues 12-437) was conducted using the NaPDoS program (Ziemert et al. [2012] *PLoS One* 7, e34064). The RlpB domain clustered closely with C-domains from initiation modules that catalyze the condensation of a fatty acid precursor with an amino acid. The most closely related C-domain in the NaPDoS reference database was the initiation module of the bacillibactin NRPS (38% identity), which catalyzes the condensation of 2,3-dihydroxybenzoyl-ACP with glycine (May et al. [2001] *J. Biol. Chem.* 278, 7209). This suggests that glycolipopeptide biosynthesis starts with the condensation of a fatty acid with the first amino acid of the peptide (serine). Similar analysis of the second C-domain indicated it was most closely related to the second C-domain of the bacillibactin dimodular NRPS, DhbF (54% identity). Phylogenetic analysis revealed that the M2 C-domain of RlpB clustered with C-domains catalyzing the condensation of two L-amino acids (Ziemert et al. [2012] *PLoS One* 7, e34064), which is consistent with the glycolipopeptide structure.

To predict the substrate specificity of the RlpB A-domains, the substrate specificity codes were extracted from the A-domain active sites (8 residues between motifs A3 and A6) and compared to known A-domain specificity codes using the NRPS Predictive Blast tool (Bachmann and Ravel [2009] *Meth. Enzymol.* 458, 181). The specificity code of the M1 A-domain was most similar to A-domains from the nostopeptolide, pyoverdin, CDA and enterobactin NRPSs that activate L-serine (75-87% identity, 87-100% similarity, E-value 0.023-0.039), suggesting that L-serine is incorporated by M1. This observation is consistent with the structure of the glycolipopeptides. The M2 A-domain specificity code showed low homology (50% identity, 100% similarity, E-value 0.98) to an A-domain of the tyrocidine NRPS (TycB), which activates L-phenylalanine or L-tryptophan (Mootz and Marahiel [1997] *J. Bacteriol.* 179, 6843). This low level of similarity precludes prediction of the substrate specificity of this A-domain. Based on the structure of the *V. paradoxus* RKNM-096 glycolipopeptides the second A-domain would be expected to activate L-leucine. Comparison of the A-domain specificity code of RlpB module 2 to leucine specificity codes (Stachelhaus et al. [1999] *Chem. Biol.* 6, 493) also revealed low similarity, thus the RlpB M2 A-domain specificity code may represent a novel variant for leucine, although biochemical evidence would be need to establish the substrate specificity of this domain. The PCP domains of RlpB were also analyzed and both were found to contain the core PCP domain motif with an invariant serine which represents the 4'-phosphopantetheine attachment site (Konz and Marahiel [1999] *Chem. Biol.*6, R39).

The final domain of RlpB is an R-domain. R-domains utilize NAD(P)H as a co-factor to reductively release PCP-bound final products as an aldehyde or alcohol (Du and Lou [2010] *Nat. Prod. Rep.* 27, 255). The presence of a leucinol residue at the carboxy-terminus of the glycolipopeptide dipeptide moiety is consistent with release of an acylated dipeptide intermediate by an R-domain. Collectively, the domain structure and organization of RlpB, as well as the predicted substrate specificity of the individual domains are consistent with the structure of the glycolipopeptides produced by *V. paradoxus* RKNM-096.

A small gene (rlpD) encoding a 70 amino acid protein that shows similarity to MbtH-like proteins was found downstream of rlpB. These proteins are often found in association with NRPSs and have been demonstrated to be essential for non-ribosomal peptide the production. (Baltz [2014] *J. Ind. Microbiol. Biotechnol.* 41, 357). Recently these proteins have been shown to facilitate adenylation reactions via direct interaction with A-domains (Herbst et al. [2013] *J. Biol. Chem.* 288, 1991). Thus we predict that RlpD interacts with one or both A-domains of RlpB to facilitate dipeptide formation.

Genes involved in glycosylation. Glycosylation of the acylated dipeptide generated by RlpB is likely catalyzed by two ORFs (rlpC and E) downstream of rlpB. The deduced amino acid sequence of rlpC (439 aa) shows similarity to the GT1 family of glycosyltransferases, which utilize activated sugars as substrates to transfer sugar moieties to a diverse array of acceptor molecules (Breton et al. [2006] *Glycobiology* 16, 29R). The deduced amino acid sequence of rlpE (322 aa) shows similarity to dTDP-rhamnosyltransferases. In rhamnolipid biosynthesis two glycosyltransferases are utilized to sequentially transfer two rhamnosyl units to the lipid component of rhamnolipid (Deziel et al. [2003] *Microbiology* 149, 2005). RhlB transfers rhamnose from dTDP-L-rhamnose to the free β-hydroxyl group of 3-(3'-hydroxydecanoyloxy)decanoic acid (HDD) to generate mono-RL, while di-RL is formed by the transfer of an additional rhamnose from dTDP-L-rhamnose to mono-RL by RhlC (Abdel-Mawgoud et al. [2011] in *Biosurfactants*, Springer-Verlag, Berlin Heidelberg). The relationship between RlpC and RlpE and the RhlB and RhlC homologs from *P. aeruginosa* PAO1, *B. thialandensis* E264 and *B. psuedomallei* 1710B was investigated via the generation of a phylogenetic tree (unweighted pair group method with arithmetic mean method). In this analysis RlpC clustered with the RhlB orthologs while RlpE clustered with the RhlC orthologs. While RlpC clustered with the RhlB orthologs, it did not cluster tightly as it showed limited sequence identity with these enzymes (18.6-23.1%). In contrast, RlpE shared between 39.6-40.7% identity with the RhlC orthologs. This data suggests that RlpC and RlpE perform similar functions as RhlB and RhlC, respectively. We hypothesize that RlpC catalyzes the rhamnosylation of an acylated dipeptide intermediate utilizing dTDP-L-rhamnose as the carbohydrate donor. The limited sequence homology between RlpC and the RhlB orthologs may reflect the significant difference in glycosylation substrates utilized by the enzymes. RlpE is predicted to catalyze the second glycosylation reaction, transferring rhamnose from dTDP-L-rhamnose to the RlpC reaction product.

Genes encoding dTDP-L-rhamnose biosynthesis were not found in close proximity to the glycolipopeptide gene cluster. Scanning the genome for homologs of *P. aeruginosa* PAO1 rhamnose biosynthetic genes (rmlBDAC) identified four genes that exhibited strong sequence similarity to those from *P. aeruginosa* (identity/similarity: RmlB—79%/89%, RmlD—60%/71%, RmlA—78%/89%, RmlC—66%/80%). In the *V. paradoxus* RKNM-096 genome the four genes are clustered and are found in the same order as in *P. aeruginosa* (rmlBDAC) (Rahim et al. [2000] *Microbiology* 146, 2803). This locus likely provides the dTDP-L-rhamnose substrates utilized by RlpC and RlpE. Modulation of expression of one or more components of the dTDP-L-rhamnose biosynthetic pathway by one skilled in the art may be an effective approach to increase glycolipopeptide yields.

Genes involved in transport. Directly downstream of rlpE is an ORF (rlpF) encoding a protein, which is similar to major facilitator superfamily transporters from a variety of bacteria. RlpF exhibits 38% identity and 54% similarity to PA1131 from *P. aeruginosa* PAO1, which is immediately upstream of rhlC (Dubeau [2009] *BMC Microbiol* 9, 263). RlpF is likely involved in glycolipopeptide efflux.

Genes involved in the biosynthesis of the lipid moiety. In rhamnolipid biosynthesis the HDD moiety is produced by RhlA, which condenses two β-hydroxydecanoyl-ACP molecules from fatty acid biosynthesis to yield 3-(3'-hydroxydecanoyloxy)decanoic acid. Scanning of the *V. paradoxus* RKNM-096 genome for RhlA homologs did not identify any proteins with significant similarity to RhlA. Thus generation of the lipid moiety of the RKNM-096 glycolipopeptides is likely directed by a novel, yet to be identified mechanism.

Genes involved in glycolipopeptide acetylation. Acetylated analogues of NB-RLP1006 are abundant in *V. paradoxus* RKNM-096 fermentation broths. No genes encoding acetyltransferases were identified in the gene cluster. Thus it is likely that acetylation is catalyzed by an enzyme encoded elsewhere in the *V. paradoxus* RKNM-096 genome.

Proposed biosynthesis. Glycolipopeptide biosynthesis presumably starts with the formation of the 3-(3-(3-hydroxydecanoyloxy)decanoyloxy)decanoyl moiety via a yet to be identified mechanism. After formation of the lipid moiety it is likely presented to the C-domain of RlpB M1 which condenses the lipid moiety with L-serine. RlpB M2 then incorporates L-leucine to form a PCP-bound acylated dipeptide intermediate which is released from the enzyme by the C-terminal R-domain of RlpB, resulting in the formation of a terminal L-leucinol residue. dTDP-L-Rhamnose, produced by the rmlBDAC operon, is then utilized by the rhamnosyltransferases RlpC and RlpE to sequentially glycosylate the aglycone resulting in the production of the final glycosylated glycolipopeptide NB-RLP1006. NB-RLP1006 would serve as a substrate for acetylation to form NB-RLP1048A and NB-RLP1048B.

Figure 2:
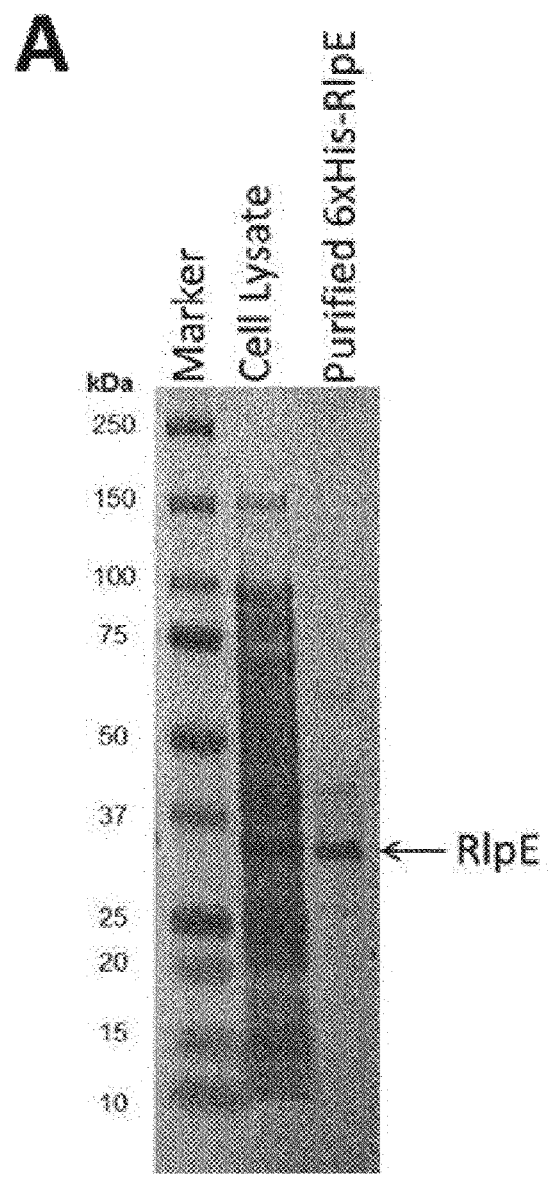
FIG. 2 is a denaturing polyacrylamide gel showing purified His-tagged RlpE (A) and the UPLC-HRMS analysis of enzyme reactions in which the enzyme was incubated with NB-RLP860 and dTDP-L-rhamnose.
Figure 2:
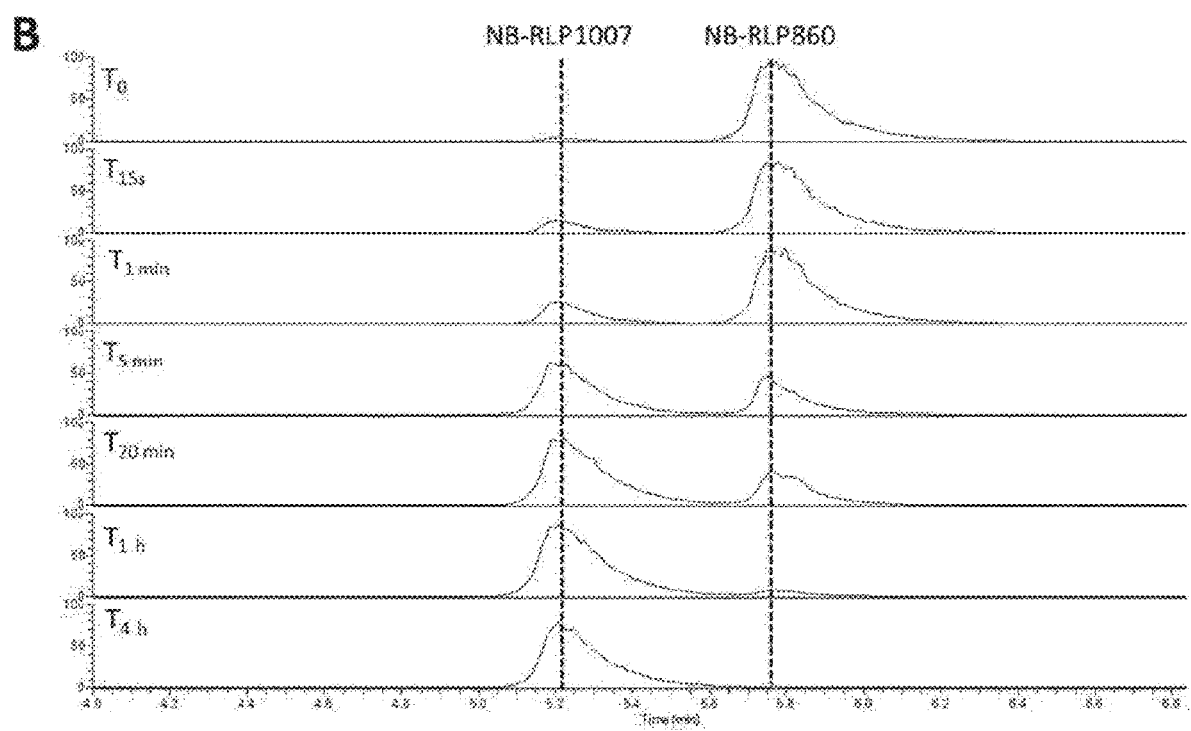

To prove the involvement of the rlpA-rplF gene cluster in the biosynthesis of glycolipopeptides in *V. paradoxus* RKNM-096 rlpE was expressed in *E. coli* and the activity of the enzyme demonstrated using NB-RPL860 as a substrate. Bioinformatics analysis indicated RlpE catalyzes the second rhamnosylation in glycolipopeptide biosynthesis, converting mono-rhamnosylated glyclipopeptides (e.g. NB-RLP832 and NB-RLP860) to di-rhamnosylated glycolipopeptides (e.g. NB-RLP978 and NB-RLP1006). The rlpE gene was cloned in pET28a (EMD Millipore, Darmstadt, DE) with an amino-terminal hexa-histidine tag using standard cloning techniques and mutation-free cloning was verified by sequencing. Due to the high GC content of rlpE, *E. coli* Rossetta DE3 pLysS (EMD Millipore) was chosen as the expression host as this strain expresses tRNAs for rare GC-rich codons (AGG, CCA, GGA). A single colony was used to inoculate 50 mL of LB Miller (EMD Millipore) supplemented with 50 µg/mL of kanamycin (Sigma-Aldrich) and 34 µg/mL of chloramphenicol (Sigma-Aldrich) and the flask was incubated at 37° C. with shaking at 250 rpm overnight. Expression cultures (50 mL) were performed in LB Miller supplemented with kanamycin and chloramphenicol. These cultures were inoculated with 0.5 mL of the overnight culture and cultured at 37° C. and 250 rpm until the optical density (600 nm) reached 0.5, following which IPTG was added to a final concentration of 1.0 mM to induce protein expression and the cultures were incubated at 15° C. for 24 h. Cells were harvested by centrifugation (6 000×g for 5 min) and washed once with 20 mM Tris-HCl (pH 8.0). The cell pellet was frozen at −80° C. until purification could be performed. To purify His-tagged RlpE, the cells were thawed, suspended in lysis buffer (500 mM NaCl, 5% glycerol, 1% Triton X-100, 25 mM Tris-HCl, pH 8.0) and then lysed via sonication. Cell debris and insoluble protein was removed by centrifugation at 15 000×g for 30 min. The supernatant was mixed with 0.5 mL of HisPur Ni-NTA resin (Thermo Fisher Scientific). The resin was washed six times with 1.0 mL of 75 mM imidazole. His-tagged RlpE was eluted with 1.0 mL of 250 mM imidazole. Four batch elutions were performed and pooled. The imidazole elution buffer was exchanged with enzyme buffer (25 mM Tris-HCl, 10% glycerol) and concentrated by centrifugal filtration using a Macrosep 3 kDa spin filter (Pall). Following concentration the enzyme was aliquoted and stored at −80° C. The purity of the enzyme was analyzed by denaturing polyacrylamide gel electrophoresis (4-15% Mini-PROTEAN precast gel, 160 V, 30 min; Bio-Rad). The calculated molecular weight of His-tagged RlpE was 38.2 KDa. The apparent molecular weight of the purified protein was 33.05 kDa, which was in good agreement with the expected molecular weight (FIG. 2A).

The activity of RlpE was established by incubating the enzyme (0.1 µM) in reaction buffer (25 mM Tris-HCl pH 8.0, 2.5 mM MgCl$_2$) with 1 mM of TDP-L-rhamnose and 0.5 mM NB-RLP860. Reactions (200 µL) were incubated at 30° C. for 4 h. A portion (25 µL) of the reaction was removed at 15 s, 1 min, 5 min, 20 min, 1 h and 4 h. The reaction was stoped by the the addition of two volumes of methanol followed by flash freezing. Quenched reactions were separated by UPLC (Accela™, Thermo Fisher Scientific Mississauga, ON, Canada) and the eluates analyzed by HRES-IMS (LTQ Orbitrap Velos; Thermo Fisher Scientific) (positive mode, monitoring m/z 200-2000). Chromatographic separation was achieved with a Hypersil Gold 1.9 µm C$_{18}$ 175 Å 50×2.1 mm column (thermo Fisher Scientific) and a linear gradient from 50% H$_2$O/0.1% FA (solvent A) and 50% acetonitrile (CH$_3$CN)/0.1% FA (solvent B) to 100% solvent B over 5 min followed by a hold of 100% solvent B for 3 min with a flow rate of 300 µL/min. Reactions conducted with boiled enzyme showed no conversion of NB-RLP860 to NB-RLP1006. In contrast, enzyme reactions containing intact 6×His-RlpE resulted in the complete conversion of NB-RLP860 to NB-RLP1006 after 4 h (FIG. 2B). This data indicates that RlpE catalyzes the second rhamnosylation step in glycolipopeptide biosynthesis in *V. paradoxus* RKN-096. As genes for the biosynthesis of natural products in bacteria are typically clustered, this finding also provides strong evidence confirming the proposed gene cluster as the locus responsible for glycolipopeptide biosynthesis.

We also explored the ability of purified 6His-RlpE to iteratively add rhamnose units to NB-RLP860 by scanning the HRMS data for masses consistent with glycolipopeptide surfactants containing three rhamnose residues (calc'd [M+H]$^+$ 1153.7204), four rhamnose residues (calc'd [M+H]$^+$ 1299.7783) and five rhamnose residues (calc'd [M+H]$^+$ 1153.7204). Masses consistent with trirhamnosylated and tetrarhamnosylated reaction products were obtained and differed from the expected molecular weights by <1.03 parts per million (ppm) and <0.6 ppm, respectively. Interestingly, two peaks were observed for each mass, suggesting additional rhamnose units are attached at two different positions of the NB-RLP1006 structure. Relative to the production of NB-RLP1006 the tri-rhamnosylated and tetra-rhamnosylated glycolipopeptides constituted 2.99% and 0.14% of the reaction products. No penta-rhamnosylated glycolipopeptides were detected. This data indicates that recombinantly expressed RlpE can be used to generate glycolipopeptide analogs with upto four rhamnose residues. Such modifications may alter the functional properties of the glycolipopeptide. The properties can include but are not limited to wetting, foaming, surfactancy and emulsification.

Elucidation of the biosynthetic pathway for the glycolipopeptide biosurfactants produced by *V. paradoxus* RKNM-096 sets the stage for rational modification of the biosynthetic pathway to generate novel analogues or to increase yields. Analogues may be generated by those skilled in the art via modification of the enzymes responsible for the biosynthesis and incorporation of the lipid, peptide and carbohydrate portions of the molecule. Yields can be increased by those skilled in the art by modification of regulatory genes and or promoters, by overexpressing enzymes that represent rate limiting steps in the biosynthetic pathway or by inactivating enzymes which perform undesirable reactions. Knowledge of the biosynthetic pathway also enables expression in a heterologous host, which may enable yield improvements or the generation of glycolipopeptide analogues.

Example 8: Identification of Related Biosurfactants in Other Bacteria

Sequencing of the *V. paradoxus* RKNM-096 glycolipopeptide and rhamnose biosynthetic gene clusters was performed. Prior to the discovery of the glycolipopeptide series of biosurfactants and the associated biosynthetic gene cluster described herein, it would not have been possible to accurately predict the production of related glycolipopeptide biosurfactants based solely on DNA sequence analysis. Identification of the glycolipopeptide biosynthetic gene cluster now allows for targeted interrogation of microbial genomes for related gene clusters, which may have the potential to produce novel glycolipopeptide biosurfactants. As rlpC encodes a novel rhamnosyltransferase, which glycosylates an acylated dipeptide intermediate characteristic of the glycolipopeptide class of biosurfactants, we used the deduced amino acid sequence of this gene to search available bacterial genomes for homologs. This search identified homologs exhibiting to RlpC from a wide variety of bacteria. We then investigated genomic regions flanking the genes encoding the RlpC homologs for the presence of homologs of the other glycolipopeptide biosynthetic genes. Two examples will be presented to demonstrate the utility of using sequences from the glycolipopeptide gene cluster as probes to discover producers of putatively novel biosurfactants.

Figure 3:
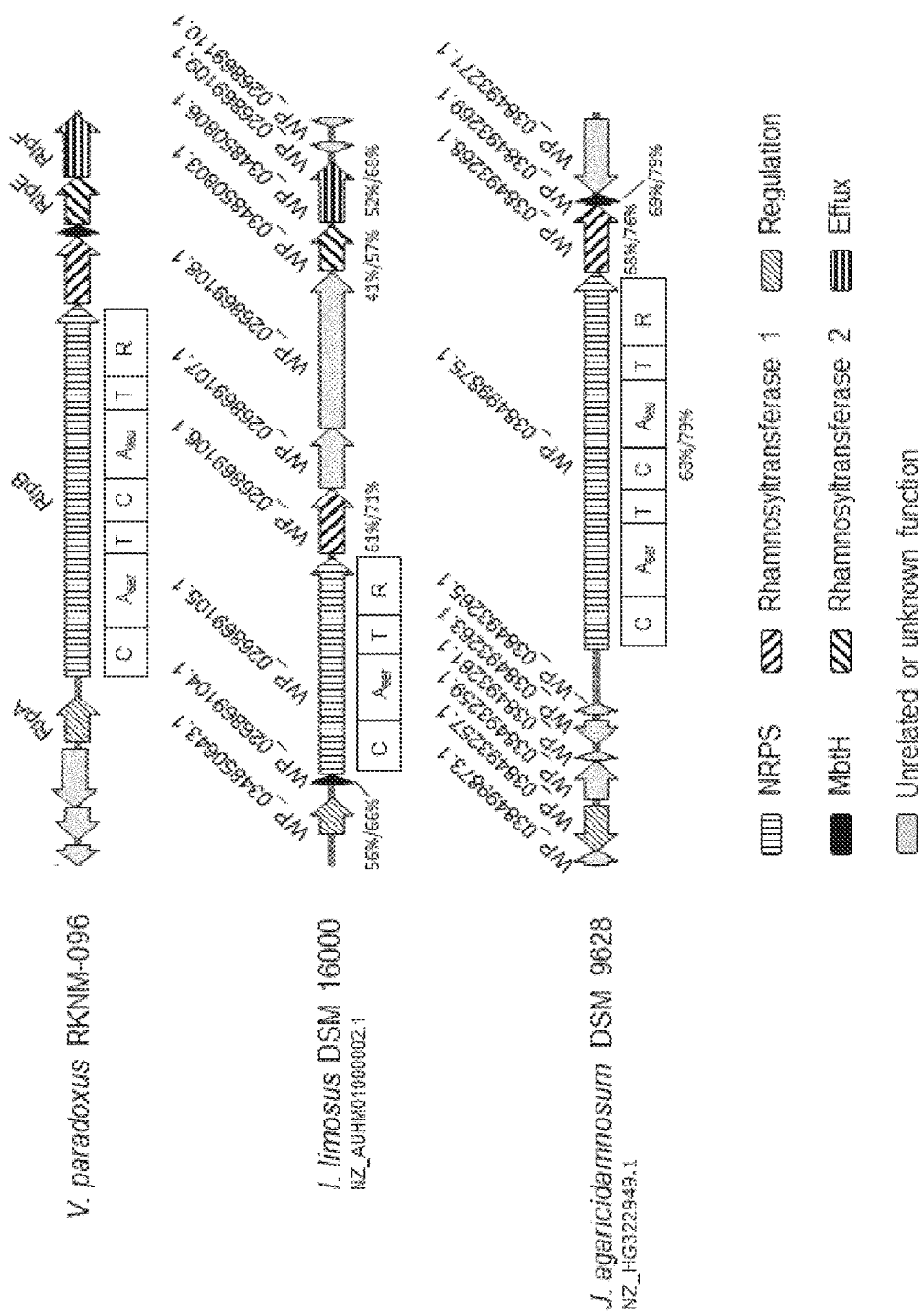
FIG. 3 is a schematic comparison of the *V. paradoxus* RKNM-096 glycolipopeptide gene cluster to homologous gene clusters identified in *I. limosus* DSM 16000 and *J. agaricidamnosum* DSM 9628. Genes encoding proteins homologous to proteins in the *V. paradoxus* gene cluster are indicated by arrow filling patterns. Identity and similarity to *V. paradoxus* proteins is indicated under arrows (identity %/similarity %). NRPS domain organization is indicated under arrows representing genes encoding non-ribosomal peptide synthetases (NRPSs). Domains: C—condensation, A—adenylation, T—thiolation/peptidyl-carrier protein, R—reductase. Subscript notation indicates putative A-domain substrate. Labels above arrows in the *I. limosus* and *J. agaricidamnosum* gene clusters indicate protein IDs.

A homologous gene cluster was identified in the Janthinobacterium agaricidamnosum DSM 9628 genome (GenBank accession no. NZ_HG322949.1) (FIG. 3). *J. agaricidamnosum* is a beta-proteobacterium like *V. paradoxus*, but belongs to a different family. The RlpC homolog in this strain (WP_038493268.1) exhibited 68% identity to RlpC. Scanning the genome around the RlpC homolog identified other homologs of genes present in the glycolipopeptide gene cluster. Directly downstream of the RlpC homolog was an MtbH-like protein (WP_038493269.1) which shared 69% identity with RlpD. Upstream a dimodular NRPS was identified (WP)038499875.1), which showed 68% identity to RlpB and contained an identical domain organization ([C-A-PCP]$_{M1}$-[C-A-PCP-R]$_{M2}$). Active site analysis (Bachmann and Ravel [2009] *Meth. Enzymol.* 458, 181) indicated that the predicted substrate specificity also matched that of RlpB, with the M1 A-domain specificity code matching that for L-serine and the M2 A-domain specificity code matching that of the M2 A-domain of RlpB, indicating L-leucine is incorporated by M2 (FIG. 3). A C-domain and R-domain were also found at the amino and carboxy-termini of the *J. agaricidamnosum* NRPS, respectively. This suggests that biosynthesis is initiated by condensation of an acyl intermediate with serine, and terminated by reductive release of an acylated dipeptide, similar to what is predicted for glycolipopeptide biosynthesis in *V. paradoxus* RKNM-096. No homolog to RlpE was found in the *J. agaricidamnosum* DSM 9628 gene cluster, indicating that the product of the cluster likely contains a single rhamnose residue. A gene cluster with a highly similar organization to that in *J. agaricidamnosum* DSM 9628 was also detected in the genome of *V. paradoxus* DSM 21786 (GenBank accession no. NC_022247.1). Collectively, this data suggests that *J. agaricidamnosum* DSM9628 and *V. paradoxus* DSM 21786 possess the ability to produce novel biosurfactants with structures related to those produced by *V. paradoxus* RKNM-096. Based on the bioinformatics analysis presented here, we predict the compound(s) produced by these bacteria would be a N-acylated L-serinyl-L-leucinol dipeptide bearing a single rhamnose residue.

Genome scanning using the RlpC sequence also identified a putative biosurfactant gene cluster in the more distantly related alpha-proteobacterium *Inquilinus limosus* DSM 16000 (Genbank accession no. NZ_AUHM01000002.1) (FIG. 3).The RlpC homolog (WP_026869107.1) in *I. limosus* shared 61% identity with the *V. paradoxus* RKNM-096 protein. Genes encoding a MtbH-like protein (WP_026869104.1) and a NRPS (WP026869105.1) were identified immediately upstream of the RlpC homolog. The MbtH-like protein shared 56% identity with RlpD. The NRPS was a monomodular enzyme with the following domain organization: C-A-T-R (FIG. 3). Active site analysis of the A-domain (Bachmann and Ravel [2009] *Meth. Enzymol.* 458, 181) indicated that L-serine is the likely substrate of this enzyme. The presence of a C-domain at the N-terminus and an R-domain at the C-terminus suggests that the product of the NRPS is an acylated serinol. An RlpE homolog (WP_034850803.1) was also detected in the *I. limosus* gene cluster (41% identity) suggesting that the acylated serinol intermediate may be sequentially glycosylated to yield a product bearing a dirhamnosyl moiety similar to NB-RLP1006. The final product may be exported out of the cell via the action of a MFS exporter (WP_034850806.1) which shares 52% identity with RlpF.

To validate our in silico approach to identifying producers of glycolipopeptide biosurfactants we obtained *J. agaricidamnosum* DSM 9628 and *V. paradoxus* DSM 21786 from the Deutsche Sammlung von Mikroorganismen and Zellkulturen (DSMZ) culture collection. Each strain was fermented in a variety of culture media to promote production of predicted biosurfactants. Fermentations were extracted twice with an equal volume of EtOAc. The organic layer was evaporated and the resulting concentrated extracts were analyzed by UPLC-PDA-ELSD-HRESIMS as described above for NB-RLP1006 (Example 3). Three prominent peaks eluting at 3.07, 5.05 and 5.51 min were observed in the ELSD and HRESIMS chromatograms of *J. agaricidamnosum* DSM 9628. The peak at 3.07 min (HRESIMS m/z 1182.6217 [M+H]$^+$, calcd for $C_{56}H_{85}N_{12}O_{16}$, 1181.6201) could be attributed to the known compound jagaracin previously reported from this strain (Graupner et al. [2012]

Angew Chem. Int. Ed. Engl. 51:13173). Extraction of the mass spectra for peaks eluting at 5.05 and 5.51 min revealed [M+H]⁺ ions of m/z 833.5741 and m/z 861.6033, respectively. The observed [M+H]⁺ ions showed a −1.5 and 1.0 ppm mass difference from predicted m/z [M+H]⁺ ions for the monorhamnosyl glycolipopeptides NB-RLP832 (m/z 833.5741 [M+H]⁺) and NB-RLP860 (m/z 861.6033 [M+H]⁺), respectively, indicating the expected compounds had been produced by *J. agaricidamnosum* DSM 9628. Similar to NB-RLP978A-C and NB-RLP1020A-C, the mass of NB-RLP832 closely matched that predicted for an analogue of NB-RLP860 lacking two methylene groups. These compounds were purified and their structures elucidated using a combination of 1D and 2D NMR experiments. This analysis unambiguously confirmed that the expected monorhamnosylated biosurfactant had been produced by *J. agaricidamnosum* DSM 9628 (see Example 3).

Identical analysis of *V. paradoxus* DSM 21786 fermentation extracts also revealed the presence of a peak eluting at 5.51 min in the HRESIMS chromatogram. Inspection of the mass spectrum associated with this peak revealed the presence of a [M+H]⁺ ion with a m/z of 861.6104, which differed from the expected mass ([M+H]⁺ m/z 861.6046) by 5.8 ppm. The identical retention time and monoisotopic mass indicated that both *J. agaricidamnosum* DSM 9628 and *V. paradoxus* DSM 21786 produce NB-RLP860.

What is claimed is:

1. A purified biosurfactant comprising a hydrophobic lipid component comprising a carboxyl end and a hydroxyl end, wherein the lipid component is covalently linked to (i) a peptide or nonproteinogenic amino acid chain at the carboxyl end of the lipid component and (ii) a carbohydrate moiety at the hydroxyl end of the lipid component via a glycosidic linkage, wherein the carbohydrate moiety includes one, two or three rhamnose moieties, wherein one or more rhamnose hydroxy groups are acetylated if there is one rhamnose moiety and two or more rhamnose hydroxy groups are acetylated if there are two rhamnose moieties.

2. The purified biosurfactant according to claim 1, wherein the peptide chain comprises between 2 and 10 amino acids.

3. The purified biosurfactant according to claim 1, wherein the lipid component comprises between 1 and 6 alkanoic acid moieties.

4. The purified biosurfactant according to claim 1, wherein the lipid component comprises an acyl chain, the acyl chain having a length in a range of between $C_4$ to $C_{20}$.

5. The purified biosurfactant according to claim 1, wherein the peptide or nonproteinogenic amino acid chain comprises a serine-leucinol dipeptide.

6. The purified biosurfactant according to claim 1, wherein the lipid component comprises three β-hydroxyalkanoic acid moieties.

7. The purified biosurfactant of claim 4, wherein each acyl chain of the lipid component has a length of $C_{10}$.

8. The purified biosurfactant according to claim 1, wherein the carbohydrate moiety includes a rhamnose moiety attached to the lipid component via a glycosidic linkage.

9. The purified biosurfactant according to claim 1, wherein the carbohydrate moiety includes two rhamnose moieties.

10. The purified biosurfactant according to claim 1, wherein the lipid component comprises three β-hydroxyalkanoic acid moieties, the length of each acyl chain of the lipid component is $C_{10}$, and the carbohydrate moiety includes a rhamnose moiety attached to the lipid component via a glycosidic linkage.

\* \* \* \* \*